US006824972B2

(12) United States Patent
Kenwrick et al.

(10) Patent No.: US 6,824,972 B2
(45) Date of Patent: Nov. 30, 2004

(54) DIAGNOSIS AND TREATMENT OF MEDICAL CONDITIONS ASSOCIATED WITH DEFECTIVE NFKAPPA B(NF-κB) ACTIVATION

(75) Inventors: Sue J. Kenwrick, Cambridge (GB); Hayley Woffendin, Cambridge (GB); Arnold Munnich, Paris (FR); Asmae Smahi, Saint Ouen (FR); Alain Israel, Paris (FR); Annemarie Poustka, Ladenburger Str. 41, Heidelberg, 69120 (DE); Nina Heiss, Bahnhofstr. 9-13, Heidelberg, 69115 (DE); Michele D'Urso, Naples (IT); Richard A. Lewis, Houston, TX (US); David L. Nelson, Houston, TX (US); Swaroop Aradhya, Houston, TX (US); Moise Levy, Houston, TX (US)

(73) Assignees: Baylor College of Medicine, Houston, TX (US); Cambridge University Technical Services Limited, Cambridge (GB); Consiglio Nazionale Delle Richerche, Rome (IT); INSERM, Cedex 13 (FR); L'Institut Pasteur, Paris (FR); Annemarie Poustka, Heidelberg (DE); Nina Heiss, Heidelberg (DE)

( * ) Notice: Subject to any disclaimer, the term of this patent is extended or adjusted under 35 U.S.C. 154(b) by 10 days.

(21) Appl. No.: 09/863,049

(22) Filed: May 22, 2001

(65) Prior Publication Data

US 2003/0032055 A1 Feb. 13, 2003

Related U.S. Application Data

(60) Provisional application No. 60/206,223, filed on May 22, 2000.

(51) Int. Cl.[7] ............................ C12Q 1/00; C12Q 1/68; C12Q 1/70; G01N 33/53; C07H 21/04
(52) U.S. Cl. ....................... 435/4; 435/5; 435/6; 435/7; 536/23.1
(58) Field of Search ............................... 435/4, 5, 6, 7; 536/23.1

(56) References Cited

PUBLICATIONS

Baldwin et al. (1996) Annu. Rev. Immunol., vol. 14:649–681.*
Mutations in Brief, Human Mutation vol. 12, No. 5, (Oct. 7, 1998), pp. 361–363.
Rothnie, Helen, M. et al.; Polyadenylation in Rice Tungro Bacilliform Virus: cis–Acting Signals and Regulation, Journal of Virology (May 2001), vol. 75, No. 9, pp. 4184–4194.
McQueen, Karina L., et al.; Functional analysis of 5' and 3' regions of the closely related Ly49c and j genes, Immunogenetics (2001) vol. 52, pp. 212–223.

Graber, Joel H., et al.; In silico detection of control signals: mRNA 3' –end–processing sequences in diverse species, PNAS (Nov. 23, 1999), vol. 96, No. 24, pp. 14055–14060.
Xu, Zhi–Li, et al.; Optimization of transcriptional regulatory elements for constructing plasmid vectors, Int'l Journal of Genes and Genomes, (2001), vol. 272, pp. 149–156.
Shamsher, Monee K., et al.; Identification of an intronic regulatory element in the human protein C (PROC) gene, Human Genetics (2000), vol. 107, pp. 458–465.
Ionasescu, V.V., et al.; Mutations of the noncoding region of the connexin32 gene in X–linked dominant Charcot–Marie–Tooth neuropathy, American Academy of Neurology (1996), vol. 47, pp. 541–544.
Harland, Mark, et al.; Mutation Screening of the CKDKN2A Promoter in Melanoma Families, Genes, Chromosomes & Cancer (2000) vol. 28, pp. 45–57.
Pyne, Michael T., et al.; The BRCA2 genetic variant IVS7+2T—G is a mutation, J. Hum. Genetics (2000), vol. 45, pp. 351–357.
Jannssen R.J., et al.; A branch site mutation leading to aberrant splicing of the human tyrosine hydroxylase gene in a child with a severe extrapyramidal movement disorder, Am. Hum. Genet. (2000), vol. 64, pp. 375–382.
Hobson, G.M., et al.; Mutations in noncoding regions of the protelolipid protein gene in pelizaeous—Merzbacher disease, Neurology (2000), vol. 55, pp. 1089–1096.
Aradhya, Swaroop, et al.; Multiple pathogenic and benign genomic rearrangments occur at a 35 kb duplication involving the NEMO and LAGE2 genes, Hum. Mol. Genet. (2001), vol. 10, No. 22, pp. 2557–2567.
Galgoczy, Petra, et al.; Human–mouse comparative sequence analysis of the NEMO gene reveals an alternative promoter within the neighboring G6PD gene, Int'l Journal of Genes and Genomoes, (2001), vol. 271, pp. 93–98.
Mayer, E J, et al; Novel corneal featurs in two males wih incontinentia pigmenti; Br J Ophthalmol 2003; 87:554–556.
Bardaro, Tiziana et al; Two Cases of Misinterpretation of Molecular Results in Incontinentia Pigmenti, and a PCR–Based Method to Discriminate NEMO/IKKy Gene Deletion; Human Mutation 21:8–11 (2002).

(List continued on next page.)

Primary Examiner—Anne Marie S. Wehbé
(74) Attorney, Agent, or Firm—Fulbright & Jaworski, LLP

(57) ABSTRACT

Incontinentia Pigmenti (IP) is a neurocutaneous genodermatosis that segregates as an X–linked dominant disorder with a high probability of prenatal male lethality. A locus in Xq28 containing NF-κB Essential Modulator, a gene product involved in the activation of NF-kB and central to many pro-inflammatory and apoptotic pathways, contains mutations in the majority of cases of IP. Disclosed are methods, compositions and kits directed to a defect in a NF-κB related disease such as IP.

13 Claims, 13 Drawing Sheets

OTHER PUBLICATIONS

Chaturvedi, LS et al; Point mutation and polymorphism in Duchenne/Becker Muscular Dystrophy (D/BMD) patients; Experimental and Molecular Medicine, vol. 33, No. 4,251–256, Dec. 2001.

Shahbazian, Mone D. et al; Molecular genetics of Rett syndrome and clinical spectrum of MECP2 mutations; Developmental disorders 2001 Lippincott Williams & Wilkins pp. 171–176.

Jin, Dong–Yan, et al.; Isolation of Full–Length cDNA and Chromosomal Localization of Human NF-kB Modulator NEMO to Xq28; J Biomed Sci 1999; 6:115–120.

Rothwarf, David M., et al.; Letters to Nature: IKK–y is an essential regulatory subunit of the IkB kinase complex; Nature, vol. 395, pp. 297–300, Sep. 17, 1998.

Woffendin, H., et al.; Short Report: X–inactivation and marker studies in three families with incontinentia pigmenti: implications for counselling and gene localisation; Clin Genet 1999: 55:55–60.

Parrish, Julia E., et al.; Selectino against mutant alleles in blood leukocytes is a consistent feature in Incontinentia Pigmenti Type 2: Human Molecular Genetics, 1996, vol. 5 (11), 1777–1783.

Smahl, A., et al.; The gene for the familial form of incontinentia pigmenti (IP2) maps for the distal part of Xq28; Human Molecular Genetics, 1994, vol. 3 (2), 273–278.

Yamaoka, Shoji, et al.; Complementation Cloning of NEMO, a Component of the IkB kinase Complex Essential for NF–kB Activation; Cell, vol. 93, 1231–1240, Jun. 26, 1998.

Mercurio, Frank, et al.; IkB Kinase (IKK)–Associated Protein 1, a Common Component of the Heterogeneous IKK Complex; Molecular and Cellular Biology, vol. 19 (2), Feb. 1999, p. 1526–1538.

Jouet, Monique, et al; Short Report—Linkage Analysis in 16 Families with Incontinentia pigmenti, Eur J Hum Genet 1997; 5:168–170.

Ghosh, Sankar, et al.; NF–kB and REL Proteins: Evolutionarily Conserved Mediators of Immune Responses; Annu. Rev. Immunol. 1998. 16:225–60.

Editor; Mutation analysis of the DKC1 gene in incontinentia pigmenti; Letters J. Med Genet 1999; 36:860–862.

Sefiani, A., et al.; Short Communication: The Gene for Incontinentia Pigmenti is Assigned to Xq28; Genomics 4, 427–429 (1989).

Baldwin, Jr., Albert S.; The NF–kB and IkB Proteins: New Discoveries and Insights; Annu. Rev. Immunol. 1996, 14:649–81.

Aradhya, Swaroop, et al; A recurrent deletion in the ubiquitously expressed NEMO (IKK–y) gene accounts for the vast majority of incontinentia pigmenti mutations; Human Molecular Genetics, 2001, vol. 10 (19), 2171–2179.

Aradhya, Swaroop, et al.; Report: Atypical Forms of Incontinentia Pigmenti in Male Individuals Result from Mutations of a Cystosine Tract in Exon 10 of NEMO (IKK–y); Am. J. Hum. Genet. 68:765–771, 2001.

Genomic rearrangement in NEMO impairs NF–kB activation and is a cause of incontinentia pigmenti; Letters to Nature; Nature, vol. 405, pp. 466–472, May 25, 2000.

* cited by examiner

DIAGNOSIS AND TREATMENT OF MEDICAL CONDITIONS ASSOCIATED WITH DEFECTIVE NFKAPPA B(NF-κB) ACTIVATION

This application claims priority to U.S. Provisional Patent Application Ser. No. 60/206,223, filed May 22, 2000.

The work herein was supported in part by the grant NIH-RO1-HD-35617 from the United States Government. The Government may have certain rights in the invention.

FIELD OF THE INVENTION

This invention generally relates to defective NF-κB activation through loss of functional NF-κB Essential Modulator (NEMO). More specifically, the invention relates to diagnosis and treatment in organisms with medical conditions related to defective NF-κB Essential Modulator.

BACKGROUND OF THE INVENTION

Incontinentia Pigmenti (IP), or Bloch-Sulzberger Syndrome, is an X-linked dominant, male-lethal disorder with four classic cutaneous stages that begin in the neonatal period: 1) blisters and vesicles on an erythematous base; 2) raised pustular and verrucous cutaneous patches; 3) hyperpigmentation in a distinctive pattern assumed to represent lines of cell migration (lines of Blaschko); and 4) scarred dermal hypopigmentation and atrophy with absence of the hair follicles and sweat glands. The early inflammatory stages are accompanied by eosinophilia both in the peripheral blood and in the skin lesions. Streaks and whorls of hyperpigmentation give the condition its name and result from release of melanin from cells of the epidermis into the dermis, generally by 6 months of age, particularly in the axillae and groin. This "marble cake" hyperpigmentation fades, typically by the third decade, leaving superficially scarred, hairless, pale tissue as the subtle dermatologic sign in adulthood. IP is often associated with developmental abnormalities of the teeth, eyes, hair, and the central nervous system (reviewed in Carney, 1976; Landy, 1993; Francis, 1997). Dental abnormalities, typically anodontia and hypodontia, conical pegging, delayed eruption, and malformed crowns with soft enamel, affect about 80% of cases (Garcia-Bravo, 1986; Optiz, 1981). Ophthalmologic anomalies, particularly dysplasia of retinal vessels, cicatrization and retinal folds, and tractional retinal detachment, affect about one-third of cases (Rosenfeld, 1985; Goldberg, 1993). Approximately 10–30% also manifest permanent neurological defects, such as intracranial vascular occlusions, neuronal remodeling or migration defects, mental retardation, hypotonia, spasticity, epilepsy, and microcephaly (Landy, 1993). IP females may also have partial or patchy alopecia even on the scalp, mild dystrophic changes in the nails, or supernumerary nipples or hypoplasia or aplasia of the breast, and show periungual keratotic tumours of the hands (Adeniran, 1993; Baran, 1998).

At birth, the ratio of female:male offspring from known affected females is consistent with lethality in utero among male conceptuses (Carney, 1976). The reasons for spontaneous male abortion (usually in the second and occasionally the third trimester) are unclear, although post mortem examination of a few cases has revealed infiltration of immune cells into tissues, indicating that IP may involve an immune response (Roberts, 1998). IP females exhibit severely skewed (>98%) X-inactivation in white blood cells and fibroblasts resulting from loss of cells expressing the mutated X (Parrish, 1996). Elimination of defective cells is likely to occur close to or immediately after birth rather than in utero in these tissues, since cell populations expressing both X-chromosomes can be derived from cord blood or from neonatal skin (Parrish, 1996). This selective mechanism may explain both the difference in morbidity between hemizygous males and heterozygous females and the gradual resolution of many of the skin signs in affected females. The cause of cell loss is unknown, although it coincides with the early inflammatory skin lesions.

Linkage of the IP locus to markers in distal Xq28 (DXS52-tel) was established with close linkage to the gene for factor VIII (Sefiani, 1989; Smahi, 1994; Parrish, 1996; Jouet, 1997) Many genes from this region have been excluded by extensive mutation screening (Heiss, 1999; Aradhya, 2000; Woffendin, 2000; Das, 1994). Recently, a gene intimately involved in inflammatory responses, NEMO/IKKγ, has been mapped 200 kb proximal to the factor VIII locus (Jin, 1999). NEMO is central to the activation of the ubiquitous transcription factor NF-κB (Yamaoka, 1998; Rudolph, 2000). The NF-κB/Rel family of transcription factors plays a particularly important role in inflammatory and immune responses, in cellular stress, and in regulating apoptosis (Ghosh, 1998; Baldwin, 1996). Their activity is induced by a variety of different stimuli including pro-inflammatory cytokines such as interleukin-1 (IL-1) and Tumour Necrosis Factor (TNF). The immediate responsiveness required of such a key regulator is effected by an unique mechanism whereby NF-κB homo- or heterodimers are sequestered in the cytoplasm through interaction with an inhibitory molecule of the IKB family (three different species exist in cells: IκBα, IκBβ and IκBε). Upon cytokine stimulation the IκB molecules are phosphorylated on two Ser residues, then polyubiquitinated and degraded through the ubiquitin-proteasome pathway. NF-κB is therefore free to translocate to the nucleus and to activate its target genes. This phosphorylation event is carried out by a high molecular weight, multiprotein kinase complex containing two subunits with kinase activity (IKK1/α and IKK2/β) (Zandi, 1999; Mercurio, 1999). A third component of this complex is a 48 kDa protein with no apparent catalytic activity, called NEMO (NF-κB Essential Modulator), IKKγ, or IKKAP (Yamaoka, 1998; Rothwarf, 1998; Mercurio, 1999). NEMO directly interacts with the kinase subunits and is required for activation of the kinase complex in response to extracellular (or intracellular) stimuli: its absence results in a complete inhibition of NF-κB activation.

Enhanced apoptosis might explain the selection against cells expressing the IP mutation in affected females (Smahi et al.). In support of this notion, patient-derived cell lines exhibit a high sensitivity to TNF-induced cell death. Based on these observations and the chromosomal localization of the gene in Xq28, a possible role of NEMO in IP was investigated.

BRIEF DESCRIPTION OF THE DRAWINGS

FIG. 2A indicates DNA fragments detected by cDNA probes of NEMO exons 2–10.

FIG. 2B illustrates a partial restriction map of the NEMO locus.

FIG. 2C is a diagram of the NEMO locus highlighting exon locations and primer sites.

In FIG. 3A there is a Southern blot hybridized with NEMO cDNA representing exons 2–10 showing the appearance of novel Eco RI (2.8 kb) and novel Hind III (8 kb) bands in unrelated IP females compared to controls.

FIG. 3B demonstrates novel Eco RI and Hind III bands which appear de novo with the disease in sporadic cases of IP (IP44 and IP91).

FIG. 3C demonstrates long range PCR across the NEMO gene in male patient IP1 m.

FIG. 3D shows diagnostic PCR in IP patients with the rearrangement.

FIG. 3E illustrates a model for IP rearrangements.

FIG. 4A shows that the full length NEMO amino acid sequence is not detected in IP embryonic fibroblasts (EFs).

FIG. 4B illustrates that NF-κB is not activated in IP embryonic fibroblasts.

FIG. 4C demonstrates IκBα degradation is defective in IP embryonic fibroblasts.

FIG. 4D shows IP embryonic fibroblasts are TNF-sensitive.

FIG. 5A shows a 10 bp insertion in exon 2 is shown to segregate with the disease in family XL349 using heteroduplex analysis. The insertion causes a frameshift and mixed sequence in heterozygous female XL349-04. Novel amino acids due to the translational frameshift are shown in bold and italics.

FIG. 5B shows segregation of the 1 bp insertion in exon 9 in family XL203 as determined by heteroduplex analysis. In this case the two homoduplex bands (mutant and wild type) are also seen to have a different gel migration distance.

FIG. 5C shows missense mutation M407V segregates with the disease in family 72 (+=wild type, M=M407V mutation) as determined by sequence analysis of family DNAs.

FIG. 5D shows the C to T, proline to STOP codon mutation found in exon 2 in family XL352.

SUMMARY OF THE INVENTION

Figure 1:
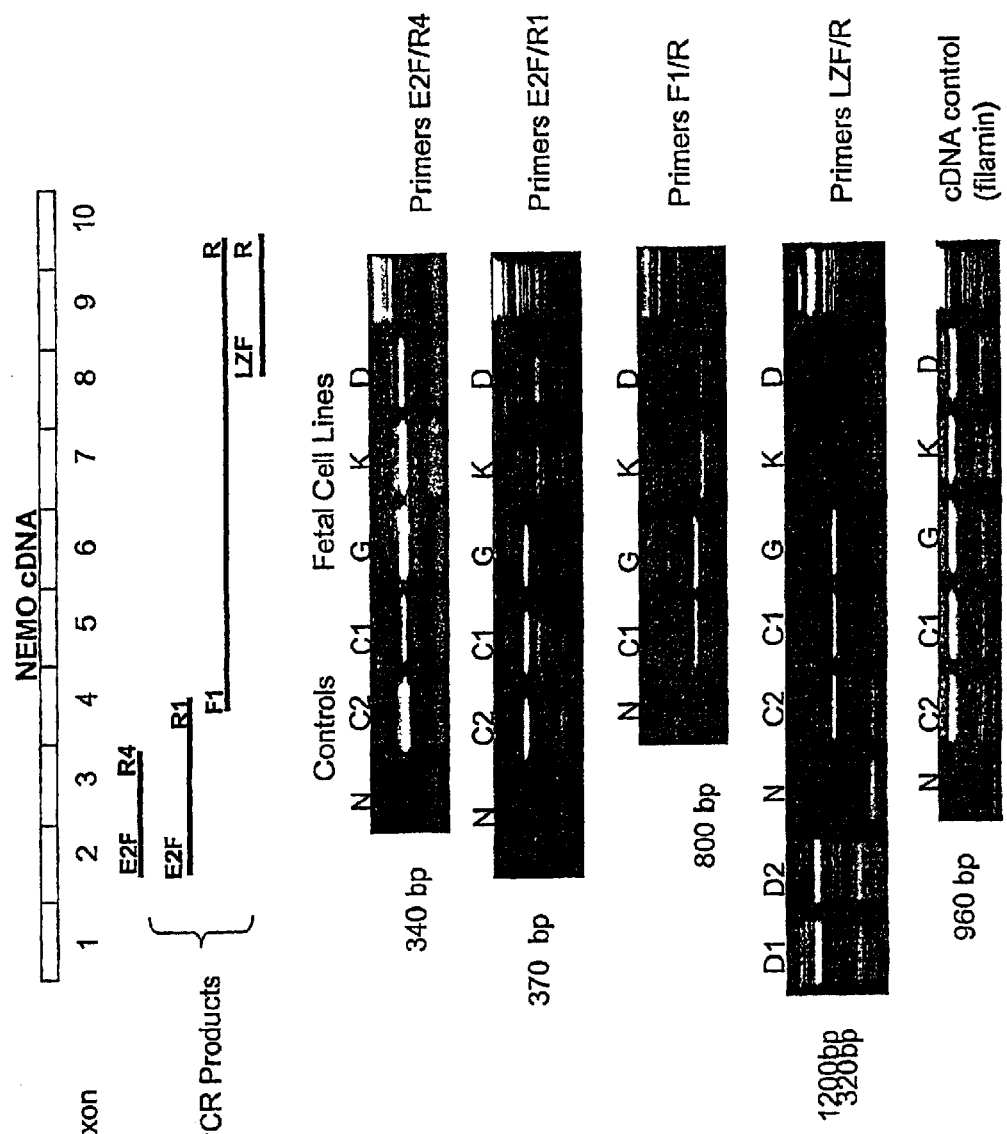
FIG. 1 represents amplification by RT-PCR of NEMO cDNA from IP patient cell lines.

In an embodiment of the present invention is a method to detect a NF-κB related medical condition in an organism comprising the steps of obtaining a sample from an organism and analyzing the sample for an alteration in a nucleic acid of SEQ ID NO:1, wherein said alteration is associated with inactivation of NF-κB. In a specific embodiment the alteration is a mutation, wherein said mutation is selected from the group consisting of a deletion, an insertion, a point mutation and a rearrangement. In another specific embodiment the point mutation is selected from the group consisting of a nonsense mutation, a frameshift mutation, a missense mutation and a splicing-related mutation. In a further embodiment the alteration in said NF-κB Essential Modulator nucleic acid is located in a regulatory nucleic acid, a promoter nucleic acid, an exon, an intron, an initiator codon, a stop codon, an exon/intron junction, a 5' untranslated region, a 3' untranslated region and a combination thereof. In a specific embodiment the detection of a alteration in said NF-κB Essential Modulator nucleic acid is by a method selected from the group consisting of hybridization, SSCP, heteroduplex analysis, sequencing, polymerase chain reaction and electrophoresis. In a preferred embodiment the NF-κB related medical condition is Incontinentia Pigmenti. In another preferred embodiment the organism is a human. In an additional preferred embodiment the NF-κB related medical condition is a -κB Essential Modulator related medical condition.

In an embodiment of the present invention there is a method to detect a NF-κB related medical condition in an organism comprising the step of detecting an alteration in a NF-κB Essential Modulator amino acid of SEQ ID NO:2, wherein said alteration is associated with inactivation of NF-κB. In a specific embodiment said alteration is an addition, deletion, or substitution of the amino acid sequence. In another specific embodiment the detection of said alteration is selected from the group consisting of sequencing, mass spectrometry, by molecular weight or with antibodies. In an additional specific embodiment the NF-κB related medical condition is Incontinentia Pigmenti. In an additional preferred embodiment the NF-κB related medical condition is a -κB Essential Modulator related medical condition.

In another embodiment of the present invention there is a method to treat a NF-κB related medical condition in an organism comprising the step of administering to said organism therapeutically effective amounts of a NF-κB Essential Modulator nucleic acid of SEQ ID NO:1. In a specific embodiment the administration of said nucleic acid comprises a vector. In another specific embodiment the vector is selected from the group consisting of a nucleic acid, an amino acid, a lipid, a liposome, a sugar, a carbohydrate or a combination thereof. In a further embodiment the nucleic acid vector is selected from the group consisting of an adenoviral vector, an adenoviral-associated vector, a retroviral vector or a combination thereof. In a specific embodiment the NF-κB related medical condition is selected from the group consisting of an apoptosis-related disease, an immune-system related disease, a blood vessel-related disease, a skin defect, a dental defect, osteopetrosis, an ophthamalogical defect, a neurological defect and Incontinentia Pigmenti. In an additional specific embodiment the NF-κB related medical condition is Incontinentia Pigmenti.

In an additional embodiment of the present invention there is a method to treat an organism with an NF-κB related medical condition comprising the step of: administering to said organism therapeutically effective amounts of a NF-κB Essential Modulator amino acid of SEQ ID NO:2. In a specific embodiment the administration of said NF-κB Essential Modulator amino acid comprises a protein transduction domain. In another specific embodiment the protein transduction domain is the HIV TAT domain. In a specific embodiment the NF-κB related medical condition is selected from the group consisting of an apoptosis-related disease, an immune-system related disease, a blood vessel-related disease, a skin defect, a dental defect, osteopetrosis, an opthamalogical defect, a neurological defect and Incontinentia Pigmenti. In an additional specific embodiment the NF-κB related medical condition is Incontinentia Pigmenti.

In an embodiment of the present invention there is a method to prevent a NF-κB related medical condition in an organism comprising the step of administering to said organism a NF-κB Essential Modulator nucleic acid of SEQ ID NO:1 or a NF-κB Essential Modulator amino acid of SEQ ID NO:2. In specific embodiments said NF-κB related medical condition is Incontinentia Pigmenti and said administration occurs in utero or to an infant. In another specific embodiment the NF-κB related medical condition is selected from the group consisting of an apoptosis-related disease, an immune-system related disease, a blood vessel-related disease, a skin defect, a dental defect, osteopetrosis, an opthamalogical defect, a neurological defect and Incontinentia Pigmenti.

In another embodiment of the present invention there is a method to screen in a test organism for a compound for the treatment of a NF-κB related medical condition, wherein said test organism has an alteration in a nucleic acid of SEQ ID NO:1, wherein said alteration results in inactivation of NF-κB, comprising the step of administering said compound to said organism and assaying for an improvement in said NF-κB related medical condition. In specific embodiments said NF-κB related medical condition is Incontinentia Pigmenti.

In another embodiment of the present invention there is a method to screen in a test organism for a compound for the treatment of a NF-κB related medical condition, wherein said test organism has an alteration in an amino acid of SEQ ID NO:2, wherein said alteration results in inactivation of NF-κB, comprising the step of administering said compound to said organism and assaying for an improvement in said NF-κB related medical condition. In specific embodiments said NF-κB related medical condition is Incontinentia Pigmenti.

In another embodiment of the present invention there is a composition for the treatment of a NF-κB related medical condition in an organism comprising a therapeutically effective amount of a nucleic acid of SEQ ID NO:1 or an amino acid of SEQ ID NO:2 and a pharmaceutically acceptable carrier.

In another embodiment of the present invention there is a method to detect an alteration in a nucleic acid SEQ ID NO:1 in an organism comprising the steps of obtaining a sample from the organism and analyzing the sample for the alteration. In a specific embodiment the alteration is a mutation, wherein said mutation is selected from the group consisting of a deletion, an insertion, a point mutation and a rearrangement. In another specific embodiment the point mutation is selected from the group consisting of a nonsense mutation, a frameshift mutation, a missense mutation and a splicing-related mutation. In a further embodiment the alteration in said NF-κB Essential Modulator nucleic acid sequence is located in a regulatory nucleic acid, a promoter nucleic acid, an exon, an intron, an initiator codon, a stop codon, an exon/intron junction, a 5' untranslated region, a 3' untranslated region and a combination thereof. In a specific embodiment the detection of a alteration in said NF-κB Essential Modulator nucleic acid is by a method selected from the group consisting of hybridization, SSCP, heteroduplex analysis, sequencing, polymerase chain reaction and electrophoresis. In another embodiment the organism is a human. In an additional embodiment the organism is a human selected from the group consisting of an affected individual, a carrier individual or a noncarrier individual. In a further embodiment the analyzing step further comprises a technique selected from the group consisting of PCR analysis and Southern blot analysis. In an additional embodiment the PCR analysis utilizes at least one primer selected from the group consisting of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO12, SEQ ID NO:13, SEQ ID NO:14, SEQ ID NO:15, SEQ ID NO:16, SEQ ID NO: 17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO: 43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60; and SEQ ID NO:61. In a further embodiment the PCR analysis utilizes two primers selected from the group consisting of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO12, SEQ ID NO:13, SEQ ID NO:14, SEQ ID NO:15, SEQ ID NO:16, SEQ ID NO: 17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO: 43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:66, SEQ ID NO:67, SEQ ID NO:70, SEQ ID NO:71, SEQ ID NO:74, SEQ ID NO:75, and fragments and derivatives thereof.

In a specific embodiment the PCR analysis utilizes a primer SEQ ID NO:50 and a primer SEQ ID NO:34.

In an additional specific embodiment the probe for the Southern analysis is a nucleic acid of SEQ ID NO:3, or fragments and derivatives thereof.

In an embodiment of the present invention there is a method to detect an alteration in a nucleic acid SEQ ID NO:2 in an organism, comprising the steps of obtaining a sample from said organism; and analyzing said sample for said alteration.

In another embodiment of the present invention there is a kit for the detection of an alteration in a nucleic acid of SEQ ID NO:1 comprising at least two primers for polymerase chain reaction.

In an additional embodiment of the present invention there is a kit for the detection of an alteration in a nucleic acid of SEQ ID NO:1 comprising at least two primers selected from the group consisting of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO12, SEQ ID NO:13, SEQ ID NO:14, SEQ ID NO:15, SEQ ID NO:16, SEQ ID NO: 17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO: 43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60; SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77 and fragments and derivatives thereof.

In a further embodiment of the present invention there is a nucleic acid of SEQ ID NO:1, and fragments and derivatives thereof. In a specific embodiment the nucleic acid sequence is selected from the group consisting of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO12, SEQ ID NO:13, SEQ ID NO:14, SEQ ID NO:15, SEQ ID NO:16, SEQ ID NO: 17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO: 43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60; SEQ ID NO:61; SEQ ID NO:62, SEQ ID NO:63, SEQ ID NO:66, SEQ ID NO:67, SEQ ID NO:70, SEQ ID NO:71, SEQ ID NO:74, SEQ ID NO:75, and fragments and derivatives thereof.

In a further embodiment of the present invention there is an amino acid selected from the group consisting of SEQ ID NO:64, SEQ ID NO:65, SEQ ID NO:68, SEQ ID NO:69, SEQ ID NO:72, SEQ ID NO:73, SEQ ID NO:76 and SEQ ID NO:77, and fragments and derivatives thereof.

In a further embodiment of the present invention there is a kit for the treatment of a NF-κB related medical condition in an organism comprising a therapeutically effective amount of a NF-κB Essential Modulator nucleic acid of SEQ ID NO:1 or an amino acid of SEQ ID NO:2 and a pharmaceutically acceptable carrier. In a specific embodiment the NF-κB related medical condition is Incontinentia Pigmenti.

DESCRIPTION OF THE INVENTION

It is readily apparent to one skilled in the art that various embodiments and modifications may be made to the invention disclosed in this Application without departing from the scope and spirit of the invention.

As used herein the specification, "a" or "an" may mean one or more. As used herein in the claims, when used in conjunction with the word "comprising," the words "a" or "an" may mean one or more than one. As used herein "another" may mean at least a second or more.

The term "affected individual" as used herein is defined as an individual who has at least one symptom of Incontinentia Pigmenti. In a specific embodiment the individual is homozygous for a mutation in SEQ ID NO:1.

The term "apoptosis" as used herein is defined as programmed cell death.

The term "apoptosis-related medical condition" as used herein is defined as any disease or undesirable state of health associated with apoptosis.

The term "carrier individual" as used herein is defined as an individual who has an alteration such as a mutation in a sequence SEQ ID NO:1. In a specific embodiment the carrier individual contains a mutation but does not present any symptoms of Incontinentia Pigmenti. In another specific embodiment said carrier individual has a family member who has at least one symptom of Incontinentia Pigment. In an additional specific embodiment the family member is a father, mother, brother, sister, daughter, son, grandfather, grandmother, aunt, uncle or cousin. In a specific embodiment the individual is a heterozygote for a mutation in SEQ ID NO:1.

The term "dental defect" as used herein is defined as any abnormality or defect related to the teeth or gums. The deficiency may affect "baby" teeth or adult teeth, or both. Deficiencies include anodontia, hypodontia, conical pegging, delayed eruption, and malformed crowns with soft enamel.

The term "DNA" as used herein is defined as deoxyribonucleic acid.

The term "exon" as used herein is defined as a transcribed segment of a gene that is present in a mature messenger RNA molecule.

The term "exon/intron junction" as used herein is defined as two specific nucleotide locations at which point an intronic sequence is spliced from an RNA transcript. A skilled artisan is aware that this term is used interchangeably in the art with the term "splice site."

The term "fragments and derivatives thereof" as used herein is defined as alterations of specific nucleic acid including mutations, chemical modifications, deletions or additions which still allow the nucleic acid to function or the amino acid it encodes to function. Such changes in a specific embodiment can enhance or decrease the ability of the function. Furthermore, subregions of said nucleic acid could also contain mutations, chemical modifications, deletions or additions which still allow said subregion to function or the amino acid it encodes to function.

The term "inactivation" as used herein is defined as the loss of activity, function or structure, in a specific embodiment, of NF-κB. The inactivation may be complete or may be partial.

The term "intron" as used herein is defined as a region of a gene transcribed from a DNA template but subsequently removed by splicing together the segments (exons) which flank it.

The term "medical condition" as used herein is defined as a state of health in which at least one physical trait of an organism is abnormal or deficient. In a preferred embodiment the medical condition is a medical condition such as Incontinentia Pigment or the medical condition is the presence of a defect, such as a skin defect.

The term "neurological defects" as used herein is defined as any abnormality or defect associated with the nervous system. The defects may result in mental retardation, hypotonia spasticity, epilepsy and microcephaly.

The term "NF-κB Essential Modulator related" as used herein is defined as any compound, such as a nucleic acid or amino acid, or pathway with which NF-κB Essential Modulator either is or is associated in any manner. This includes any component and the nucleic acid which encodes it that is involved in a complex with NF-κB Essential Modulator.

The term "NF-κB related" as used herein is defined as any compound, such as a nucleic acid or amino acid, or pathway with which NF-κB either is or is associated with in any manner. This includes any component and the nucleic acid which encodes it that is involved in a complex with NF-κB Essential Modulator.

The term "noncarrier individual" as used herein is defined as an individual who does not contain a mutation in a sequence SEQ ID NO:1. In a specific embodiment the individual is homozygous wildtype for SEQ ID NO:1.

The term "nucleic acid chip technology" as used herein is defined as the method of immobilizing nucleic acid on a microchip for subsequent hybridization analysis.

The term "ophthalmologic defect" as used herein is defined as any abnormality or defect related to the eye or eyes including and related diseases. Deficiencies may include dysplasia of retinal vessels, cicatrization and retina folds and tractional detachment.

The term "pharmaceutically acceptable carrier" as used herein is defined as a molecular entity and/or composition that does not produce an adverse, allergic and/or other undesirable reaction when administered to an organism.

The term "polymerase chain reaction" (PCR) is well known in the art and includes the method of amplifying a nucleic acid sequence utilizing two oligonucleotide primers and a thermostable nucleic acid polymerase.

The term "primer," as used herein, is meant to encompass any nucleic acid that is capable of priming the synthesis of a nascent nucleic acid in a template-dependent process.

The term "reverse transcription-polymerase chain reaction" as used herein is defined as the polymerization of a DNA molecule using an RNA molecule as a template for the purpose of utilizing said DNA molecule as a template for PCR.

The term "RNA" as used herein is defined as ribonucleic acid.

The term "splicing" as used herein is defined as a means of removing intron sequences within a primary RNA transcript in processing of said transcript to a mature messenger RNA.

The term "skin defect" as used herein is defined as any abnormality or defect related to the skin or epidermis. Deficiencies may include skin lesions, hyperpigmentation, hypopigmention, atrophy, and absence of the sweat glands or hair follicles.

The term "suicide gene" as used herein is defined as a gene whose gene product is lethal to a cell upon exposure to a prodrug.

The term "therapeutically effective" as used herein is defined as the amount of a compound required to improve some symptom associated with a disease or medical condition. For example, in the treatment of neurodevelopmental disease, a compound which decreases, prevents, delays, or arrests any symptom of the disease would be therapeutically effective. A therapeutically effective amount of a compound is not required to cure a disease but will provide a treatment for a disease.

The term "treatment" as used herein is defined as the management of a patient through medical or surgical means. The treatment improves or alleviates at least one symptom of a medical condition or disease and is not required to provide a cure.

The term 3' untranslated region (3' UTR) as used herein is defined as the sequence at the 3' end of a messenger RNA which does not become translated into protein and can include regulatory sequences and sequences important for posttranscriptional processing.

The term "transcribe" as used herein is defined as the process of generating an RNA transcript molecule using DNA as a template.

The term "transcript" as used herein is defined as an RNA molecule which has been transcribed from DNA.

The term "X-linked inactivation" as used herein is defined as the inactivation through repression of genes located on the X chromosome in somatic cells of female mammals.

It is an object of the present invention to provide a method to detect a NF-κB related medical condition in an organism comprising the step of obtaining a sample in an organism and analyzing the sample for an alteration in a NF-κB Essential Modulator nucleic acid sequence of SEQ ID NO:1, wherein said alteration results in inactivation of NF-κB. The inventors have developed genomic and flanking sequence for the NEMO gene, shown that it is mutated in cases of humans with Incontinentia pigmenti and developed a polymerase chain reaction-based and Southern analysis-based diagnostic tests for mutations in NEMO. It is preferred that the sequence used for screening of patients is the full genomic and flanking sequence, SEQ ID NO:1. The amino acid sequence of NEMO is SEQ ID NO:2, and the cDNA sequence is SEQ ID NO:3.

The examples presented herein illustrate the first evidence of the NF-κB pathway associated with a medical condition. One skilled in the art in light of the present invention is made aware herein of the relationship between a NF-κB related medical condition and an alteration such as a mutation or mutations in a NF-κB Essential Modulator (NEMO) nucleic acid sequence which are responsible for said medical condition. Furthermore, a skilled artisan is aware that the invention addresses a mutation which is deleterious to the function of the NF-κB amino acid sequence. Multiple mutations may be present or may be required to be deleterious. In a specific embodiment the molecular defect is a chromosomal rearrangement as described in the Examples herein. It is within the scope of the present invention to include a sequence of SEQ ID NO:1 which has a mutation that does not affect the function of a polypeptide which it encodes.

A mutation, or alteration, may be any change in a DNA sequence including rearrangement, deletion, insertion, point mutation (substituting one base) or any other kind of unnatural alteration to a nucleic acid. A point mutation can be a nonsense, frameshift, missense or splicing mutations. Deletion herein includes a truncation of the sequence. Alterations herein include additions of a sequence. A mutation can reside in the regulatory sequence of a gene, which can include an enhancer sequence, promoter sequences or cis sequences which bind transacting factors. Mutations in the regulatory sequence may be point mutations, deletion, rearrangement or insertion. Transacting factors for said regulatory sequences may be of a general nature in function or may be specific to said gene. Many types of transacting factors may be associated, including transcriptional factors or repressors. A mutation in the regulatory region of a gene might affect post-transcriptional processing. For example, incorrect capping of the transcript could lead to aberrant subcellular localization. In a specific embodiment, another mutation which might affect regulation of the NEMO gene is through X-linked inactivation in which the normal pattern of repression in transcription of the gene on the X chromosome has been disrupted, either partially or completely. A mutation may also occur in an exon, an intron, an exon/intron junction or a 3' untranslated region (UTR). A mutation occurring in an exon/intron junction could affect either the donor site or the acceptor site, or multiple mutations can affect both and as a result would cause defective splicing of the ribonucleic acid. A skilled artisan would be aware that a deficiency in splicing could cause retention of intronic sequences in the mature messenger RNA allowing translation to proceed into intron sequences, which would likely lead to a nonsense codon which would generate a truncated protein.

A mutation in a 3' UTR could affect regulatory sequences present which could be associated with mRNA degradation, mRNA stability, subcellular localization, post-transcriptional processing or translation. Said mutation could also affect poly-(A) adenylation sites leading to a loss of polyadenylation or ectopic polyadenylation sites. Alternative polyadenylation in the 3' UTR of NEMO results in a variety of transcripts, some of which are differentially expressed in the human brain (D'Esposito, et al., 1996 and Coy et al., 1999). Mutations could affect localization of the different sized transcripts and could lead to aberrant phenotypes.

Mutations of nucleic acid sequence can be nonsense, missense, frameshift, insertion, deletion, rearrangement or a combination thereof of one or more base pairs. Mutations could lead to a truncated protein, could alter the conformation of the protein or could directly affect an amino acid required for function of the protein. An alteration which produces no deleterious effects on the function or structure of the protein and produces no detectable phenotype is not the focus of the present invention.

A skilled artisan is aware that a single polymorphism can alter mRNA folding (Shen et al., 1999), which can affect how it interacts with factors which regulate mRNA processing stability or translation. In a specific embodiment of the present invention a NEMO nucleic acid sequence contains such a mutation.

A mutation or mutations in a NEMO nucleic acid sequence can be detected in a variety of methods known to those in the art including by sequencing, probe, nucleic acid hybridization, PCR, SSCP, heteroduplex analysis, nucleic acid chip hybridization, electrophoresis, or fluorescent in situ hybridization (FISH). Sequencing methods are common laboratory procedures known to many in the art and would be able to detect the exact nature of the mutation. In addition, mutation could be detected by probe. For instance, one skilled in the art would be aware that a fluorescent tag could be specific for binding of a mutation and could be exposed to, for instance, glass beads coated with nucleic acids containing potential mutations. Upon binding of the tag to the mutation in question, a change in fluorescence (such as creation of fluorescence, increase in intensity, or partial or complete quenching) could be indicative of the presence of that mutation. Nucleic acid hybridization including southern or northern could be utilized to detect mutations such as those involved in alteration of large regions of the sequence or of those involved in alteration of a sequence containing a restriction endonuclease site. Hybridization is detected by a variety of ways including radioactivity, color change, light emission, or fluorescence. PCR could also be used to amplify a region suspected to contain a mutation and the resulting amplified region could either be subjected to sequencing or to restriction digestion analysis in the event that mutation was responsible for creating or removing a restriction endonuclease site. The mutation could be identified through an RNA species from the gene by RT-PCR methods which are well known in the art. One skilled in the art would also know that a specific method of nucleic acid hybridization could be utilized in the form of nucleic acid chip hybridization in which nucleic acids are present on a immobilized surface such as a microchip or microchips and are subjected to hybridization techniques sensitive enough to detect minor changes in sequences; a variety of detection methods could be used including light emission, fluorescence, color change, or radioactivity. Electrophoresis could detect mutations of the sequence either by mobility changes or in conjunction with another method of detecting a mutation such as with sequencing or by PCR. Finally, one skilled in the art would be aware that FISH is a proficient technique of detecting large regions of sequences on chromosomes which have been deleted or rearranged.

In a specific embodiment there is a method to detect a mutation in a nucleic acid. As described in Ropp and Thorp, 1999, a modified base 8-oxoguanine undergoes oxidation at different rates depending on which base it pairs with. Thus, a skilled artisan is aware that minute differences in sequence among DNA strands may be detected using electrochemical techniques. In a specific embodiment the described method is performed in microtiter plates and can screen multiple samples for a single nucleotide polymorphism.

Nucleic Acid Detection

In addition to their use in directing the expression of NEMO proteins, polypeptides and/or peptides, the nucleic acid sequences disclosed herein have a variety of other uses. For example, they have utility as probes or primers for embodiments involving nucleic acid hybridization or polymerization.

Hybridization

The use of a probe or primer of between 13 and 100 nucleotides, preferably between 17 and 100 nucleotides in length, or in some aspects of the invention up to 1–2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

Accordingly, the nucleotide sequences of the invention may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

For certain applications, for example, site-directed mutagenesis, it is appreciated that lower stringency conditions are preferred. Under these conditions, hybridization may occur even though the sequences of the hybridizing strands are not perfectly complementary, but are mismatched at one or more positions. Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples.

In general, it is envisioned that the probes or primers described herein will be useful for detection of mutations in NEMO, as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919, 626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

Amplification of Nucleic Acids

Nucleic acids used as a template for amplification may be isolated from cells, tissues or other samples according to standard methodologies (Sambrook et al., 1989). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process.

Typically, primers are oligonucleotides from about ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to NEMO are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Affymax technology; Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1990, each of which is incorporated herein by reference in their entirety.

A reverse transcriptase PCR™ amplification procedure may be performed to quantify the amount of mRNA amplified. Methods of reverse transcribing RNA into cDNA are well known and described in Sambrook et al., 1989. Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assy (OLA), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). Davey et al., European Application No. 329 822 disclose a nucleic acid amplification process involving cyclically synthesizing single-stranded RNA ("ssRNA"), ssDNA, and double-stranded DNA (dsDNA), which may be used in accordance with the present invention.

Miller et al., PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR" (Frohman, 1990; Ohara et al., 1989).

Detection of Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 1989). Separated amplification products may be cut out and eluted from the gel for further manipulation. Using low melting point agarose gels, the separated band may be removed by heating the gel, followed by extraction of the nucleic acid.

Separation of nucleic acids may also be effected by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art. See Sambrook et al., 1989. One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

Other Assays

Other methods for genetic screening may be used within the scope of the present invention, for example, to detect mutations in genomic DNA, cDNA and/or RNA samples. Methods used to detect point mutations include denaturing gradient gel electrophoresis ("DGGE"), restriction fragment length polymorphism analysis ("RFLP"), chemical or enzymatic cleavage methods, direct sequencing of target regions amplified by PCR™ (see above), single-strand conformation polymorphism analysis ("SSCP") and other methods well known in the art.

One method of screening for point mutations is based on RNase cleavage of base pair mismatches in RNA/DNA or RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single or multiple base point mutations.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

Other investigators have described the use of RNase I in mismatch assays. The use of RNase I for mismatch detection is described in literature from Promega Biotech. Promega markets a kit containing RNase I that is reported to cleave three out of four known mismatches. Others have described using the MutS protein or other DNA-repair enzymes for detection of single-base mismatches.

Alternative methods for detection of deletion, insertion or substitution mutations that may be used in the practice of the present invention are disclosed in U.S. Pat. Nos. 5,849,483, 5,851,770, 5,866,337, 5,925,525 and 5,928,870, each of which is incorporated herein by reference in its entirety.

Kits

All the essential materials and/or reagents required for detecting NEMO in a sample may be assembled together in a kit. This generally will comprise a probe or primers designed to hybridize specifically to individual nucleic acids of interest in the practice of the present invention, including NEMO. Also included may be enzymes suitable for amplifying nucleic acids, including various polymerases (reverse transcriptase, Taq, etc.), deoxynucleotides and buffers to provide the necessary reaction mixture for amplification.

Such kits may also include enzymes and other reagents suitable for detection of specific nucleic acids or amplification products. Such kits generally will comprise, in suitable means, distinct containers for each individual reagent or enzyme as well as for each probe or primer pair.

Nucleic Acid Based Expression Systems

Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Maniatis et al., 1988 and Ausubel et al., 1994, both incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202, 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

The identity of tissue-specific promoters or elements, as well as assays to characterize their activity, is well known to those of skill in the art. Examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), D1A dopamine receptor gene (Lee, et al., 1997), insulin-like growth factor II (Wu et al., 1997), human platelet endothelial cell adhesion molecule-1 (Almendro et al., 1996).

Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/ enhancer to transcribe a single message (see U.S. Pat. Nos. 5,925,565 and 5,935,819, herein incorporated by reference).

Multiple Cloning Sites

Vectors can include a multiple cloning site (MCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al., 1997, herein incorporated by reference.)

Polyadenylation Signals

In expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Also contemplated as an element of the expression cassette is a transcriptional termination site. These elements can serve to enhance message levels and/or to minimize read through from the cassette into other sequences.

Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

Selectable and Screenable Markers

In certain embodiments of the invention, the cells contain nucleic acid construct of the present invention, a cell may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

Host Cells

As used herein, the terms "cell," "cell line," and "cell culture" may be used interchangeably. All of these term also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

Host cells may be derived from prokaryotes or eukaryotes, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla). Alternatively, bacterial cells such as *E. coli* LE392 could be used as host cells for phage viruses.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

Other examples of expression systems include STRATAGENE®'s COMPLETE CONTROL™ Inducible Mammalian Expression System, which involves a synthetic ecdysone-inducible receptor, or its pET Expression System, an E. coli expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the Pichia methanolica Expression System, which is designed for high-level production of recombinant proteins in the methylotrophic yeast Pichia methanolica. One of skill in the art would know how to express a vector, such as an expression construct, to produce a nucleic acid sequence or its cognate polypeptide, protein, or peptide.

In another object of the present invention there is a method to detect a NF-κB related medical condition in an organism comprising the steps of obtaining a sample from the organism, and analyzing the sample for an alteration in SEQ ID NO:2, wherein said alteration results in inactivation of NF-κB. One skilled in the art is aware that alterations can be detected in the NEMO protein through the following methods: sequencing, mass spectrometry, by molecular weight or with antibodies. Examples of alterations include a change, loss, or addition of an amino acid, truncation or fragmentation of the protein. Alterations can increase degradation of the protein, can change conformation of the protein, or can be present in a hydrophobic or hydrophilic domain of the protein. The alteration need not be in an active site of the protein to have a deleterious effect on its function or structure, or both. Alteration can include modifications to the protein such as phosphorylation, myristilation, acetylation, or methylation. Sequencing of the protein or a fragment thereof directly by methods well known in the art would identify specific amino acid alterations. Alterations in protein sequences can be detected by analyzing either the entire protein or fragments of the protein and subjecting them to mass spectrometry, which would be able to detect even minor changes in molecular weight. Additionally, antibodies can be used to detect mutations in said proteins if the epitope includes the particular site which has been mutated. Antibodies can be used to detect mutations in the amino acid sequence by immunoblotting, with in situ methods, or by immunoprecipitation. Antibodies to a NEMO amino acid sequence on immunoblots may alternatively recognize any epitope of the amino acid sequence and could detect truncations or modifications of the protein which would affect electrophoretic mobility, including phosphorylation or myristilation. Another method of identifying a mutation in a NEMO amino acid sequence is through the analysis of its subcellular localization. A sequence of SEQ ID NO:2 which contains an alteration that does not alter the function of the amino acid sequence is within the scope of the present invention.

The presence of a mutation in a NEMO amino acid sequence may be inferred by the phenotype(s) which occurs either directly or indirectly as a result of such a mutation. A skilled artisan is aware that ideally a routine method for detection of a mutation in a nucleic acid or an alteration of an amino acid in a NF-κB related medical condition would preferably be rapid, repeatable and/or easy to perform.

It is another object of the present invention to provide a method to treat an organism with an NF-κB related medical condition comprising the step of administering to said organism a NF-κB Essential Modulator nucleic acid sequence of SEQ ID NO:1. It is within the scope of the present invention to include multiple administrations of a sequence of SEQ ID NO:1 to treat the medical condition. In a specific embodiment the vector is selected from the group consisting of a nucleic acid, an amino acid sequence, a lipid, a liposome, a carbohydrate, a sugar, and a combination thereof.

It is another object of the present invention to provide a method to treat an organism with an NF-κB related medical condition comprising the step of administering to said organism a NF-κB Essential Modulator amino acid sequence of SEQ ID NO:2. It is within the scope of the present invention to include multiple administrations of a sequence of SEQ ID NO:2 to treat the medical condition.

It is yet another object of the present invention to provide a method to treat an apoptosis-related medical condition comprising the step of administering to said organism a NF-κB Essential Modulator amino acid sequence of SEQ ID NO:2. During development in an organism and particularly in an organ, such as an eye or the brain, cells migrate in the developing embryo and eventually become no longer necessary. At this point, apoptosis occurs in these cells. However, there are many different medical conditions in which apoptosis is related to the mechanism of the medical condition, such as when apoptosis occurs during a premature state of development or occurs in an ectopic region. Alternatively, apoptosis may occur at a later than normal time in development or not at all. A skilled artisan is taught by the present invention that there is a method of administering a NF-κB Essential Modulator nucleic acid or amino acid sequence to an organism which has such an apoptosis defect. Apoptosis defects in an organism with Incontinentia Pigmenti can lead to defects in the retina or the brain.

It is an additional object of the present invention to provide a method to treat an organism with a neurological defect comprising the step of administering to said organism a NF-κB Essential Modulator nucleic acid sequence of SEQ ID NO:1 or an amino acid sequence of SEQ ID NO:2. Malformations of the brain can lead to seizure disorders. Some disorders that create seizures in an infant are related to failure of the brain to form normally due to a defect in the NF-κB pathway or a failure of cells to regress due to the pathway defect. Neural migratory defects may occur in a NF-κB related medical condition. Nerve cells normally form and migrate, upon which newer layers of cells migrate through older layers of cells. The medical condition may be related to failure of the newer cells to migrate or related to the failure of the older cells to regress or to vascular occlusions or obliterations. Microcephaly may be present as the result of small brain development, which is related to nerve development and migration. A medical condition may be related both to apoptosis and a neurological defect, such as has been recently reported regarding motor neuron death through caspase-mediated apoptosis (Li et al., 2000). Thus, the methods of the present invention are directed to treatments for neurological defects associated with a loss of activation of NF-κB comprising the step of administering to an organism a NF-κB Essential Modulator nucleic acid sequence of SEQ ID NO:1 or an amino acid sequence of SEQ ID NO:2.

It is an additional object of the present invention to provide a method to treat an organism with an ophthalmological defect comprising the step of administering to said organism a NF-κB Essential Modulator nucleic acid sequence of SEQ ID NO:1 or an amino acid sequence of SEQ ID NO:2. In the retina, defects may be related to proliferation of blood vessels, which is deleterious to sight. In an embodiment of the present invention there is a treatment for this overgrowth by correcting or improving for aberrant activation of NF-κB. An example of a retinal medical condition which is associated with defects of the NF-κB pathway is retinopathy of prematurity. Proliferative vasculopathies (abnormal proliferation of blood vessels of the retina) are defective in such a medical condition. During growth of the embryo blood vessels develop and grow, cells migrate and proliferate. In the third trimester this becomes disrupted because upon birth, infants with this medical condition have not developed completely mature retinas. The defect in a medical condition associated with NF-κB activation may be associated with cataracts, small eye, or may be the result of retinal detachment, all of which may be related to massive overgrowth of blood vessels due to loss of activation of the NF-κB pathway. Thus, the methods of the present invention are directed to alleviating such a condition by providing treatment by administering a NF-κB Essential Modulator nucleic acid sequence of SEQ ID NO:1 or an amino acid sequence of SEQ ID NO:2.

It is an additional object of the present invention to provide a method to treat an organism with an immune system defect comprising the step of administering to said organism a NF-κB Essential Modulator nucleic acid sequence of SEQ ID NO:1 or an amino acid sequence of SEQ ID NO:2. As taught herein, the loss of a functional NF-κB pathway results in immune system related medical conditions. For instance, organisms have a completely or partially impaired capability to fight infectious medical conditions such as bacterial infections. In patients with a NF-κB related medical condition such as Incontinentia Pigmenti, there is an extreme proliferation of eosinophils (specialized white blood cells) which become infiltrated in the skin and increase to significant levels in the blood (for example, from 1–2% to 35–45% in infants affected with Incontinentia Pigmenti). This suggests this pathway is associated with allergic or immune systems in an organism with a characteristic, being the trigger or release of an event related to a significant deleterious change in the immune/protection system of bone marrow.

It is an additional object of the present invention to provide a method to treat an organism with a blood vessel medical condition comprising the step of administering to said organism a NF-κB Essential Modulator nucleic acid sequence of SEQ ID NO:1 or an amino acid sequence of SEQ ID NO:2. As taught herein, the loss of a functional NF-κB pathway results in alterations in blood vessels. In an embodiment of the present invention the blood vessel defects are associated with the retina, the brain or skin. Organisms with defects in blood vessels of the brain not only affect nervous tissue, but strokes may develop in these patients.

In another object of the present invention there is a method to treat an organism with a dental defect comprising the step of administering to said organism a NF-κB Essential Modulator nucleic acid sequence of SEQ ID NO:1 or an amino acid sequence of SEQ ID NO:2. As taught herein, the loss of a functional NF-κB pathway results in dental defects. Organisms may be missing teeth, have soft teeth, abnormally shaped teeth, widely spaced teeth or an abnormal number of teeth.

In another object of the present invention there is a method to treat an organism with osteopetrosis comprising the step of administering to said organism a NF-κB Essential Modulator nucleic acid sequence of SEQ ID NO:1 or an amino acid sequence of SEQ ID NO:2. As taught herein, the loss of a functional NF-κB pathway results in defective bone development. Osteopetrosis results from defective resorption of immature bone. Osteosclerosis, sometimes termed osteopetrosis, is a feature of pycnodysostosis.

In another object of the present invention there is a method to treat an organism with a skin defect comprising the step of administering to said organism a NF-κB Essential Modulator nucleic acid sequence of SEQ ID NO:1 or an amino acid sequence of SEQ ID NO:2. As taught herein, the loss of a functional NF-κB pathway results in skin defects, such as linear and reticular skin changes described elsewhere herein. An organism may exhibit hypomelanosis of Ito, although some features are similar to those of classic Incontinentia Pigmenti, the differences are sufficient to establish it as a separate disorder. The disorder is characterized by unilateral or bilateral macular hypopigmented whorls, streaks, and patches which are described as the 'negative pattern' of the hyperpigmented lesions of Incontinentia Pigmenti. Abnormalities of the eyes and the musculoskeletal and central nervous systems occur in some (Jelinek et al., 1973). Neurologic impairment can be quite severe with hemimegalencephaly and/or migration disorders. Fujino et al. (1995) presented neuropathologic findings of a severely affected Japanese girl who succumbed at 13 months. There was brachycephaly and micropolygyria with disarrayed cortical lamination with nerve cells in the white matter demonstrable histologically, suggesting a migration defect during maturation. Ogino et al. (1994) presented neurophysiologic studies in 3 affected children that illustrated great variability of central nervous system involvement. One patient presented with the West syndrome and had an asymmetric hypsarrhythmia. The second patient had only mild mental retardation and minimal EEG abnormalities, whereas the third patient was neurologically normal.

It is an object of the present invention to provide a method to prevent a NF-κB related medical condition in an organism, comprising the step of administering to the organism a nucleic acid sequence of SEQ ID NO:1. In a preferred embodiment of the present invention, the administration occurs in utero by methods well known to one of skill in the art. It is an object of the present invention to provide a method to prevent a NF-κB related medical condition in an organism, comprising the step of administering to the organism a nucleic acid sequence of SEQ ID NO:2. In a preferred embodiment of the present invention, the administration occurs in utero by methods well known to one of skill in the art.

It is an object of the present invention to provide a method to screen an organism for a compound for the treatment of a NF-κB related medical condition, wherein said organism has an alteration in a sequence of SEQ ID NO:1, wherein said alteration results in inactivation of NF-κB comprising the step of administering said compound to said organism and assaying for an improvement in said NF-κB related medical condition. It is an object of the present invention to provide a method to screen an organism for a compound for the treatment of a NF-κB related medical condition, wherein said organism has an alteration in a sequence of SEQ ID NO:2, wherein said alteration results in inactivation of NF-κB comprising the step of administering said compound to said organism and assaying for an improvement in said NF-κB related medical condition. In a preferred embodiment the medical condition is Incontinentia Pigmenti. An improvement of the medical condition is herein defined as the bringing to a better state of at least one symptom of the medical condition.

It is an object of the present invention to provide a compound for the treatment of a NF-κB related medical condition in an organism, such as Incontinentia Pigmenti, comprising a NF-κB Essential Modulator nucleic acid sequence of SEQ ID NO:1 or a NF-κB Essential Modulator amino acid sequence of SEQ ID NO:2.

In another embodiment of the present invention there is a method to screen an organism for a compound for the treatment of a NF-κB related medical condition, wherein said organism has an alteration in a sequence of SEQ ID NO:1, wherein said alteration results in inactivation of NF-κB, comprising the step of administering said compound to said organism and assaying for an improvement in said NF-κB related medical condition.

It is an object of the present invention to provide a composition for the treatment of a NF-κB related medical condition in an organism comprising a therapeutically effective amount of a NF-κB Essential Modulator nucleic acid sequence of SEQ ID NO:1 or a NF-κB Essential Modulator amino acid sequence of SEQ ID NO:2, and a pharmaceutically acceptable carrier. In a specific object the NF-κB related medical condition is Incontinentia Pigmenti.

Dosage and Formulation

The compounds (active ingredients) of this invention can be formulated and administered to treat a NF-κB related medical condition by any means that produces contact of the active ingredient with the agent's site of action in the body of a vertebrate. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

The dosage administered will be a therapeutically effective amount of active ingredient and will, of course, vary depending upon known factors such as the pharmacodynamic characteristics of the particular active ingredient and its mode and route of administration; age, sex, health and weight of the recipient; nature and extent of symptoms; kind of concurrent treatment, frequency of treatment and the effect desired. It is preferred to have the active ingredient, regardless of its nature, to be stable. Multiple administrations of a sequence of SEQ ID NO:1 or SEQ ID NO:2 are within the scope of the present invention and are a specific embodiment.

The active ingredient can be administered orally in solid dosage forms such as capsules, tablets and powders, or in liquid dosage forms such as elixirs, syrups, emulsions and suspensions. The active ingredient can also be formulated for administration parenterally by injection, rapid infusion, nasopharyngeal absorption or dermoabsorption. The agent may be administered intramuscularly, intravenously, subcutaneously, transdermally or as a suppository.

Gelatin capsules contain the active ingredient and powdered carriers such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium Ethylenediaminetetraacetic acid (EDTA). In addition, parenteral solutions can contain preservatives such as benzalkonium chloride, methyl- or propyl-paraben and chlorobutanol. Suitable pharmaceutical carriers are described in Remington's Pharmaceutical Sciences, a standard reference text in this field.

Additionally, standard pharmaceutical methods can be employed to control the duration of action. These are well known in the art and include control release preparations and can include appropriate macromolecules, for example polymers, polyesters, polyamino acids, polyvinyl, pyrolidone, ethylenevinylacetate, methyl cellulose, carboxymethyl cellulose or protamine sulfate. The concentration of macromolecules as well as the methods of incorporation can be adjusted in order to control release. Additionally, the agent can be incorporated into particles of polymeric materials such as polyesters, polyamino acids, hydrogels, poly (lactic acid) or ethylenevinylacetate copolymers. In addition to being incorporated, these agents can also be used to trap the compound in microcapsules.

Useful pharmaceutical dosage forms for administration of the compounds of this invention can be illustrated as follows. Pharmacological ranges for the active ingredients can be determined by the skilled artisan using methods well known in the art.

Capsules: Capsules are prepared by filling standard two-piece hard gelatin capsulates each with powdered active ingredient, 175 milligrams of lactose, 24 milligrams of talc and 6 milligrams magnesium stearate.

Soft Gelatin Capsules: A mixture of active ingredient in soybean oil is prepared and injected by means of a positive displacement pump into gelatin to form soft gelatin capsules containing the active ingredient. The capsules are then washed and dried.

Tablets: Tablets are prepared by conventional procedures so that the dosage unit contains the suggested amount of active ingredient, 0.2 milligrams of colloidal silicon dioxide, 5 milligrams of magnesium stearate, 275 milligrams of microcrystalline cellulose, 11 milligrams of cornstarch and 98.8 milligrams of lactose. Appropriate coatings may be applied to increase palatability or to delay absorption.

Injectable: A parenteral composition suitable for administration by injection is prepared by stirring 1.5% by weight of active ingredients in 10% by volume propylene glycol and water. The solution is made isotonic with sodium chloride and sterilized.

Suspension: An aqueous suspension is prepared for oral administration so that each 5 millileters contains the suggested amount of finely divided active ingredient, 200 milligrams of sodium carboxymethyl cellulose, 5 milligrams of sodium benzoate, 1.0 grams of sorbitol solution U.S.P. and 0.025 millileters of vanillin.

Accordingly, the pharmaceutical composition of the present invention may be delivered via various routes and to various sites in an animal body to achieve a particular effect. One skilled in the art will recognize that although more than one route can be used for administration, a particular route can provide a more immediate and more effective reaction than another route. Local or systemic delivery can be accomplished by administration comprising application or instillation of the formulation into body cavities, inhalation or insufflation of an aerosol, or by parenteral introduction, comprising intramuscular, intravenous, peritoneal, subcutaneous, intradermal, as well as topical administration.

The composition of the present invention can be provided in unit dosage form wherein each dosage unit, e.g., a teaspoonful, tablet, solution, or suppository, contains a predetermined amount of the composition, alone or in appropriate combination with other active agents. The term "unit dosage form" as used herein refers to physically discrete units suitable as unitary dosages for human and animal subjects, each unit containing a predetermined quantity of the compositions of the present invention, alone or in combination with other active agents, calculated in an amount sufficient to produce the desired effect, in association with a pharmaceutically acceptable diluent, carrier, or vehicle, where appropriate. The specifications for the unit dosage forms of the present invention depend on the particular effect to be achieved and the particular pharmacodynamics associated with the pharmaceutical composition in the particular host.

These methods described herein are by no means all-inclusive, and further methods to suit the specific application will be apparent to the ordinary skilled artisan. Moreover, the effective amount of the compositions can be further approximated through analogy to compounds known to exert the desired effect.

In a specific embodiment a drug may be transported to a target by utilizing carbonic anhydrase inhibitor (CAI) which contains a polar group such as a carboxyl group, as described in Kehayova et al., 1999. The carboxyl group renders the composition dissolvable in water, however, upon exposure to light the bond linking the CAI to the carboxyl mask breaks, allowing the remaining portion to be soluble in a hydrophobic environment.

In certain embodiments, the use of lipid formulations and/or nanocapsules is contemplated for the introduction of a NF-κB Essential Modulator nucleic acid, polypeptides, peptides and/or agents, and/or gene therapy vectors, including both wild-type and/or antisense vectors, into host cells.

Nanocapsules can generally entrap compounds in a stable and/or reproducible way. To avoid side effects due to intracellular polymeric overloading, such ultrafine particles (sized around 0.1 μm) should be designed using polymers able to be degraded in vivo. Biodegradable polyalkylcyanoacrylate nanoparticles that meet these requirements are contemplated for use in the present invention, and/or such particles may be easily made.

In a preferred embodiment of the invention, the pharmaceutical composition may be associated with a lipid. The pharmaceutical composition associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. The lipid or lipid/pharmaceutical composition associated compositions of the present invention are not limited to any particular structure in solution. For example, they may be present in a bilayer structure, as micelles, or with a "collapsed" structure. They may also simply be interspersed in a solution, possibly forming aggregates which are not uniform in either size or shape.

Lipids are fatty substances which may be naturally occurring or synthetic lipids. For example, lipids include the fatty droplets that naturally occur in the cytoplasm as well as the class of compounds which are well known to those of skill in the art which contain long-chain aliphatic hydrocarbons and their derivatives, such as fatty acids, alcohols, amines, amino alcohols, and aldehydes.

Phospholipids may be used for preparing the liposomes according to the present invention and may carry a net positive, negative, or neutral charge. Diacetyl phosphate can be employed to confer a negative charge on the liposomes, and stearylamine can be used to confer a positive charge on the liposomes. The liposomes can be made of one or more phospholipids.

A neutrally charged lipid can comprise a lipid with no charge, a substantially uncharged lipid, or a lipid mixture with equal number of positive and negative charges. Suitable phospholipids include phosphatidyl cholines and others that are well known to those of skill in the art.

Lipids suitable for use according to the present invention can be obtained from commercial sources. For example, dimyristyl phosphatidylcholine ("DMPC") can be obtained from Sigma Chemical Co., dicetyl phosphate ("DCP") is obtained from K & K Laboratories (Plainview, N.Y.); cholesterol ("Chol") is obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about –20° C. Preferably, chloroform is used as the only solvent since it is more readily evaporated than methanol.

Phospholipids from natural sources, such as egg or soybean phosphatidylcholine, brain phosphatidic acid, brain or plant phosphatidylinositol, heart cardiolipin and plant or bacterial phosphatidylethanolamine are preferably not used as the primary phosphatide, i.e., constituting 50% or more of the total phosphatide composition, because of the instability and leakiness of the resulting liposomes.

"Liposome" is a generic term encompassing a variety of single and multilamellar lipid vehicles formed by the generation of enclosed lipid bilayers or aggregates. Liposomes may be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). However, the present invention also encompasses compositions that have different structures in solution than the normal vesicular structure. For example, the lipids may assume a micellar structure or merely exist as nonuniform aggregates of lipid molecules. Also contemplated are lipofectamine-nucleic acid complexes.

Phospholipids can form a variety of structures other than liposomes when dispersed in water, depending on the molar ratio of lipid to water. At low ratios the liposome is the preferred structure. The physical characteristics of liposomes depend on pH, ionic strength and/or the presence of divalent cations. Liposomes can show low permeability to ionic and/or polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and/or results in an increase in permeability to ions, sugars and/or drugs.

Liposomes interact with cells via four different mechanisms: Endocytosis by phagocytic cells of the reticuloendothelial system such as macrophages and/or neutrophils; adsorption to the cell surface, either by nonspecific weak hydrophobic and/or electrostatic forces, and/or by specific interactions with cell-surface components; fusion with the plasma cell membrane by insertion of the lipid bilayer of the liposome into the plasma membrane, with simultaneous release of liposomal contents into the cytoplasm; and/or by transfer of liposomal lipids to cellular and/or subcellular membranes, and/or vice versa, without any association of the liposome contents. Varying the liposome formulation can alter which mechanism is operative, although more than one may operate at the same time.

Liposome-mediated oligonucleotide delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments of the invention, the lipid may be associated with a hemagglutinating virus (HVJ). This has been shown to facilitate fusion with the cell membrane and promote cell entry of liposome-encapsulated DNA (Kaneda et al., 1989). In other embodiments, the lipid may be complexed or employed in conjunction with nuclear non-histone chromosomal proteins (HMG-1) (Kato et al., 1991). In yet further embodiments, the lipid may be complexed or employed in conjunction with both HVJ and HMG-1. In that such expression vectors have been successfully employed in transfer and expression of an oligonucleotide in vitro and in vivo, then they are applicable for the present invention. Where a bacterial promoter is employed in the DNA construct, it also will be desirable to include within the liposome an appropriate bacterial polymerase.

Liposomes used according to the present invention can be made by different methods. The size of the liposomes varies depending on the method of synthesis. A liposome suspended in an aqueous solution is generally in the shape of a spherical vesicle, having one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules may form a bilayer, known as a lamella, of the arrangement XY-YX. Aggregates of lipids may form when the hydrophilic and hydrophobic parts of more than one lipid molecule become associated with each other. The size and shape of these aggregates will depend upon many different variables, such as the nature of the solvent and the presence of other compounds in the solution.

Liposomes within the scope of the present invention can be prepared in accordance with known laboratory techniques. In one preferred embodiment, liposomes are prepared by mixing liposomal lipids, in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min. to 2 hours, depending on the desired volume of the liposomes. The composition can be dried further in a desiccator under vacuum. The dried lipids generally are discarded after about 1 week because of a tendency to deteriorate with time.

Dried lipids can be hydrated at approximately 25–50 mM phospholipid in sterile, pyrogen-free water by shaking until all the lipid film is resuspended. The aqueous liposomes can be then separated into aliquots, each placed in a vial, lyophilized and sealed under vacuum.

In the alternative, liposomes can be prepared in accordance with other known laboratory procedures: the method of Bangham et al. (1965), the contents of which are incorporated herein by reference; the method of Gregoriadis, as described in *DRUG CARRIERS IN BIOLOGY AND MEDICINE*, G. Gregoriadis ed. (1979) pp. 287–341, the contents of which are incorporated herein by reference; the method of Deamer and Uster (1983), the contents of which are incorporated by reference; and the reverse-phase evaporation method as described by Szoka and Papahadjopoulos (1978). The aforementioned methods differ in their respective abilities to entrap aqueous material and their respective aqueous space-to-lipid ratios.

The dried lipids or lyophilized liposomes prepared as described above may be dehydrated and reconstituted in a solution of inhibitory peptide and diluted to an appropriate concentration with an suitable solvent, e.g., DPBS. The mixture is then vigorously shaken in a vortex mixer. Unencapsulated nucleic acid is removed by centrifugation at 29,000×g and the liposomal pellets washed. The washed liposomes are resuspended at an appropriate total phospholipid concentration, e.g., about 50–200 mM. The amount of nucleic acid encapsulated can be determined in accordance with standard methods. After determination of the amount of nucleic acid encapsulated in the liposome preparation, the liposomes may be diluted to appropriate concentrations and stored at 4° C. until use.

A pharmaceutical composition comprising the liposomes will usually include a sterile, pharmaceutically acceptable carrier or diluent, such as water or saline solution.

Gene Therapy Administration

For gene therapy, a skilled artisan would be cognizant that the vector to be utilized must contain the gene of interest operatively limited to a promoter. For antisense gene therapy, the antisense sequence of the gene of interest would be operatively linked to a promoter. One skilled in the art recognizes that in certain instances other sequences such as a 3' UTR regulatory sequences are useful in expressing the gene of interest. Where appropriate, the gene therapy vectors can be formulated into preparations in solid, semisolid, liquid or gaseous forms in the ways known in the art for their respective route of administration. Means known in the art can be utilized to prevent release and absorption of the composition until it reaches the target organ or to ensure timed-release of the composition. A pharmaceutically acceptable form should be employed which does not ineffectuate the compositions of the present invention. In pharmaceutical dosage forms, the compositions can be used alone or in appropriate association, as well as in combination, with other pharmaceutically active compounds. A sufficient amount of vector containing the therapeutic nucleic acid sequence must be administered to provide a pharmacologically effective dose of the gene product.

One skilled in the art recognizes that different methods of delivery may be utilized to administer a vector into a cell. Examples include: (1) methods utilizing physical means, such as electroporation (electricity), a gene gun (physical force) or applying large volumes of a liquid (pressure); and (2) methods wherein said vector is complexed to another entity, such as a liposome or transporter molecule.

Accordingly, the present invention provides a method of transferring a therapeutic gene to a host, which comprises administering the vector of the present invention, preferably as part of a composition, using any of the aforementioned routes of administration or alternative routes known to those skilled in the art and appropriate for a particular application. Effective gene transfer of a vector to a host cell in accordance with the present invention to a host cell can be monitored in terms of a therapeutic effect (e.g. alleviation of some symptom associated with the particular disease being treated) or, further, by evidence of the transferred gene or expression of the gene within the host (e.g., using the polymerase chain reaction in conjunction with sequencing, Northern or Southern hybridizations, or transcription assays to detect the nucleic acid in host cells, or using immunoblot analysis, antibody-mediated detection, mRNA or protein half-life studies, or particularized assays to detect protein or polypeptide encoded by the transferred nucleic acid, or impacted in level or function due to such transfer).

These methods described herein are by no means all-inclusive, and further methods to suit the specific application will be apparent to the ordinary skilled artisan. Moreover, the effective amount of the compositions can be further approximated through analogy to compounds known to exert the desired effect.

Furthermore, the actual dose and schedule can vary depending on whether the compositions are administered in combination with other pharmaceutical compositions, or depending on interindividual differences in pharmacokinetics, drug disposition, and metabolism. Similarly, amounts can vary in in vitro applications depending on the particular cell line utilized (e.g., based on the number of vector receptors present on the cell surface, or the ability of the particular vector employed for gene transfer to replicate in that cell line). Furthermore, the amount of vector to be added per cell will likely vary with the length and stability of the therapeutic gene inserted in the vector, as well as also the nature of the sequence, and is particularly a parameter which needs to be determined empirically, and can be altered due to factors not inherent to the methods of the present invention (for instance, the cost associated with synthesis). One skilled in the art can easily make any necessary adjustments in accordance with the exigencies of the particular situation.

It is possible that cells containing the therapeutic gene may also contain a suicide gene (i.e., a gene which encodes a product that can be used to destroy the cell, such as herpes simplex virus thymidine kinase). In many gene therapy situations, it is desirable to be able to express a gene for therapeutic purposes in a host cell but also to have the capacity to destroy the host cell once the therapy is completed, becomes uncontrollable, or does not lead to a predictable or desirable result. Thus, expression of the therapeutic gene in a host cell can be driven by a promoter although the product of said suicide gene remains harmless in the absence of a prodrug. Once the therapy is complete or no longer desired or needed, administration of a prodrug causes the suicide gene product to become lethal to the cell. Examples of suicide gene/prodrug combinations which may be used are Herpes Simplex Virus-thymidine kinase (HSV-tk) and ganciclovir, acyclovir or FIAU; oxidoreductase and cycloheximide; cytosine deaminase and 5-fluorocytosine; thymidine kinase thymidilate kinase (Tdk::Tmk) and AZT; and deoxycytidine kinase and cytosine arabinoside.

The method of cell therapy may be employed by methods known in the art wherein a cultured cell containing a non-defective copy of a gene encoding a NEMO amino acid is introduced.

In a specific embodiment the transfection of nucleic acid is facilitated by a transport protein, as described in Subramanian, et al., 1999. Briefly, a peptide M0 is chemically bound to a cationic peptide as a carrier molecule. The cationic complex binds the negatively charged nucleic acid of interest, followed by binding of M9 to a nuclear transport protein, such as transportin.

In another embodiment, biologically active molecules, such as vectors for gene therapy, are incorporated in a large hydration domain between "pinched" regions of a lipid-poly-L-glutamic acid (PGA) complex, where the PGA and the cationic lipid didodecyl dimethylammonium bromide assotiate to form localized pinched regions, for delivery applications (Subramaniam, et al., 2000).

In an alternative embodiment, an amino acid sequence is engineered to accumulate as an aggregate in the endoplasmic reticulum, followed by administration of a composition to induce protein disaggregation, resulting in rapid and transient secretion (Rivera et al., 2000).

One skilled in the art is taught by the present invention that methods to screen for mutations in a NF-κB Essential Modulator amino acid sequence of SEQ ID NO:2 in an NF-κB related medical condition and methods to treat said medical condition may be appropriate regardless of whether the consequences of the mutation are direct or indirect. That is, the mutation may produce a phenotype which is a direct cause of the disease or the mutation may indirectly affect a disease state through a secondary gene or gene product. In either case, the methods to screen and the methods to treat as claimed are applicable.

In a specific embodiment the gene therapy administration occurs prenatally, immediately postnatally or postnatally.

A peptide (11 amino acids) derived from HIV has been recently described that when fused to full length proteins and injected into mice allow a rapid dispersal to the nucleus of all cells of the body (Schwarze et al., 1999). Schwarze et al. made fusion proteins to Tat ranging in size from 15 to 120 kDa. They documented a rapid uptake of the fusion proteins to the nuclei of cells throughout the animal, and the functional activity of said proteins was retained.

In an embodiment of the present invention there are constructs containing the Tat or Tat-HA nucleic acid sequence operatively linked to a NEMO nucleic acid sequence. The vectors are expressed in bacterial cultures and the fusion protein is purified. This purified Tat-NEMO protein or Tat-NEMO protein is injected into animal to determine the efficiency of the Tat delivery system into the site of inflammation, the joints, or by means to deliver the fusion protein systemically. Analysis is carried out to determine the potential of the Tat-NEMO protein in reduction of inflammation or alleviation of any arthritis symptom. This is a viable therapeutic approach either in its own right or in association with other methods, treatments or genes.

The following examples are offered by way of example and are not intended to limit the scope of the invention in any manner.

EXAMPLE 1

Analysis of cDNA from Fibroblast Lines Indicates that Mutations in NEMO Cause IP The extreme skewing of X-inactivation observed for the majority of IP cases has implications for screening of candidate genes. cDNA prepared from IP females will not contain the mutated allele of the disease locus and therefore candidate gene screening is most often performed by PCR of genomic DNA. To expedite screening of NEMO, therefore, two approaches were employed simultaneously; a) generation and sequencing of cDNA from rare male and female fibroblast lines that express only the mutated X-chromosome; and b) resolution of the NEMO genomic structure for screening of individual exons.

Reverse transcriptase polymerase chain reaction (RT-PCR) from mRNAs derived from skin fibroblasts of four affected fetuses (D, K IP85 and G) was conducted with NEMO-specific primers (FIG. 1A). Male samples D and IP85m as well as female sample K express only a mutated (IP) X chromosome. Affected female G expresses both X's. RNAs extracted from adult and fetus skin fibroblasts were used as controls (C1 and C2). Amplification between primers mapping to NEMO exons 2 and 3 (exon organization as described below in FIG. 2) for fetuses K, D, G (FIGS. 1A, 1B, 1C) produced an RT-PCR product corresponding to the 5' end of the NEMO cDNA. [The positions of PCR products relative to NEMO exons are shown at the top of the figure. Amplification is from fetal cDNA samples G, K and D, cDNA from healthy donors (C1 and C2) and control DNA (D1 and D2). PCR of filamin cDNA from all samples acted as a control for RNA integrity. Primer sequences are in Example 9.]

Amplification from genomic DNA gave larger PCR products (FIG. 1), indicating that results obtained by RT-PCR were not due to the presence of a pseudogene or of contaminating DNA. However, amplification between exon 2 and exon 4 produced the predicted fragment from fetus G and from control RNAs, but no product from fetuses D or K. Similar results were obtained with additional primers. Amplification of filamin A cDNA was used as a control for the integrity of the fetal mRNAs. These results suggest that a large 3' part of the NEMO cDNA is deleted in fetuses K and D. This observation could not be explained by loss of individual exons, since amplification of all 10 coding exons from these samples was achieved. The results suggest a mutation that disturbs mRNA production between primers R4 and R1 located in exons 3 and 4 respectively.

In a fourth sample from an affected male (IP85m) RT-PCR across the entire coding region of NEMO was successful, and the products were completely sequenced. An A to T change (base no. 1259) within the stop codon of the mature message was the only change detected. This would result in the putative addition of 27 novel residues to the carboxyl terminus of the NEMO protein. Examination of the relevant region of genomic DNA (exon 10) from the family IP85 revealed that the male proband's affected mother is heterozygous for the change while her unaffected mother and father are wild type. The mutation has therefore appeared de novo with the disease in this family and is therefore likely to be the underlying cause of the condition.

Figure 2A:
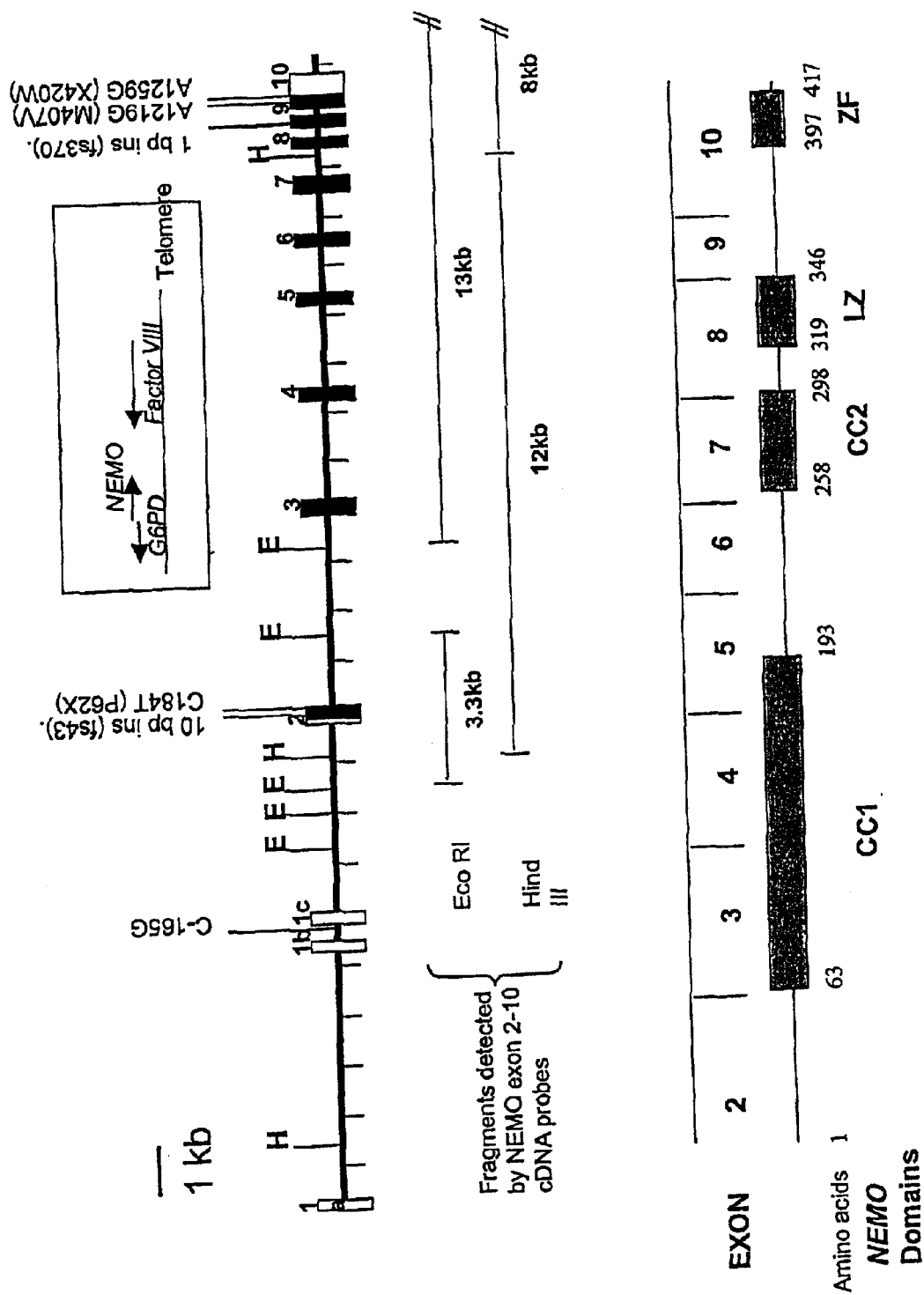
FIGS. 2A through 2C demonstrate genomic structure of the NEMO gene and partial restriction map (H, HindIII; E, EcoRI).
Figure 2B:
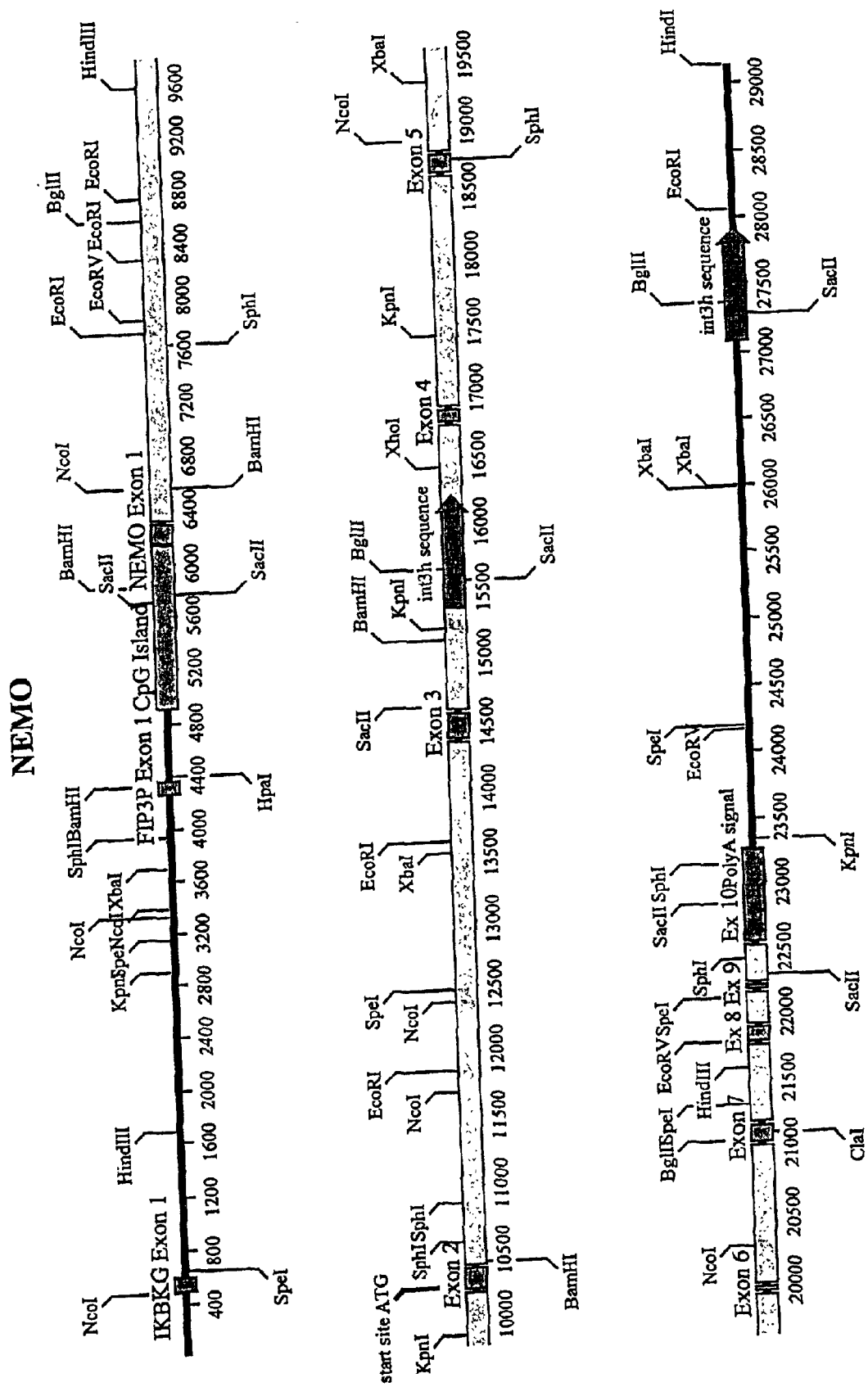
Figure 2C:
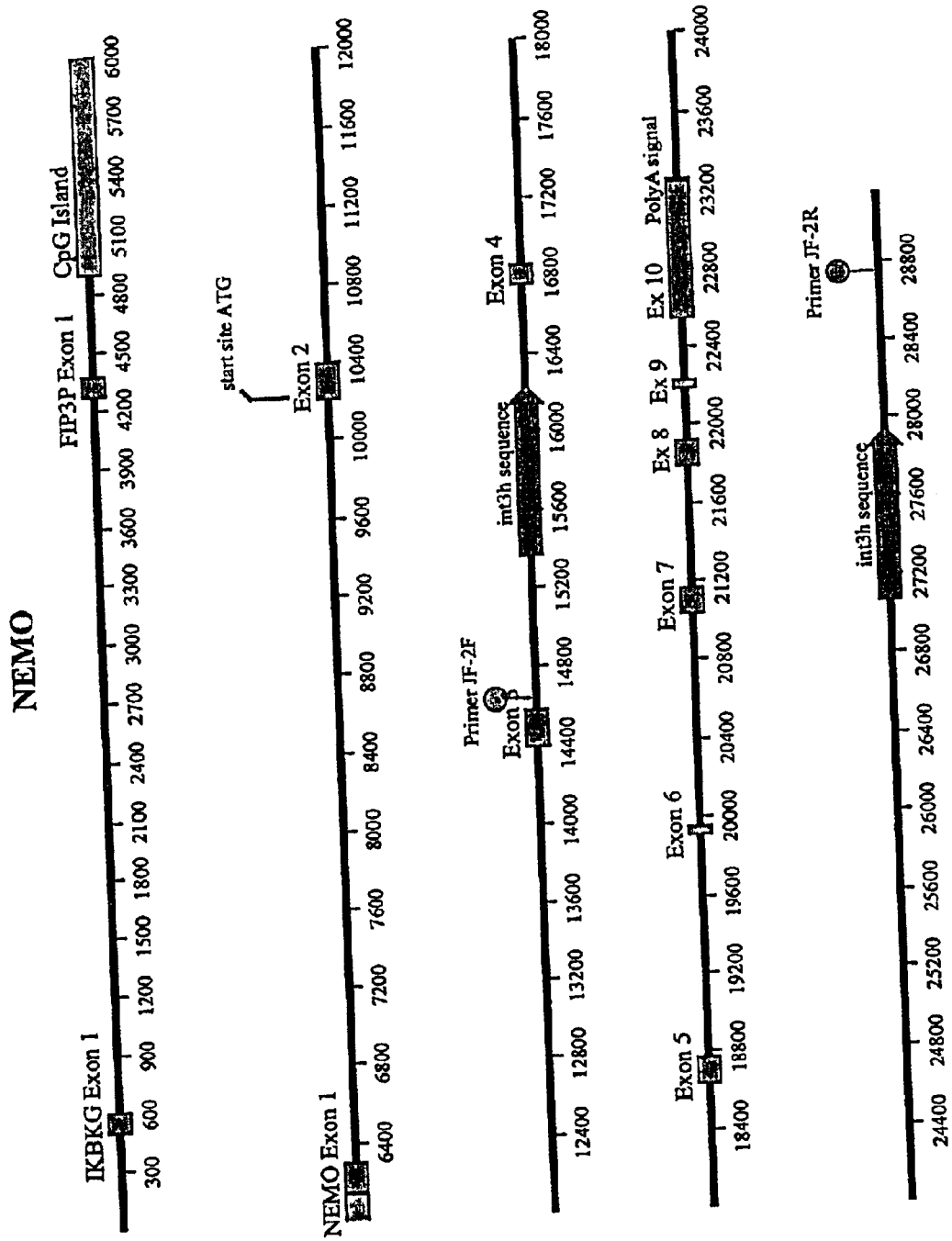

To determine the cause of abnormal RT-PCR in cases K and D and the spectrum of mutations in additional IP families, the complete sequence of the NEMO locus was determined (FIG. 2A). FIGS. 2B and 2C represent diagrammatically the restriction map and characteristics of the NEMO gene and primers described herein. The 23 kb gene contains 10 exons with three alternative first exons (1a, 1b and 1c, and Table 1). As previously reported (Jin and Jeang, 1999), the NEMO gene partially overlaps the G6PD gene and is transcribed in the opposite direction. In FIG. 2 non-coding (open boxes) and coding exons (filled boxes) are shown. Three alternative first exons numbered 1a, 1b and 1c are found spliced to exon 2. The positions of intragenic mutations, a common polymorphism, and restriction fragments seen on Southerns are depicted. The relationship of coding exons 2–10 to the two coiled-coil (CC1 and CC2), leucine zipper (LZ) and zinc finger (ZF) motifs of NEMO secondary structure is illustrated. Inset box: the orientation of NEMO to factor VIII, G6PD and the Xq28 telomere (not to scale) with arrows in a 5' to 3' direction.

TABLE 1

Intron-exon structure of the human NEMO gene

| Intron | Size (bp) | Donor | Acceptor |
|---|---|---|---|
| 1a | 5263 | GTCCCATCAGgtggggaaag (SEQ ID NO:4) | gaagggcgacCGCGAAACTG (SEQ ID NO:5) |
| 1b | 174 | CTGCTGACAGgtgtggtcct (SEQ ID NO:6) | acttgggcggCGAGCTGGAC (SEQ ID NO:7) |
| 1c | 3889 | TGGCAGCTAGgtatctgatt (SEQ ID NO:8) | tctctttcagCCCTTGCCCT (SEQ ID NO:9) |
| 2 | 3981 | GAGCTCCGAGgtgaggaaag (SEQ ID NO:10) | ctgccaccagATGCCATCCG (SEQ ID NO:11) |
| 3 | 2155 | ATGCCAGCAGgtagtcgggg (SEQ ID NO:12) | tatcctgcagCAGATGGCTG (SEQ ID NO:13) |
| 4 | 1757 | TGGAGGGTCGgtgagtcggg (SEQ ID NO:14) | cccgtgccagGGCCCGGGCG (SEQ ID NO:15) |
| 5 | 1128 | CGGAGGAGAAgtgagtcagc (SEQ ID NO:16) | ctttcctcagGAGGAAGCTG (SEQ ID NO:17) |
| 6 | 1023 | GCGGAAGCGAgtgagtgcga (SEQ ID NO:18) | ccgtccttagGGAATGCAGC (SEQ ID NO:19) |
| 7 | 607 | GAAGGCCCAGgtgagggccc (SEQ ID NO:20) | gatttgccagGCGGATATCT (SEQ ID NO:21) |

TABLE 1-continued

Intron-exon structure of the human NEMO gene

| Intron | Size (bp) | Donor | Acceptor |
|---|---|---|---|
| 8 | 257 | AGTCGGCCAGgtgggcctct (SEQ ID NO:22) | gttttcaaagGATCGAGGAC (SEQ ID NO:23) |
| 9 | 298 | CCCGCCCCTGgtgagtgagc (SEQ ID NO:24) | cttttcccagCCTACCTCTC (SEQ ID NO:25) |

EXAMPLE 2

Small Mutations in NEMO Account for a Minority of IP Cases

Figure 3:
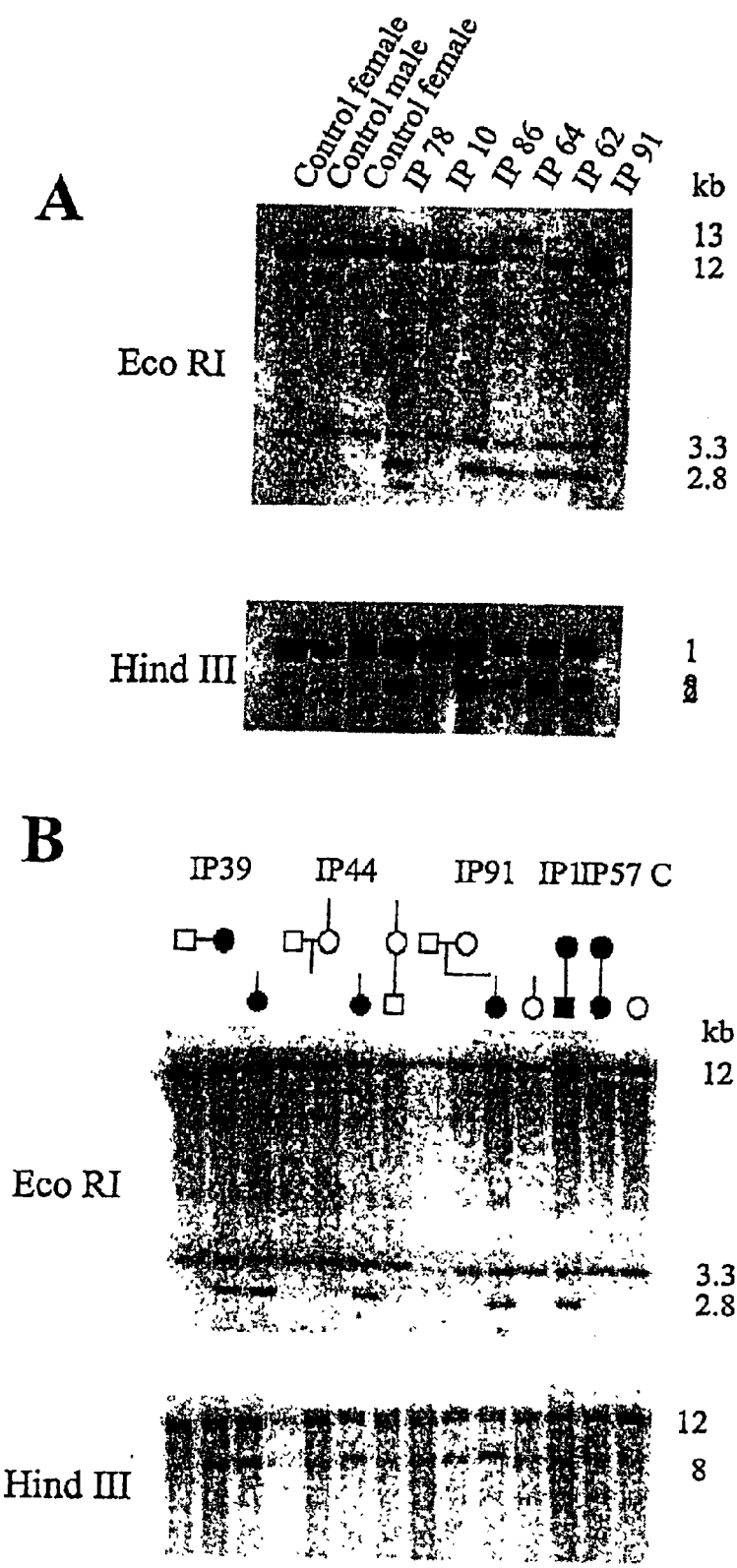
FIGS. 3A through 3E show genomic rearrangement in IP patients.

The entire coding sequence of NEMO was amplified by PCR of exons 1 through 9 and the coding portion of exon 10 in 30 classically-affected unrelated IP patients (see Table 2 for primer sequences). Amplification products were screened for mutations by SSCP, heteroduplex analysis, or direct sequencing. Only 4 additional changes from the reported sequence were found (FIG. 2). A 10 bp insertion in exon 2 in family XL349 was found in both an IP proband and her affected mother but not in unaffected sibs (FIG. 3A). The insertion is an exact duplication of the previous 10 nucleotides and shifts the reading frame of the protein to add 8 novel amino acids after residue 43. IP 10 does not show these bands for either enzyme. A female in family IP64 also has a novel 14 kb band that is not found to segregate with disease. For Hind III a doublet of bands at 12 kb is seen instead of the expected single band in addition bands corresponding to exons 7–10 (faint 8 kb band).

A second insertion in exon 9 of a single C within a run of cytosines was found to segregate with the disease in family XL203 (FIG. 3B). This frameshift mutation would be predicted to append 23 novel amino acids onto proline residue 370 of the translated protein. Segregation in family 39 is also shown. A male sample from family IP1 carrying the rearrangement still retains wild-type Eco RI bands although the smaller of the doublet Hind III bands has disappeared. In FIGS. 3B, C refers to control female DNA.

A missense transition (A/G) in exon 10 that putatively changes a methionine to a valine in the C-terminus of the NEMO protein (M407V) was found in an affected female from family 72. SSCP analysis showed that this relatively conservative change segregates with the disease in the extended pedigree and cannot be detected in 50 control female samples. The schematic shows 12 PCR reactions conducted in patient (IP) versus control (N) samples and the gel shows the products. Ticks denote successful amplification in IP1m, whereas, crosses denote lack of amplification.

Figure 3C:
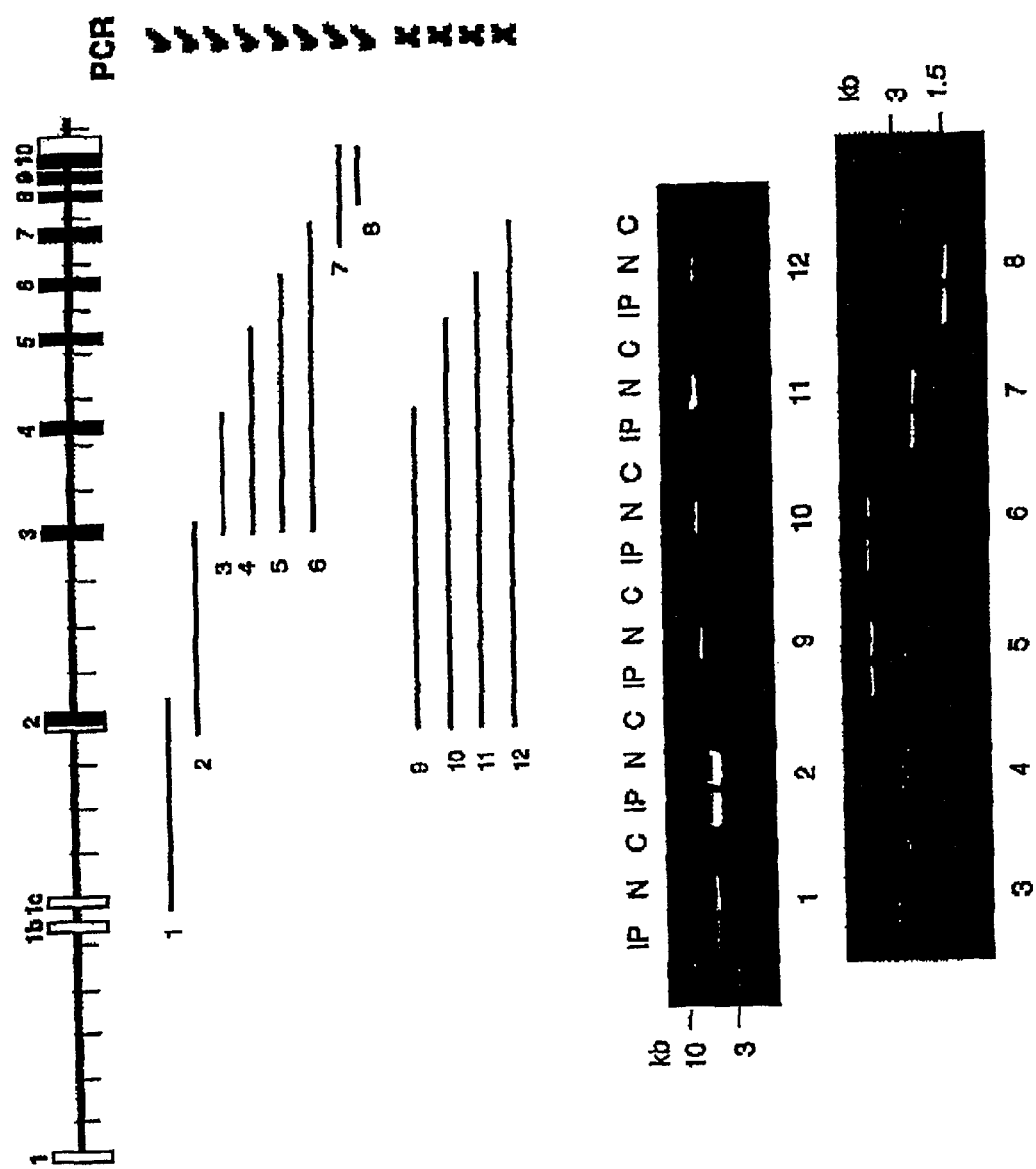
Figure 3D:
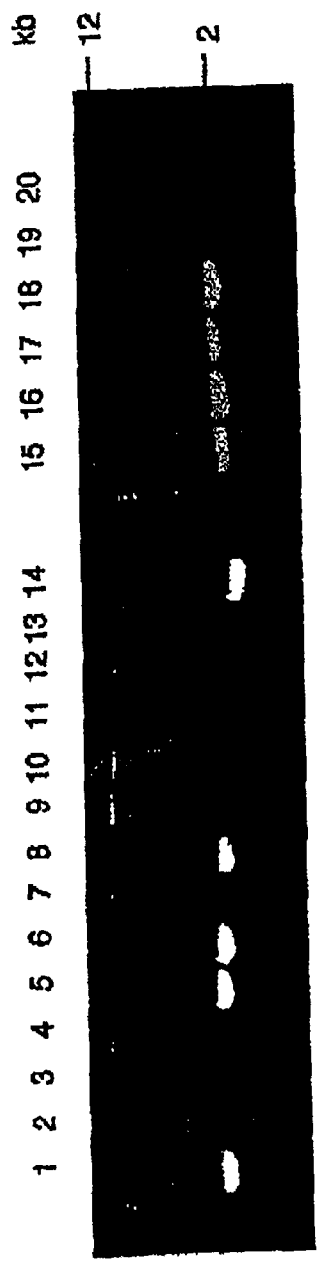

Finally, a C to T (C184T) proline to STOP codon mutation, found in exon 2 in family XL352, predicts a truncated protein consisting of the amino terminal 62 amino acids of NEMO (FIG. 3D). Notably, amplification and sequencing of all coding exons failed to detect any mutation in fetuses K and D. In addition to potentially pathogenic changes, a polymorphism in exon 1c in the 5' untranslated region (−165 from exon1c and 5678 of the NEMO genomic sequence) changes a C to a G in 6/40 chromosomes.

TABLE 2

Primers and conditions for PCR amplification of individual exons

| Exon | Length (bp) | Forward primer (5'–3') | Reverse primer (5'–3') | Product Size (bp) |
|---|---|---|---|---|
| 1a | 125 | GGA AGT CAG CCC AGA AAT GT (SEQ ID NO:26) | GTA CTT ACT GCC CCC TTC CA (SEQ ID NO:27) | 302 |
| 1b | 95 | GGG CGG GGC TTG TGT TTT TA (SEQ ID NO:28) | AGA AGC GCG GAG CAG GAA CG (SEQ ID NO:29) | 297 |
| 1c | 170 | TTC CTG CTC CGC GCT TCT GG (SEQ ID NO:30) | CCA GGA GAG CCC ATT CAT TC (SEQ ID NO:31) | 334 |
| 2 | 202 | TCT GCT GGG TAA GGA TGT GG (SEQ ID NO:32) | TCT GCA GGT GGG GAG AAG AC (SEQ ID NO:33) | 321 |
| 3 | 212 | CCC AGC TCC CCT CCA CTG TC (SEQ ID NO:34) | CAC CTG GCG TCA CTC GGC GGG T (SEQ ID NO:35) | 296 |
| 4 | 119 | CAG TGC TGA CAG GAA GTG GC (SEQ ID NO:36) | AAC CCT GGA AGG GGT CTC CGG AG (SEQ ID NO:37) | 194 |
| 5 | 153 | CAT CAG CTC GCA GTC ACA GG (SEQ ID NO:38) | CCG ACA CTT CTC AGC CTT TC (SEQ ID NO:39) | 351 |
| 6 | 97 | AAG GGG GTA GAG TTG GAA GC (SEQ ID NO:40) | AGG CAA GTC TAA GGC AGG TC (SEQ ID NO:41) | 277 |
| 7 | 144 | GCC ACT CTT TCA TCC TTC TC (SEQ ID NO:42) | TG GGC AAC AAG AGC AAA AC (SEQ ID NO:43) | 347 |
| 8 | 143 | TGC CTG GTG GGT GGC TGG CTT (SEQ ID NO:44) | CAG TGT CGC ACC CAC TGC TCA (SEQ ID NO:45) | 245 |
| 9 | 62 | GCT GCT TTG ACA CTA GTC CA (SEQ ID NO:46) | CAG AGA GCA ACA GGA AGS TC (SEQ ID NO:47) | 234 |
| 10 | 728 | CGG CGG CTC CTG GTC TTA CA (SEQ ID NO:48) | GCC ACC CAG CCC TTC ATC CT (SEQ ID NO:49) | 363 |

Amplification between exon 3 forward primer 3FH (SEQ ID NO:34) and a primer from the L2 repeat in the rearranged Eco RI fragment (JF3R; SEQ ID NO:35) gives a 2 kb band only in IP samples (lanes 1, 5, 6, 8, 14, 15–18). A 13 kb band is seen in control samples that do not have the rearrangement (lanes 2–4, 7, 9–13, 19, 20).

Surprisingly, few additional mutations were detected by screening individual exons of NEMO in IP patients. Moreover, amplification and sequencing of all coding exons failed to detect any mutation in fetuses D and K that could explain the observed abnormality of mRNA structure. In view of the observation and the finding that 2/3 samples analysed by RT-PCR were found to have an abnormality disrupting mRNA structure, the possibility of genomic rearrangement was investigated by Southern blotting.

EXAMPLE 3

Figure 4A:
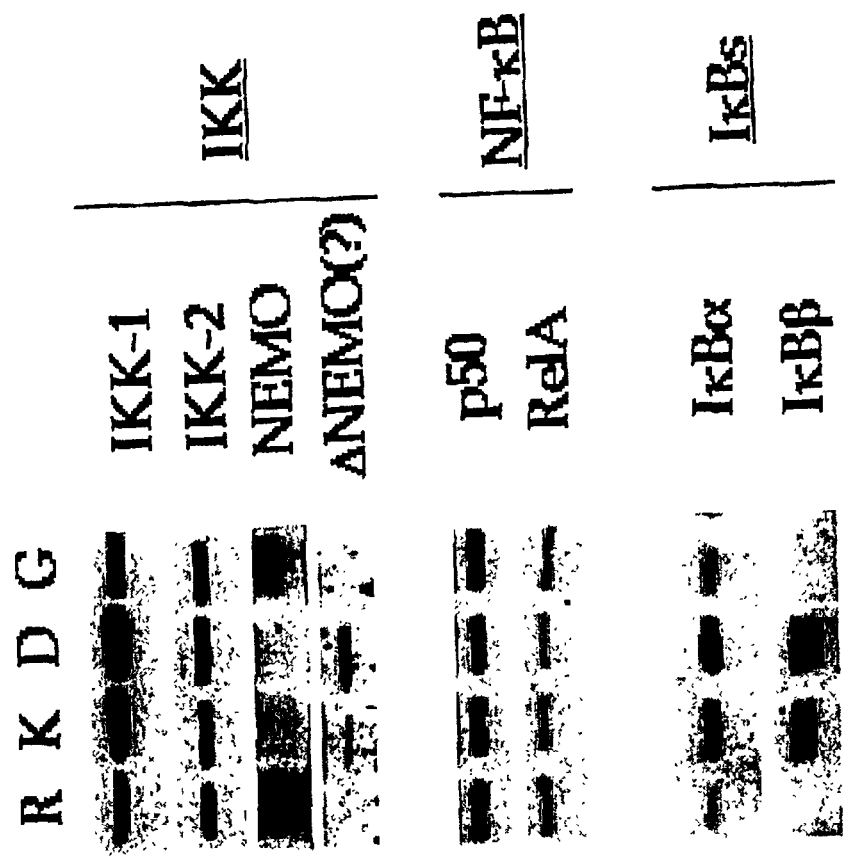
FIGS. 4A through 4D demonstrate characteristic experiments for elucidating function and mechanism of action for NEMO.

A Recurrent Genomic Rearrangement is Responsible for the Majority of IP Cases Genomic DNA from IP patients and normal individuals were digested with Hind III and Eco RI and hybridized to a probe representing the coding region of NEMO cDNA (SEQ ID NO:3). Compared to control samples a novel Hind III band of 8 kb and a novel Eco RI band of 2.8 kb band was observed for 38/47 IP DNA samples (examples shown in FIG. 3A). The novel fragments were concordant for the two enzymes in all cases and notably absent for the affected male IP85m containing a mutation in the termination codon. The novel bands segregated with disease in each pedigree analyzed. In two families an Eco RI band of about 14 kb was observed in addition to the novel 2.8 kb band (for example IP64, FIG. 3A) with a concomitant reduction in signal for the wild type 13 kb band. This band did not segregate with disease in these families and is therefore a non-pathogenic variant. In FIG. 4A cytoplasmic extracts derived from normal, G, K or D EFs were subject to Western blotting with antibodies directed against NEMO, IKK-1, IKK-2, p50, relA, IκBα and IκBβ. ΔNEMO indicates a putative truncated version of NEMO only found in patients K and D.

To confirm that the novel bands are associated with the development of IP, two families with sporadic cases (IP44 and IP91) were analyzed. In both cases, the novel bands (8 kb Hind III and 2.8 kb Eco RI) were found in the proband but not the parents and have therefore appeared de novo with the disease (FIG. 3B). To determine whether the new band represented a deletion, hemizygous DNA from a male abortus, whose mother carries the rearrangement, was screened (IP1m). This male is from a 4-generation IP family (IP1; Jouet, 1997) and has inherited the IP haplotype from his affected mother. NEMO exons 1 a through 10 could be amplified by PCR. Interestingly, when DNA from this male was analyzed by Southern blot analysis, 13 kb and 3.3 kb wild type Eco RI bands as well as the novel 2.8 kb band were seen (lane 12, FIG. 3B). Since only one X chromosome is present in this fetus, more than one sequence homology to the NEMO gene must be assumed. The presence of a doublet of hybridizing Hind III fragments at about 12 kb in all lanes implies at least part of NEMO is duplicated in wild type DNA. Complementary DNA probes encompassing coding sequences from exons 2 and 3 detected the novel IP-specific bands, but probes containing sequences from exons 4 through 10 did not. Furthermore, hybridization with single exons revealed that exon 3, but not exons 2 or 4, is present on the novel Eco RI fragment, whereas exons 2 and 3 but not 4 hybridize to the novel Hind III band.

To investigate whether intronic sequences are involved in the rearrangement, DNA from the male abortus (IP1m) was used to amplify across NEMO introns. Amplification across single introns (with forward and reverse primers flanking individual exons; Table 2) was successful for all introns. However, differences were found compared to controls if PCR reactions were anchored at exon 2 (FIG. 3C). In the affected male (IP1m), amplification was possible from exon 2 to exon 3 but not from exon 2 to exons 4, or 5, or 6, or 7. Anchoring the PCR reactions at exon 3 or 7 yielded wild type products for all combinations with the same downstream exons (FIG. 3C). This is compatible with the existence of a putative second copy of NEMO that contains exons 3–10 but not 1–2. This second copy must be highly homologous. Indeed, sequencing of long range PCR products obtained from IP1m revealed that copies of exon 3 in tandem with either exon 2 or exon 4 were identical in sequence to the wild type exon 3. Analysis of DNA from IP affected male fetus D yielded similar results to those obtained for IP1m for both long range PCR and Southern blotting indicating that the common rearrangement results in the production of aberrant NEMO mRNA. Taken together these data are consistent with a common rearrangement within intron 3. Exon 3 is apparently duplicated as it is present on a rearranged band as well as on wild type restriction fragments on a single haplotype. This interpretation is also indicated by long range PCR results linking exon 2–3 and 3–4 but not 2–4 on the mutated chromosome.

This information was used in a strategy to isolate the boundary of rearrangement neighbouring exon three within the 2.8 kb novel band. DNA from the male abortus (IP1m) was digested with Eco RI and ligated to pre-annealed adapter primers with Eco RI cohesive ends. Nested PCR between adapter primers and exon 3-specific forward primers yielded a product of about 1.9 kb that was completely sequenced. The fragment was found to extend from exon 3 into intron 3 for 1.8 kb. The sequence then diverged from intron 3 identity after a position equivalent to 15749 of the NEMO genomic sequence; a novel 104 base pairs were found between this boundary and the Eco RI site. Interestingly, the boundary between intron 3 and this sequence coincides precisely with the end of a repeat of the MER67B family in intron 3 (for this purpose called boundary repeat 1). The 104 bp B sequence which itself is homologous to an L2 repeat, was used to screen available sequence data from Xq28 BAC clones and found within a short sequence contig from BAC clone 211L10, the BAC clone that also houses the NEMO gene.

To confirm that the novel sequence is associated with the rearranged 2.8 kb Eco RI fragment, PCR between exon 3 and the novel boundary sequence was conducted on families with and without the common rearrangement found on Southern blots (FIG. 3D). The resulting 2 kb band is diagnostic for the rearrangement, occurring only in IP cases that have been shown to have the altered band by Southern blotting and not in either controls or unaffected parents of sporadic cases. This is a simple diagnostic PCR test for 80% of IP cases. The presence of a 13 kb band only in patients or controls without the rearrangement suggested that the natural site for the boundary sequence may be downstream of NEMO. End sequencing of both this band and a 13 kb Eco RI fragment housing exons 3–10 of NEMO from BAC clone 211L10 confirmed this to be the case. Furthermore, sequences identical MER678 of intron 3 were found juxtaposed to the 104 bp of L2 repeat sequence in the same orientation as in the NEMO gene. Further PCR and sequencing between NEMO exons and sequence L2 indicated that although 870 bp of intron 3 is repeated 3' of the NEMO gene there is no additional exon 3 within this fragment.

Figure 3E:
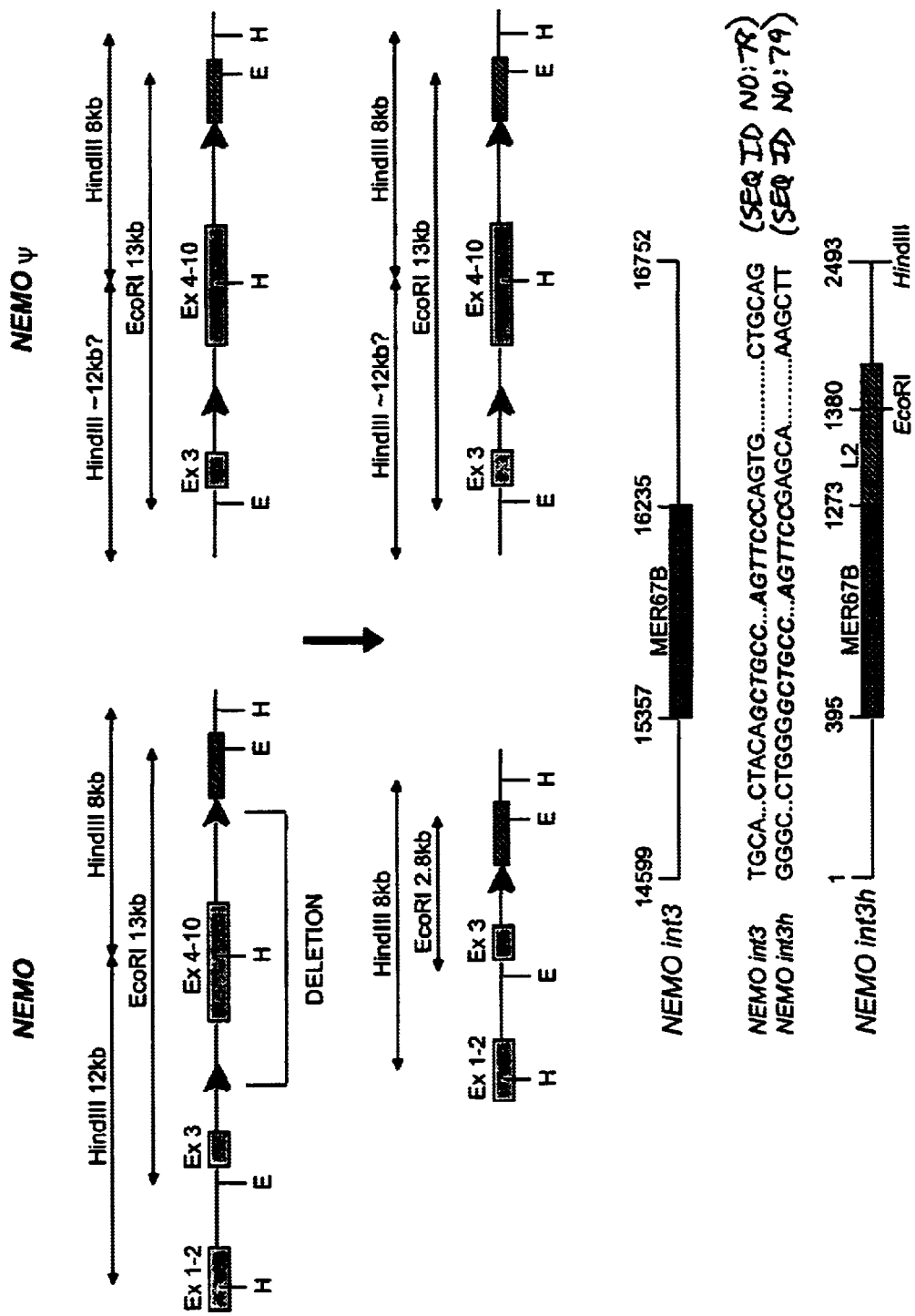
Figure 5:
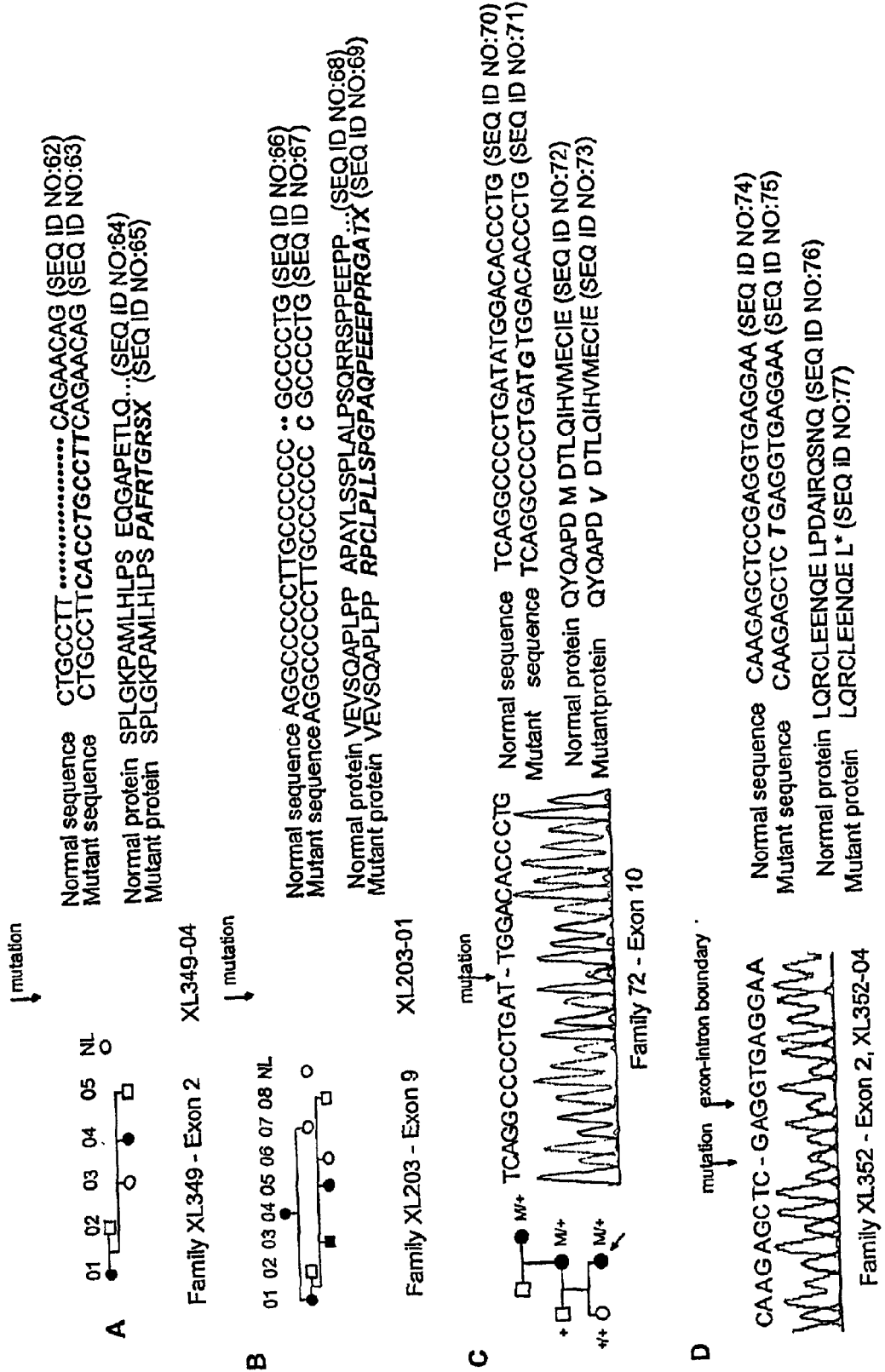
FIGS. 5A through 5D show intragenic mutations in IP families.

The most common mutation in IP is therefore a complex rearrangement of the NEMO gene mediated by directly repeated sequences within intron 3 and 3' of exon 10 (FIG. 3E). FIG. 3E illustrates a model for IP rearrangements. In addition to the bona fide NEMO gene (left hand side) a nEMO pseudogene lacking exons 1 and 2 is hypothesized (right hand side NEMO w). The chromosomal location relaive to NEMO is unknown. An 870 bp region of identity corresponding to a MER67B repeat (blue arrow) exists both in intron 3 and 3' to exon 10. An L2 repeat follows the 3' MER67B sequence at the downstream site (green box). Recombination between the regions of identity will delete exons 4 to 10 of NEMO. Diagnosti PCR between exon 3 and the L2 sequence yields a 2 kb band in patients and a 13 kb ban in healthy controls. The translocation of sequences from this downstream region to intron 3 can explain the novel band sizes observed on Southern blots as Eco RI and Hind II sites are found at appropriate positions 3'. A summary of mutations in NEMO described herein is illustrated in FIG. 5.

EXAMPLE 4

Defective NF-κB Activation in Incontinentia Pigmenti Patients

NEMO has been shown to play an essential role in the NF-κB activation process (Yamaoka, 1998). NF-κB homo- or heterodimers are sequestered in the cytoplasm through interaction with an inhibitory molecule of the IkB family. Upon cytokine stimulation, the IkB molecules are phosphorylated, polyubiquitinated and degraded through the ubiquitin-proteasome pathway (Ghosh et al., 1998; Rothwarf and Karin, 1999). NF-κB is then free to translocate to the nucleus and to activate its target genes. This phosphorylation event is carried out by a high molecular weight, multiprotein, kinase complex containing two subunits with kinase activity (IKK1/a and IKK2/b). The third known component of this IKK complex is NEMO (Ikkg, IKKAP or Human Gene Nomenclature name: IKBKG) a 48 kDa protein with no apparent catalytic activity that directly interacts with the kinase subunits and is for activation of the kinase complex in response to extracellular (or intracellular) stimuli: its absence results in a complete inhibition of NF-κB activation.

It was therefore determined whether NF-κB activation was defective in IP patients. The analysis was carried out on primary embryonic fibroblasts (EFs) derived from patients G, K and D, with primary EFs derived from a healthy subject as a control. Cytoplasmic extracts from EFs were analyzed by Western blotting for the abundance of the three known subunits of IKK (IKK-1, IKK-2 and NEMO), the two major subunits of NF-κB (p50 and re1A), and two IkB species (IkBα and β) (FIG. 4A). As predicted from the genomic analysis reported above, no 48 kD band corresponding to the NEMO molecule was detected in patients K and D EFs compared to controls. Interestingly for these patients, a low molecular weight band of approximately 15–20 kD was detected. Its size and immunoreactivity suggests that it may represent a truncated version of NEMO. Analysis of IKK-1, IKK-2, p50, and re1A proteins levels did not reveal any significant differences between patients and controls. However, a substantial increase of IkBα and IκBβ was seen in patients K and D EFs. Since the level of IκBs is under the control of NF-κB this observation suggested that the NF-κB system may be perturbed in IP patients.

Figure 4B:
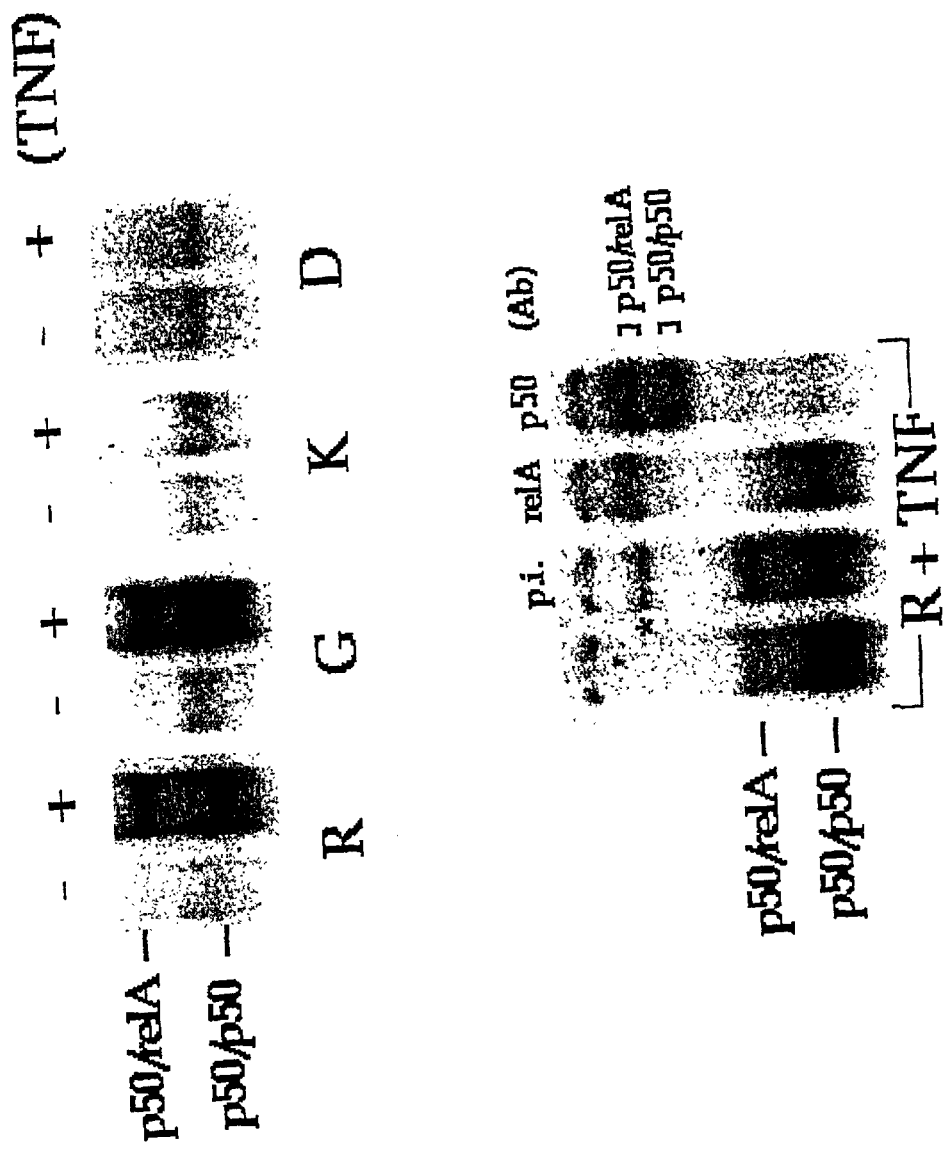

Having established that full length NEMO was absent from patients K and D EFs, we looked for NF-κB activation in these cells with an electrophoretic mobility shift assay (FIG. 4B). Upon TNF stimulation, two retarded complexes were observed with nuclear extracts prepared from normal and patient G EFs. A supershift experiment demonstrated that the upper complex was composed of both p50 and re1A proteins, whereas the lower one was composed of p50 only (FIG. 4B). Importantly, induction of neither p50/re1A nor p50/p50 complex was observed with nuclear extracts derived from TNF-treated patients K and D EFs, indicating a complete defect in the NF-κB activation process. A similar observation was made with IL-1 instead of TNF.

Figure 4C:
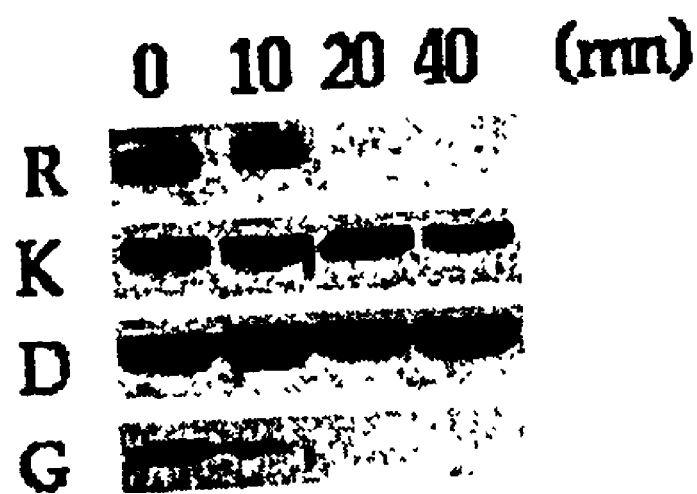

Since the translocation of NF-κB to the nucleus results from degradation of IκB, the fate of IκBα in normal and IP EFs after treatment with TNF or IL-1 was also analyzed. Whereas patient G and control EFs exhibited complete IκBα disappearance after 40 mn of TNF or IL-1 treatment, no such disappearance could be observed in patients K and D EFs (FIG. 4C). EFs derived from normal, G, K or D patients were treated with TNFα(10 ng/ml) for the indicated times (minutes) and cytoplasmic extracts were prepared and analysed, after Western blotting, with anti-IκBα antibody.

Figure 4D:
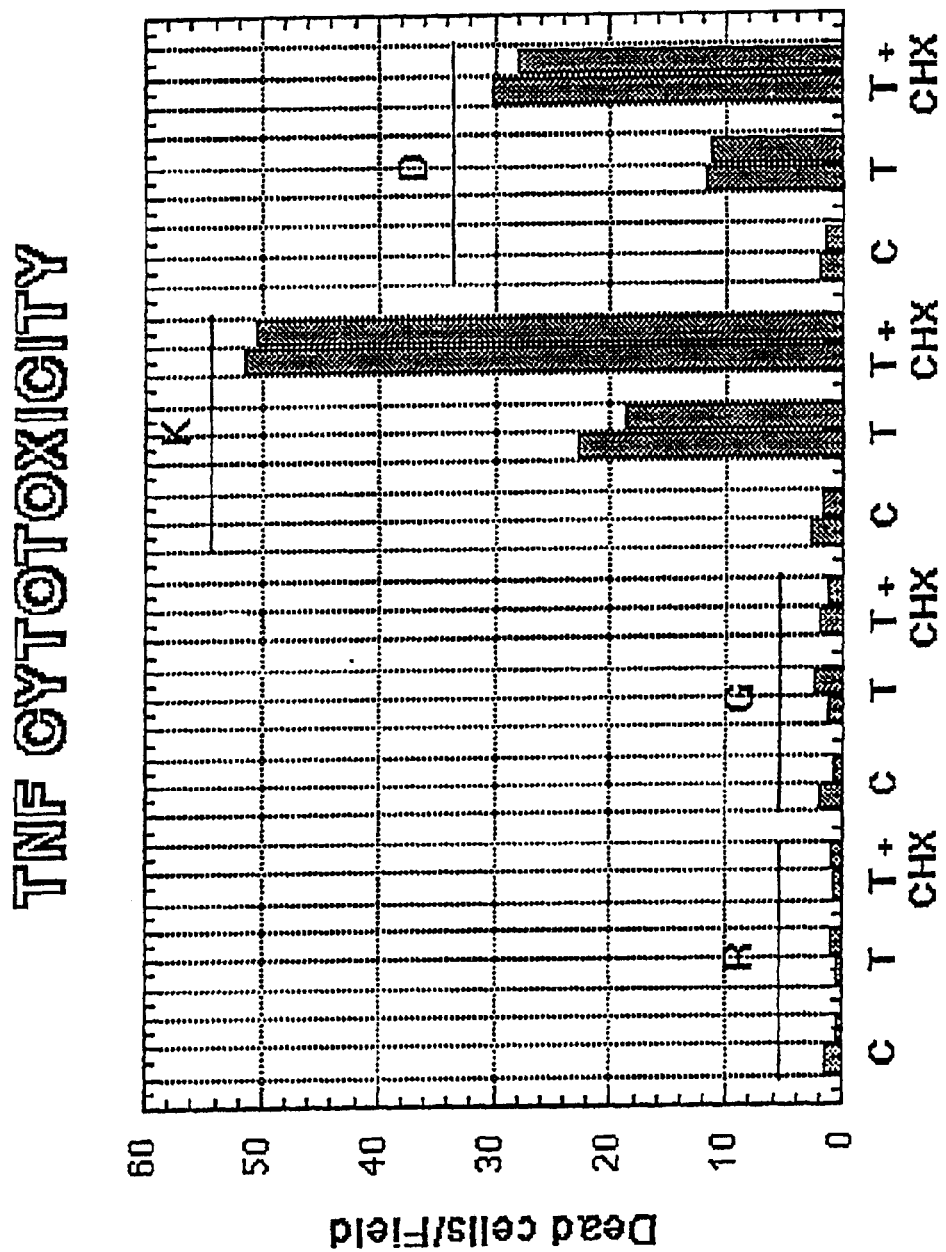

In several cell types, including embryonic fibroblasts, NF-κB has been shown to play a protective role against TNF-induced apoptosis. For instance, EFs derived from p65 or IKK-2 Knockout mice exhibit a high sensitivity to TNF. We therefore analyzed the TNF sensitivity of normal and IP EFs (FIG. 4D). In contrast to normal or patient G EFs, which were unaffected by TNF or TNF plus cycloheximide treatments, EFs derived from patients K and D were sensitive to TNF and this sensitivity was increased upon co-treatment with cycloheximide. EFs derived from normal, G, K or D patients were mock(C), TNFα(T) or TNFα plus Cycloheximide (T+CHX)-treated for 20 h and the cell viability was determined through trypan blue exclusion. A duplicate experiment, out of two giving similar results, is shown.

All these data demonstrate a lack of NF-κB activation in IP EFs, resulting from a defect at the level of the NEMO molecule. As a consequence, IP cells exhibit a high sensitivity to pro-apoptotic signals.

EXAMPLE 5

Significance of the Loss of NF-κB Activation

Two major conclusions can be drawn from the analysis of IP. First, the disorder is due to a defect in NF-κB activation associated with the absence of functional NEMO protein, and second, the majority of cases result from a novel rearrangement of the NEMO gene in Xq28. IP therefore joins a growing list of disorders caused by genomic rearrangement (Lupski, 1998). The mutational mechanism in IP involves direct LTR/MER repeats that are identical in sequence over a considerable distance (over 600 bp), an apparent requirement in many other examples. The rearrangement in IP may not conform to the simple model of either deletion or duplication resulting from illegitimate recombination between mis-aligned direct repeats and may involve either additional homologous NEMO sequences that have not yet been defined or a complex mixture of recombination and gene conversion. Similarly complex events are involved in Hunter syndrome, another Xq28-linked disorder, where localised recombination with a highly homologous putative pseudogene is involved (Bondeson, 1995; Timms, 1997; Lagerstedt, 1997). Although the complexity of the IP rearrangement has not been unravelled fully, a diagnostic PCR for the rearranged chromosome has been developed. This has immense clinical value for a disorder with such variability in presentation and diagnostic uncertainty. Of the 9/47 IP patients found not to have a rearrangement, 6 have been screened for intragenic changes and 4 found to have mutations. This finding finally dispels the idea that two major loci for IP exist on the X-chromosome, one in Xq28 determined by linkage analysis and one defined by translocation involving the short arm of the X (Gorski, 1993). A variety of hypotheses have been put forward to explain apparent anticipation in IP families. These include evolution of an unstable premutation such as a triplet repeat sequence (Traupe, 1994; Hatchwell, 1996). However, the nature of the rearrangement as detected by Southern blotting or PCR runs true in families, and no genomic differences have been detected between parents of sporadic cases healthy controls at the NEMO locus. Nevertheless, it is possible that an as-yet-undefined duplication or other genomic alteration predisposes to the full rearrangement in unaffected or mildly affected individuals.

Genomic rearrangements often show a predilection for parent of origin. For example, homologous recombination between tandem repeats leading to de novo duplication in CMT1A occurs primarily during male gametogenesis (Lopes, 1997). Similarly repeat-mediated inversion in 47% of cases of hemophilia A occurs almost exclusively in male germ cells (Rossiter, 1994). For IP, 2/3 of new mutations studied originate from fathers, in keeping with this paternal bias for genomic rearrangement (Parrish, 1996). The origin of mutation has been established for 12 of the patients with the rearrangement and 10 occurred during male gametogenesis. The bias towards male gametogenesis for the IP rearrangement implicates intrachromosomal interchange.

Where genomic rearrangement is responsible for a disorder, it is important to establish whether one or more genes are implicated in the development of the phenotype. Herein it is shown that intragenic mutations can also give rise to IP. These segregate with the disease in families or have arisen de novo with the disease, indicating that defects in NEMO alone give rise to the disorder.

That NEMO activity is indeed ablated by the rearrangement has been shown for two cell lines expressing this mutation. Can the pathology observed in IP male and female patients therefore be explained in terms of NEMO function? NEMO is a structural/regulatory component of the IKK complex that also contains IKKα/1 and IKKβ/2 (Yamaoka, 1998; Courtois, 1997; Rothwarf, 1998; Mercurio, 1999). Ablation of NEMO activity results in the inability of a cell to activate NF-κB in response to a series of stimuli (Courtois, 1997; Yamaoka, 1998). The NF-κB signalling pathway itself has been implicated in immune, inflammatory, and apoptotic responses (for a review see Ghosh, 1998; Baldwin, 1996). Recently, the genes encoding the components of the IKK complex, including NEMO, have been inactivated by homologous recombination. Inactivation of IKK2 (which does not entirely abolish NF-κB activation, probably due to partial compensation by the IKK1 kinase subunit) resulted in embryonic death due to massive liver apoptosis at day 14 (Li, 1999; Li, 1999; Tanaka, 1999) while that of NEMO (which apparently results in a complete block in NF-κB activation) resulted in death of the male embryos at day 12 with a similar phenotype (murine NEMO is also located on the X-chromosome). Apparently the females were normal. A similarly dramatic phenotype was observed when the gene encoding relA, the most ubiquitously expressed and most potent transcriptional activator of the NF-κB family, was inactivated: the mice died at embryonic day 15–16 from massive liver apoptosis (Beg, 1995). Interestingly this apoptosis is due to the pro-apoptotic effect of TNF, as demonstrated by the viability of mice carrying an inactivation of both the relA and the TNF genes (Doi, 1999). This observation is in keeping with the high sensitivity to TNF-induced apoptosis in cell lines derived from IP patients (FIG. 5D). In both mice and humans, therefore, the complete absence (or lack of activity) of NEMO results in early lethality of the affected males. Post mortem examination of a few human affected males has suggested the involvement of an abnormal immune response, as expected from a defect in NF-κB signalling.

A prominent role for NF-κB in the apoptotic response also has a bearing on the phenotype in heterozygous females (Foo, 1999; Van Antwerp, 1996). If the NF-κB response is blocked by chemical means, B cells exhibit spontaneous apoptosis (Wu, 1996) while in other cell types, inhibition of NF-κB results in massive apoptosis in response to a series of stimuli, in particular TNF (Wang, 1996; Van Antwerp, 1996; Beg, 1996). Therefore, it is most likely that skewing of X-inactivation, at least in blood, results from progressive elimination, by apoptosis, of cells bearing mutated NEMO on the active X-chromosome. It is unclear at the moment why NEMO-deficient female mice do not exhibit a phenotype comparable to that seen in man. One possibility is that the mechanism of X-inactivation somehow differs between mice and humans or takes place at different times during development. For example the lines of Blashko in mice are not as visible and precise as in humans. Alternatively, compensation by non-affected cells might vary not only from one tissue to another, but also from one species to another.

Due to the effects of Lyonisation and the lack of phenotype in NEMO−/+ mice, it is more difficult to understand the multiple effects observed in affected females. However, some interesting clues emerge from the results of targeting of other components of the NFKB pathway in mouse (Attar, 1997). The individual inactivation of 4 among the 5 known members of the NF-κB family results in more or less severe defects in the immune response: inactivation of the p105/p50 subunit results in multifocal defects in immune responses involving B lymphocytes and nonspecific responses to infection (Sha, 1995). Inactivation of the c-rel subunit results in defects in lymphocyte proliferation, humoral immunity, and interleukin-2 expression (Kontgen, 1995). Inactivation of the p100/p52 subunit results in defects in splenic microarchitecture and B cell-mediated immune responses (Caamano, 1998; Franzoso, 1998). More interestingly, mice devoid of both the p105/p50 and the p100/p52 subunits fail to generate mature osteoclasts, causing severe osteopetrosis (Franzoso, 1997; Iotsova, 1997). This osteopetrotic phenotype could be rescued by bone marrow transplantation, indicating that the hematopoietic component was impaired. Osteoclasts are also essential for tooth eruption as they resorb the alveolar bone to form an eruption pathway. Osteopetrosis in mouse models is frequently associated with delayed or absent eruption, a prominent feature of the human, IP phenotype.

Another interesting hint comes from the analysis of mice carrying an inactivation of the IKK1 component of the complex that includes NEMO (Hu, 1999; Li, 1999; Takeda, 1999). Inactivation of this kinase results in a completely unexpected phenotype: the resulting mice exhibit an almost intact activation of NF-κB by pro-inflammatory stimuli but show multiple defects in morphogenetic events, including limb and skeletal patterning and proliferation and differentiation of epidermal keratinocytes. Such an epidermal phenotype has also been observed with transgenic mice expressing a dominant negative version of IκBa under skin-specific promoter control (Seitz, 2000; van Hogerlinden, 1999; Seitz, 1998). At the skin level NF-κB appears to play a dual role: it controls cell growth in the stratified epithelium and regulates apoptosis. Defect in both pathways may explain the characteristic skin lesions observed in IP2.

Also reminiscent of the abnormalities observed in female IP patients, are the deformed incisors as well as the lack of hair follicles in the IKK1-/- mice.

The phenotype observed for the only surviving male with a mutation in NEMO (IP85m) provides a unique view of the consequences of impaired NF-κB function in man. Severely compromised immune cell function, lack of teeth and osteopetrosis are all consistent with mouse models of defective NF-κB function. With respect to a clear defect in osteoclast function, an intriguing comparison can be made between the phenotype in IP85m and that of patients with familial expansile osteolysis (FEO, or familial Paget disease of bone, PDB). This is an autosomal dominant disorder characterised by focal areas of increased bone remodelling. In contrast to the current report, activating mutations in the gene for a positive activator of NF-κB function (RANK) have been found to account for this disorder in two families (Hughes, 2000). Interestingly, IP85m also showed signs of capillary bed abnormalities, both in the skin and the gut, implying an unsuspected role for NF-κB in the maintenance of blood vessel architecture.

The chromosomal rearrangement found in the majority of the patients would result in a truncated molecule carrying only the 144 N-terminal amino acids of NEMO (encoded by exons 1–3). This molecule may still interact with IKK-2 but is unlikely to respond to upstream signals (and may even behave as a dominant-negative molecule). It is interesting to correlate the localisation of the point mutations found in several IP patients in the NEMO coding region with the results of a structure-function analysis of the NEMO molecule. The mutation in family XL-349 results in a NEMO molecule consisting of only 61 N-terminal amino acids. This short peptide could not interact with IKKs and is certainly inactive. The insertion that introduces a frameshift after amino acid 370 results in the replacement of the entire C-terminal Zinc finger domain by 23 unrelated amino acids. The deletion of this zinc finger domain results in a severe loss of function of the NEMO molecule in complementation assays. It will be interesting to determine whether the mutation that results in the replacement of Met 407 in the zinc finger region by a Val residue also results in a loss of function. An intriguing mutation is the one that effects the stop codon found in male patient IP85m who died at the age of 2 years. This mutation results in the putative addition of 27 amino acids at the C-terminus of the molecule; a likely explanation of this phenotype is that this mutation results in a partial loss of function of NEMO. Indeed addition of a heterologous protein sequence at the C-terminus of NEMO has been shown to result in an impaired activity of the molecule, supporting this interpretation. Thus, with few exceptions, mutations causing IP severely truncate the NEMO protein and result in loss of function. The survival of a male patient with a potentially less functionally-severe mutation raises the intriguing possibility that missense mutations with only minor effect on NEMO function may cause a less morbid phenotype in males and thus explain the spate of cases of males with an "IP-phenotype". Furthermore, missense mutations in NEMO may contribute to a wide range of conditions related to IP such as immune deficiency, osteopetrosis, and other dental and ophthalmological abnormalities.

Finally, further studies of a genetic disease caused by a defect in NF-κB activation will undoubtedly extend our understanding of the physiological role of this signalling cascade as well as of the molecular structure and function of the NEMO molecule.

EXAMPLE 6

Collection of Families and Preparation of Samples

Families with IP were ascertained through the Incontinentia Pigmenti Research program approved by the Institutional Review Board for Human Subject Research at Baylor College of Medicine (Houston, Tex.) and by regional and national referrals with Ethical Committees' approval at the collaborating institutions. All affected females exhibited or manifested a history of perinatal blistering and at least one other stage of skin lesions, and compatible dental, and/or eye, and/or CNS abnormalities reviewed by clinicians unaware of the molecular studies.

EXAMPLE 7

Fibroblast Lines

Primary fibroblast cultures were maintained in 199 medium with 10% FCS. Three lines expressing a mutant IP X-chromosome were available. The first line was derived from an affected female fetus (K) belonging to a three-generation IP2 family linked to Xq28. After the observation of generalized edema, the pregnancy was aborted spontaneously around 11–12 weeks gestation. The skewed pattern of X-chromosomal inactivation in this fetus resulted in the expression of the maternal X-chromosome bearing the IP2 mutation only (Smahi et al.). The second line was derived from a male affected fetus (D) spontaneously aborted around 10–11 weeks gestation. His mother only had faint pigmentation of the leg associated with dental abnormalities. She had three spontaneous abortions of male fetuses and had a skewed pattern of X-inactivation. The third line was derived from a medically interrupted affected female fetus (G), belonging to a large IP2 family linked to Xq28 region. A fourth line (IP85m) was established from the affected son of a classically affected female IP case. The proband's mother exhibited an early rash and developed marked skin hyperpigmentation that persists into adulthood. She was diagnosed at 2 years old through skin biopsy and has a divergent squint, incomplete eruption and malformation of teeth, and skewed X-inactivation. Her son was born at term with multiple capillary hemangiomas after a normal pregnancy. He developed lymphedema of the lower limbs and failed to thrive due to poor food absorption. Despite a destructive red blood cell picture and recurrent infections due to poor immune cell function, he survived until age 2 and a half years, whereupon he succumbed to a tuberculosis infection. During his short life he had operations to remove his spleen and a gut stricture; biopsies revealed abnormal capillary beds in the gut, extrahepatic erythropoiesis, and osteopetrosis. His skin developed a reticular pigmentation consistent with inheritance of an IP mutation, and his cognitive development was normal.

EXAMPLE 8

DNA Technology and Mutation Screening

DNA was extracted from peripheral venous samples by a proteinase K/SDS treatment followed by phenol and chloroform extractions. DNA was extracted from cultures lymphoblasts, amniocytes, and CVS cells with standard protocols. Southern blots were conducted with neutral transfer onto Immobilon NY+(Millipore) and UV crosslinking. DNA probes were radiolabelled with $^{32}$P and hybridised with methods recommended by Millipore. PCR amplification of individual NEMO/IKKgamma exons was conducted with Amplitaq gold and primers described in table X. Long range PCR was conducted with EXPAND™ long Template PCR System (Roche Molecular Biochemicals, Germany). DNA sequencing was conducted with BigDye terminator cycle sequencing (Perkin Elmer). SSCP and heteroduplex analyses were conducted with previously described protocols (Jouet, 1994; Alonso, 1996; Nigro, 1995).

EXAMPLE 9

RNA Isolation and RT-PCR

Poly A+ RNA was isolated from fibroblast cultures with Ingenious Mini Message Maker (R& D Systems) and cDNA prepared with the AmpGold RNA PCR system (Perkin Elmer) and random primers. Primers used for amplification of NEMO cDNA:

```
E2F(5'-CCCTTGCCCTGTTGGATGAAT-3';  SEQ ID NO:50),
R(5'-CGTCCTCGGCAGGCAGTGGCC;       SEQ ID NO:51),
F1(5'-GGCCACTGCCTGCCGAGGACG;      SEQ ID NO:52),
R1(5'-ACCCTCCAGAGCCTGGCATTG-3';   SEQ ID NO:53),
R2(5'-CATTCCTCGCTTCCGCTCACT-3';   SEQ ID NO:54),
R4(5'-CTTCAGATCGAGCTTCTCGAG-3';   SEQ ID NO:55),
LZF(5'-GCGGACTTCCAGGCTGAGAGG-3';  SEQ ID NO:56).
```

EXAMPLE 10

Genomic Sequencing of a BAC Clone Containing NEMO

The entire cDNA of NEMO gene was contained within the BAC clone 211IL10 from RPCI11 (human male BAC library). To obtain the genomic structure of the human NEMO gene, the complete sequence was determined by a combined strategy of sequencing the positive BAC clone as well as long range genomic PCR products. The BAC was grown in selective media. DNA was prepared by standard protocols and digested with Eco RI. Sequencing was carried out by shotgun sequencing of M13 subclones. The BAC DNA was sonicated and the ends repaired with T4 DNA polymerase. Fragments of 1–2 kb were fractionated from the mixture by agarose gel electrophoresis and subcloned into M13 mp18 vector prepared by digestion with Sma I. 550 M13. 20 000 clones were transferred on to nitrocellulose filtres and hybridised with the human NEMO cDNA clone. 120 positive M13 clones were sequenced with Big-dye Terminator reactions on Applied Biosystems 373A and 377 PRISM automated sequencers. Sequence tracts were assembled with Applied Biosystem's FACTURA™ and INHERIT™ programs. These programs simultaneously assemble the sequence files, give a profile of the status of the project, and provide a window with data traces properly aligned to facilitate the subsequent editing required to arrive at a consensus sequence. Gaps were then closed by PCR primers to amplify the intervening material. The exon-intron boundaries were readily identified from a comparison of the genomic and cDNA sequences and are given in Table 1.

The human genomic sequence is listed under accession number AJ271718. The cDNA sequence is listed under AF091453.

EXAMPLE 11

Adapter PCR Isolation of the Intron 3 Rearrangement Boundary

DNA from a male abortus with an IP haplotype and NEMO rearrangement from family IP1 (Jouet et al) was digested with Eco RI and purified by ethanol precipitation. 750 pmoles of Adapter primers Eco adapt1 (5'-CTAATACGACTCACTATAGGGCTCGAGCAGCC TCCGAGGGCAG-3 SEQ ID NO:57) and Eco adapt2 (5'-P-AATTCTGCCCTCGGAG-3'; SEQ ID NO:58) were pre-annealed by denaturing in 30 µl buffer (5 mM Tris pH 7.4, 50 mM MgCl2). 12 ng of genomic DNA was ligated to a 250 fold molar excess of pre-annealed adapter primers in a 10 µl ligation reaction with T4 DNA ligase and manufacturers buffer (NEB). Primers AP1 (5'-CCATCCTAATACGACTCACTATAGGGC-3'; SEQ ID NO:59) and exon 3 forward primer 3F (SEQ ID NO:34) were used in a primary PCR reaction with the EXPAND™ long Template PCR System (Roche Molecular Biochemicals, Germany) with no specific product. A nested react on with adapter primer AP2 (5'-TCACTATAGGGCTCGAGCAGC-3': SEQ ID NO:60) combined with a primer F3 from within exon 3 (5'-CGGCAGAGCAACCAGATTCTGC-3': SEQ ID NO:61) yielded a single 2 kb fragment.

EXAMPLE 12

Investigating NF-κB Function in IP Fibroblast Lines

Recombinant human interleukin-1α was derived from Biogen (Geneva, Switzerland). Recombinant human TNFα was from PreproTech (Rocky Hill, N.J., USA). Cycloheximide was supplied by Sigma (St-Louis, Mo., USA).

EXAMPLE 13

Antisera

The following rabbit antisera were used: anti-NEMO (Yamaoka, 1998) anti-p50 1141 and anti-re1A 1226 (Rice, 1992), anti-IαBβ 30715 (Weil, 1997). Purified polyclonal antibody directed against IKK-2 and IκBα were obtained from Santa Cruz (Santa Cruz, Calif., USA). IKK-1 monoclonal antibody was from Pharmingen (San Diego, Calif., USA).

EXAMPLE 14

Preparation of Cell Extracts and Western Blot Analysis

Cytoplasmic extracts were prepared as described elsewhere (Courtois et al.,). They were fractionated on sodium dodecyl sulfate-10% polyacrylamide gel and transfered to Immobilon (Millipore, Bedford, Mass., USA) membranes. After blocking in 3% milk-PBS, membranes were treated as described (Courtois, 1997) and revealed with the Supersignal detection system from Pierce (Rockford, Ill., USA).

EXAMPLE 15

Electrophoretic Mobility Shift Assays

Nuclear extracts were prepared and analysed as described (Courtois, 1997) with a 32P-labeled MHC-1 probe. For supershifting experiments, extracts were preincubated for 20 mn at room temperature with 1 µl of antiserum.

EXAMPLE 16

Cytotoxicity Assays

Cells were treated for 20 h, in complete growth medium, with 20 ng/ml TNFα or 20 ng/ml TNFα plus 300 ng/ml cycloheximide. Viability of cells was estimated by trypan blue exclusion.

REFERENCES

All patents and publications mentioned in the specification are indicative of the level of those skilled in the art to which the invention pertains. All patents and publications are herein incorporated by reference to the same extent as if each individual publication was specifically and individually indicated to be incorporated by reference.

Patents
European Application No. 320 308
European Application No. 329 822
GB Application No. 2 202 328
PCT Application No. PCT/US87/00880
PCT Application No. PCT/US89/01025
PCT Application WO 88/10315
PCT Application WO 89/06700
PCT Application WO 90/07641
U.S. Pat. No. 5,840,873, issued Nov. 24, 1998
U.S. Pat. No. 5,843,640, issued Dec. 1, 1998
U.S. Pat. No. 5,843,650, issued Dec. 1, 1998
U.S. Pat. No. 5,843,651, issued Dec. 1, 1998
U.S. Pat. No. 5,843,663, issued Dec. 1, 1998
U.S. Pat. No. 5,846,708, issued Dec. 8, 1998
U.S. Pat. No. 5,846,709, issued Dec. 8, 1998
U.S. Pat. No. 5,846,717, issued Dec. 8, 1998
U.S. Pat. No. 5,846,726, issued Dec. 8, 1998
U.S. Pat. No. 5,846,729, issued Dec. 8, 1998
U.S. Pat. No. 5,846,783, issued Dec. 8, 1998
U.S. Pat. No. 5,849,481, issued Dec. 15, 1998
U.S. Pat. No. 5,849,483, issued Dec. 15, 1998
U.S. Pat. No. 5,849,486, issued Dec. 15, 1998
U.S. Pat. No. 5,849,487, issued Dec. 15, 1998
U.S. Pat. No. 5,849,497, issued Dec. 15, 1998
U.S. Pat. No. 5,849,546, issued Dec. 15, 1998
U.S. Pat. No. 5,849,547, issued Dec. 15, 1998
U.S. Pat. No. 5,851,770, issued Dec. 22, 1998
U.S. Pat. No. 5,851,772, issued Dec. 22, 1988
U.S. Pat. No. 5,853,990, issued Dec. 29, 1998
U.S. Pat. No. 5,853,993, issued Dec. 29, 1998
U.S. Pat. No. 5,853,992, issued Dec. 29, 1998
U.S. Pat. No. 5,856,092, issued Jan. 5, 1999
U.S. Pat. No. 5,858,652, issued Jan. 12, 1999
U.S. Pat. No. 5,861,244, issued Jan. 19, 1999
U.S. Pat. No. 5,863,732, issued Jan. 26, 1999
U.S. Pat. No. 5,863,753, issued Jan. 26, 1999
U.S. Pat. No. 5,866,331, issued Feb. 2, 1999
U.S. Pat. No. 5,866,336, issued Feb. 2, 1999
U.S. Pat. No. 5,866,337, issued Feb. 2, 1999
U.S. Pat. No. 5,900,481, issued May 4, 1999
U.S. Pat. No. 5,905,024, issued May 18, 1999
U.S. Pat. No. 5,910,407, issued Jun. 8, 1999
U.S. Pat. No. 5,912,124, issued Jun. 15, 1999
U.S. Pat. No. 5,912,145, issued Jun. 15, 1999
U.S. Pat. No. 5,912,148, issued Jun. 15, 1999
U.S. Pat. No. 5,916,776, issued Jun. 29, 1999
U.S. Pat. No. 5,916,779, issued Jun. 29, 1999
U.S. Pat. No. 5,919,626, issued Jul. 6, 1999
U.S. Pat. No. 5,919,630, issued Jul. 6, 1999
U.S. Pat. No. 5,922,574, issued Jul. 13, 1999
U.S. Pat. No. 5,925,517, issued Jul. 20, 1999
U.S. Pat. No. 5,925,525, issued Jul. 20, 1999
U.S. Pat. No. 5,928,862, issued Jul. 27, 1999
U.S. Pat. No. 5,928,869, issued Jul. 27, 1999
U.S. Pat. No. 5,928,870, issued Jul. 27, 1999
U.S. Pat. No. 5,928,905, issued Jul. 27, 1999
U.S. Pat. No. 5,928,906, issued Jul. 27, 1999
U.S. Pat. No. 5,929,227, issued Jul. 27, 1999
U.S. Pat. No. 5,932,413, issued Aug. 3, 1999
U.S. Pat. No. 5,932,451, issued Aug. 3, 1999
U.S. Pat. No. 5,935,791, issued Aug. 10, 1999
U.S. Pat. No. 5,935,825, issued Aug. 10, 1999
U.S. Pat. No. 5,939,291, issued Aug. 17, 1999
U.S. Pat. No. 5,942,391, issued Aug. 24, 1999

PUBLICATIONS

Alonso, A., Martin, P., Albarran, C., Garcia, O. & Sancho, M. Rapid detection of sequence polymorphisms in the human mitochondrial DNA control region by polymerase chain reaction and single-strand conformation analysis in mutation detection enhancement gels. *Electrophoresis* 17, 1299–1301 (1996).

Attar, R. M. et al. Genetic approaches to study rel/NF-κB/IκB function in mice. *Seminars in Cancer Biology* 8, 93–101 (1997).

Beg, A. A., Sha, W. C., Bronson, R. T., Ghosh, S., Baltimore, D. Embryonic lethality and liver degeneration in mice lacking the RelA component of NF-κB. *Nature* 376, 167–170 (1995).

Doi, T. S. et al. Absence of tumor necrosis factor rescues RelA-deficient mice from embryonic lethality. *Proc Natl Acad Sci USA* 96, 2994–2999 (1999).

Franzoso, G. et al. Requirement for NF-κB in osteoclast and B-cell development. *Genes Dev* 11, 3482–3496 (1997).

Ganguly, A., Rock, M. J. & Prockop, D. Conformation sensitive gel electrophoresis for rapid detection of single-base differences in double-stranded PCR products and DNA fragments: evidence for solvent-induced bends in DNA heteroduplexes. *Proc. Nat;. Acad. Sci.* 90, 10325–10329 (1993).

Ghosh, S., May, M. J. & Kopp, E. B. NF-κB and rel proteins: Evolutionary conserved mediators of immune responses. *Ann Rev Immunol* 16, 225–260 (1998).

Hu, Y. L. et al. Abnormal morphogenesis but intact IKK activation in mice lacking the IKKα subunit of IκB kinase. *Science* 284, 316–320 (1999).

Hughes, A. E. et al. Mutations in TNFRSF11A, affecting the signal peptide of RANK, cause familial expansile osteolysis. *Nature Genet.* 24, 45–48 (2000).

Iotsova, V. et al. Osteopetrosis in mice lacking nf-kappa-b1 and nf-kappa-b2. *Nature Med* 3, 1285–1289 (1997).

Israël, A. The IKK complex: an integrator of all signals that activate NF-κB? *Trends Cell Biol* 10, 129–133 (2000).

Jin, D. Y. and Jeang, K. T. Isolation of full-length cDNA and chromosomal localization of human NF-kappaB modulator NEMO to Xq28. *J Biomed Sci* 6, 115–120 (1999).

Jouet, M. et al. Linkage analysis in 16 families with incontinentia pigmenti. *Eur J Hum Genet* 5, 168–170 (1997).

Kehayova, P. D., Bokinsky, G. E., Huber, J. D., Jain, A. (1999) A caged hydrophobic inhibitor of carbonic anhydrase II. *J. Amer. Chem. Soc.,* 1: 187–188.

Landy, S. J. & Donnai, D. Incontinentia pigmenti (Bloch-Sulzberger syndrome). *J Med Genet* 30, 53–59 (1993).

Lewis, R. A., Esposito, T., Ciccodicola, A., D'Urso, M., Smahi, A., Heuertz, S., Munnich, S., Vabres, P., Woffendin, H., Kenwrick, S. Mutation analysis of the DKC1 gene in Incontinentia pigmenti. J Med Genet 36, 860–862 (1999).

Li, M., Ona, V. O., Guegan, C., Chen, M., Jackson-Lewis, V., Andrews, L. J., Olszewski, A. J., Stieg, P. E., Lee, J., Przedborski, S., Friedlander, R. M. Functional role of caspase-1 and caspase-3 in an ALS transgenic mouse model. Science 288: 335–339 (2000).

Li, Q. T. et al. IKK1-deficient mice exhibit abnormal development of skin and skeleton. *Genes Dev* 13, 1322–1328 (1999).

Li, Y. et al. Identification of a cell protein (FIP-3) as a modulator of NF-kappaB activity and as a target of an adenovirus inhibitor of tumor necrosis factor alpha-induced apoptosis. *Proc Natl Acad Sci USA* 96, 1042–1047 (1999).

Lopes, J. et al. Sex-dependent rearrangements resulting in CMT1A and HNPP. *Naure Genet* 17, 136–137 (1997).

Lupski, J. R. Genomic disorders: structural features of the genome can lead to DNA rearrangements and human disease traits. *Trends Genet* 14, 417–422 (1998).

Mercurio, F. et al. IκB kinase (IKK)-associated protein 1, a common component of the heterogeneous IKK complex. *Mol Cell Biol* 19, 1526–1538 (1999).

Parrish, J. E., Scheuerle, A. E., Lewis, R. A., Levy, M. L. & Nelson, D. L. Selection against mutant alleles in blood leukocytes is a consistent feature in Incontinentia Pigmenti type 2. *Hum Mol Genet* 5, 1777–1783 (1996).

Poutska, N. S., Woffendin, H., Kenwrick, S., Esposito, T., Ciccodicola, A., Bardaro, T., D'Urso, M., Smahi, A., Munnich, A., Herman, G. E., Lewis, R. A. The human homologue of the murine Bare patches/Striated gene is not mutated in Incontinentia Pigmenti Type 2. *Am J Med Genet* 91, 241–244 (2000).

Rice, N. R., MacKichan, M. L. & Israel, A. The precursor of NF-κB p50 has IκB-like functions. *Cell* 71, 243–253 (1992).

Rivera, V. M., Wang, X., Wardwell, S., Courage, N. L., Volchuk, A., Keenan, T., Holt, D. A., Gilman, M., Orci, L., Cerasoli, F., Rothman, J. E., Clackson, T. (2000) Regulation of protein secretion through controlled aggregation in the endoplasmic eticulum. Science 287: 826–836.

Ropp, P. A., Thorp, H. H. (1999) Site-selective electron transfer from purines to electrocatalysts: voltammetric detection of a biologically relevant deletion in hybridized DNA duplexes Rothwarf, D. & Karin, M. The NF-κB activation pathway: a paradigm in information transfer from membrane to nucleus. http://www.stke.org/cgi/content/full/OC_sigtrans;1999/5/rel Oct. 26 (1999).

Rothwarf, D. M., Zandi, E., Natoli, G. & Karin, M. IKK-γ is an essential regulatory subunit of the IκB kinase complex. *Nature* 395, 297–300 (1998).

Rudolph, D. et al. Severe liver degeneration and lack of NF-κB activation in NEMO/IKKγ-deficient mice. *Genes Dev.* 14, 854–862 (2000).

Sambrook, Fritsch, Maniatis, *In: Molecular Cloning: A Laboratory Manual*, Vol. 1, Cold Spring Harbor Laboratory Press, Cold Spring Harbor, N.Y., Ch. 7,7.19–17.29 (1989).

Shen, L. X., Basilion, J. P., Stanton, V. P. (1999) Single nucleotide polymorphisms can cause Smahi, A. et al. The gene for the familial form of incontinentia pigmenti (IP2) maps to the distal part of Xq28. *Hum Mol Genet* 3, 273–278 (1994).

Subramanian, A. Ranganathan, P., Diamond, S. L. (1999) Nuclear targeting peptide scaffolds for lipofection of nondividing mammalian cells, 17: 873–877.

Subramanian, G. Hjelm, R. P., Deming, T. J., Smith, G. S., Li, Y., Safinya, C. R. (2000) Structure of complexes of cationic lipids and poly(glutamic acid) polypeptides: a pinched lamelar phase. J. Amer. Chem. Soc. 122:26–34.

Takeda, K. et al. Limb and skin abnormalities in mice lacking IKKα. *Science* 284, 313–316 (1999).

Van Antwerp, D. J., Martin, S. J., Kafri, T., Green, D. R. & Verma, I. M. Suppression of TNF-α-induced apoptosis by NF-κB. *Science* 274, 787–789 (1996).

Weil, R., Laurent-Winter, C. & Israel, A. Regulation of IκBβ degradation—similarities to and differences from IκBα. *J Biol Chem* 272, 9942–9949 (1997).

Woffendin, H., Jakins, T., Jouet, M., Stewart, H., Landy, S., Haan, E., Harris, A. et al. X-inactivation and marker studies in three families with Incontinentia pigmenti: implications for counseling and gene localisation. Clin Genet. 55(1), 55–60 (1999).

Yamaoka, S. et al. Complementation cloning of NEMO, a component of the IκB kinase complex essential for NF-kappaB activation. *Cell* 93, 1231–1240 (1998).

One skilled in the art readily appreciates that the present invention is well adapted to carry out the objectives and obtain the ends and advantages mentioned as well as those inherent therein. Sequences, mutations, complexes, methods, treatments, pharmaceutical compositions, compounds, kits, procedures and techniques described herein are presently representative of the preferred embodiments and are intended to be exemplary and are not intended as limitations of the scope. Changes therein and other uses will occur to those skilled in the art which are encompassed within the spirit of the invention or defined by the scope of the pending claims.

What is claimed:

1. A method to detect Incontinentia Pigmenti in a human comprising the steps of:
    obtaining a sample from said human; and
    analyzing said sample for an alteration in a nucleic acid of SEQ ID NO:1.

2. The method of claim 1, wherein said alteration is a mutation, wherein said mutation is selected from the group consisting of a deletion, an insertion, a point mutation, a rearrangement in said sequence, and a combination thereof.

3. The method of claim 2, wherein said point mutation is selected from the group consisting of a nonsense mutation, a frameshift mutation, a missense mutation, a splicing-relate mutation, and a combination thereof.

4. The method of claim 1, wherein said alteration is located in a regulatory region, an exon, an intron, an initiator codon, a stop codon, exon/intron junction, a 5' untranslated region, a 3' untranslated region or a combination thereof.

5. The method of claim 1, wherein said analyzing step comprises a method selected from the group consisting of hybridization, SSCP, heteroduplex analysis, sequencing, polymerase chain reaction, electrophoresis, and a combination thereof.

6. A method to detect an alteration in a nucleic acid of SEQ ID NO:1 in a human, comprising the steps of:
    obtaining a sample from said human; and
    analyzing said sample for said alteration.

7. The method of claim 6, wherein said alteration is a mutation, wherein said mutation is selected from the group consisting of a deletion, an insertion, point mutation, a rearrangement, and a combination thereof.

8. The method of claim 7, wherein said point mutation is selected from the group consisting of a nonsense mutation, a frameshift mutation, a missense mutation, a splicing-relate mutation, and a combination thereof.

9. The method of claim 6, wherein said alteration is located in a regulatory region an exon, an intron, an initiator codon, a stop codon, an exon/intron junction, a 5' untranslated region, a 3' untranslated region or a combination thereof.

10. The method of claim 6, wherein said analyzing step comprises a method select d from the group consisting of hybridization, SSCP, heteroduplex analysis, sequencing, polymerase chain reaction, electrophoresis, and a combination thereof.

11. The method of claim 6, wherein said human is selected from the group consisting of an affected individual, a carrier individual, and a noncarrier individual.

12. The method of claim 6, wherein said analyzing step further comprises a technique selected from the group consisting of PCR analysis and Southern blot analysis.

13. The method of claim 12, wherein a probe for said Southern analysis is a nucleic acid SEQ ID NO:3, or fragments and derivatives thereof.

* * * * *

SEQUENCE LISTING

```
<160> NUMBER OF SEQ ID NOS: 79

<210> SEQ ID NO 1
<211> LENGTH: 23106
<212> TYPE: DNA
<213> ORGANISM: Human

<400> SEQUENCE: 1
catggcccTT gtgatccagg tggggaaact aaggcccaga gaagtgagga ccccgcagac      60
tatcaatccc agtctcttcc cctcactccc tgtgaagctc tccagcatca tcgaggtccc     120
atcaggtggg gaaagatgct gttccaggcg cacactagtc tacaaggcca gagctttctg     180 gaaggggca gtaagtacct cggctccctt tctggtaggg gtgggagtcc tgagaaggca     240
ggaagtggcc cacttggtaa ctctgaggtg ccatcagggc ccccaggaag gaagctgggt     300
```

```
gtgtgggcaa gtgtgaggta agctggccag ggaggaggaa gggacagagg aaggccacgt      360
gggtccagcc tgccccaggg tgtcctgctt gcccaggctg tgggtctgcc agccacttgc      420
ctgctttcag tttctaggtc atgctgagct tgttcccaac tcggggctcc gggcatttgc      480
tcttccttct gtgtttgtgc tctcccggcc ctctttgtgg gatctatgcg ctttggggga      540
ctggggacac agggcccatg tgtatcttct gaaacacacg tcagcctgaa ctcttgctgg      600
tctgcttact tgccgtggtt ccctggccgc aatagcacat aggtcccatg aggagggcag      660
ggactggctg ctgtggccca gaagtaccca atcgctgtct gctcaatgaa cggagaatgg      720
gctgctttcc tggaacagca gattctagga tcacgtgccc tcaagtgcca ccctgcctac      780
ctcccgcacc gagtgaggca tcaggcgtgg aagaagcctg ggagccggag ctgttccagg      840
tgctgcctga gcacgccacc tcccatctcc cccccagcag gaagaggaaa aaacaaacca      900
cgaggctctt cagagagagg accccttgtc ccctacccac agtgctggag ctggcacttc      960
ctatttctgc tttgaaagcc tcaggttgtc actctcagaa cagaggagag caaaggggaa     1020
ccctactgat ttcaacaaaa caaagttgcc caacccgaag ctggccacag cggaggcag     1080 tgaaatgaca aaatcagctt ggaaaagcct aaggaccctg ggccctcgtt tcaaaagctg     1140
tcatttgcta cacgaaatgc tgaggttcag gaaaaggaag acacttgctc caactcacac     1200
agcaagcttg gatgctctca atgaggtgtc taataagagc tgaaggccag gagtcataag     1260
ctatcattgt ggcctgggtt gctctgttgc agtgccttgt gacagcatgg ggtggggatg     1320
gagaaagcaa cctcagttac cttctcctcc agtctgcttc ttggactaag ggtttaacgg     1380
tcagagtcct ggctgttaag gtttgtggct gatgcaggta tggctctttt tattttttatt     1440 tttttgagat ggagtctcac tcactccgtc acccaggatg gagtgcaatg gtgccatctc     1500
agctcactgc aacctccacc tcctgggttc aagcgatttt cctgcctcag cctcccaagt     1560
agctgggatt acagatgggt gccactacac ctaactaatt tttgttattt ttttttttt      1620 tttgagatgg agtctcactc tgtcacccag gctggaatgc agtgttgcga tttctgctca     1680
ctgcaagctc cgcctcccga gttcacgcct tctcctgcc tcagcctcct gagtagctgg      1740
actacaggtg cccacaccag gcctggctaa ttttttattt agtagagacg ggatttcacc     1800
atgttagcca ggatggtctc aatctcctga cctcatgatc cacccgcttc agcctcccaa     1860
agtgctggga ttacagacgt gagccactgc gcccggcctt tttgttttgt tttgttttga     1920
gacagagtct cgctctgtcg ccaggctgga gtgcagtggc gcgatctcag ctcactgcaa     1980
cctctgactc cctgattcaa gcgattctac tgcctcagcc tactgagtag ctgggactac     2040
aggcacgcac caccacgccc agctaatttt tgtattttta gtagagatgg ggtttcacca     2100
tgttggccag gatggtctcg atctcttgac cttgtgatct gcccaccttg gcccccaaa      2160 gtgctgggat tacagatgtg agccactgcg cccagccaat ttttgtattt taagtagaga     2220 ctgggttttcg ccatgttggc caggctggtg tcaaactcct gacctcaggc gatccacctg     2280
cctcggcctc ccaaagtgct gggaatacag gcgtgagcca ccgtgcccgg ccaggtatgg     2340
ctcttctgag gggaccaggc tgggctgggg gctgaggcca agcccaatct actgtgggct     2400
ccacctggta cctctcctgg gtctcaggct tatggggagt cagaggacaa tggcccctcc     2460
ttactctgcc actggcagag cccttctccc tcggctgcct cctcattccc ttttggctct     2520
ccttttctaa gttctgatca gaagtacaaa ggtgtcaagg agtaggtttg acaaagtgtg     2580
acagtgcgtt gttctatgtg aacaaagaac cactgagctc agccagcact gagggcgca      2640 cgatgtggaa gaactaacta gttttgatag agctcctgct caaggttaca aggtaagtta     2700
```

```
atggcaaaga tggtcataca gtaatgagca gagagattct tgagtgcatc cagggttaaa    2760
agtgaaaact gagaccacgt gtaatttgag atgaagccct tgttccacca gcccctgcac    2820
agtctcactg ccccatggga cacagggggag ggtgctctag tctcgggcga tggctgtcct    2880
aggaccaccc ctccctcccc tcccatggaa atcctcatgc tatactattc ttttgtcttt    2940
cctatgagtg cagaatggcg gttctacaag ctggacaatt ggggccaggt ggggtgaggc    3000
agagctcctt ggtaggcttt cgaaattgag gcaaagagac agtgttcaaa gaaaagctaa    3060
gtgtttgtat cgacggaact tgaagtgtta gtgaagaggc agagatcagg cctcagatcc    3120
tgcctttgga actcatttgt taaggcatga acaggtctga aaaaactaca gaatgaatag    3180
cattccctgt tttccccaag aagtccatct agacagtccc taaagagcct gcaactccag    3240
gattaagggc tacattcagc ggctaggcac agggttcaga aacgtcctgc agccgggcgt    3300
ggtggctcat gcctgtcatc ccagcacttt gggaggccga ggcgggcgga tcacttgagg    3360
tcaggagttt gagaccagcc tggtcaacat ggtgaaactc cgtctctact aacaatacaa    3420
aaattagccg ggtgtggtgg tgcatgcctg taatctcagc tacttggggg gctgaggcag    3480
gagaatcgct tgaacccagg aggccgaggt tgcagtgagc caagatggcg ccactgcacc    3540
ccatcctggg cgaccagagc aaaactccgt ctccaaaaaa aaaaaaaaaa aaaagtcttg    3600
caagtgcata tgcacaccag gtagagccgg gatgatcctg gcgcactagc aggagcggga    3660
ggaggagctc aacttagcag agcctgtggg gccctgcaac aattagttgg aaaagctgag    3720
gcatggagca ggcacttcct ggcttttaag attgggcct gggagatact caccgatgca    3780
cccatgatga tgaatatgtg tgtatccgac tgatggaagg catcgccctg gaaaagctct    3840
tcccgcagga tcccgcacac ctgggtccgg ctcaggccca cctgctctgc catgacgctg    3900
tctggtggaa gaaaggctcg ttaacaaggc agaagaacag gagagcattg agaagttagc    3960
ccctttcttg agagttcctc tggggtctca caccagggtg acacctgatt gcccaaatca    4020
ctccttgtga acggctgggc attggggagt ggttgatggg ttagaaactg ctggctctgg    4080
gctccagcca ctctctccta ggcagccttc attcaggggtg tacattacaa aattactcaa    4140
agcattggtg tattccgact acagcatcaa ttctggacaa ccgagtaaaa tccttgtggg    4200
gcatggaact gcgtgcccag gaccatctca ttcccgactg tagcgggaac tccacaatga    4260
cctggagcat gggagatggt gcagatgctg gagttcagct ccagcccctcc ccttgccaag    4320 ctgggtgacc ccgtcggca agtccccttc gctctcgggg tctcagggggc tcaagagagg    4380 aggtgcgggg tataaaggga ttggttaaga ccctctcgat tctgctcggt tctcaagcac    4440
aacaaacagc gtgtattttta ccgccgcgcg gcgcagcgcg ggacagtacg ctcctccgcc    4500
tgcgcggcgc ccgcccggcc ggttacctgc gcttcgtcgt cgtcgccctc cgcgctcgca    4560
gccccgaagt gtacgaccgt ttccgggggc tgagcccccgc cggcccattt aatcggcggg    4620
ggcgggggcg ggcgcctggg ctgagcggac ccgcctcagg cgaggcgtgc ggggcggggc    4680
ctcggccacc acccctcgtg cgggcgggggc ggggcgaggg caggtgcgcg cgcatcccag    4740
gccagcccct gcctctcggg cacctgcgct ggaggccggc ccgccggctg cctgccatac    4800
ccgctgccgc tgtctgcat ccccaattcc ggcgggcacg ggtgcagctc cgcgtagtgc    4860
tcccgcatcc ccatcgccgg cccggcccccg ccctactgt ccggtttccc cgcctgcccc    4920
ggcggcctcg cgcgctcgcg gagggctcca cttccgccgg cagcgtggcc acgcctcctc    4980
tgggctgtcc ctcggctcct gggcgggggcc ttctgccgcg ccactccccc gggaaccctc    5040
```

```
gcctgttcgc gggtcaagcc ggccctattg ggcagtctct tcttgattcc tcccccggag    5100
agggcggggc ggccgagcgc cccgaggcta gacgccgccg tccgagagac gagggggcgt    5160
gtaggcggtg acgccctgca aagtggccgg cgtgcttatc attaccgagc ttccgcgggc    5220
ctgcagagcc tggcggactc agacttctct ccggagcggg atgcggccct accgcggcct    5280
cacacttctc gccggcttcc cgagttcccg ggggcggggc ttgtgttttt acttccggat    5340
cccacagcta tgacaccgga agccggaagc gtggtaggga agggcgaccg cgaaactggg    5400
actttctcgg agcgccgggg ccctaccagc gttcacagtc cgccgctccc acccttctca    5460
cgtctgacgg actctgctga caggtgtggt ccttttcccc aaagacaggg ttccatccgt    5520
gggcgttccg ccgcctccga aacttccccc ggacgttcag gctccccct cttttttggg     5580
ccccagcccg ttcctgctcc gcgcttctgg agcactggcc aaggcgggcc gattcaggac    5640
ccaggttact tgggcggcga gctggactgt ttctactcct ccctcctcct ccactgcggg    5700
gtctgaccct actccttgtg tgaggactcc tctagttcag agacatattc tgttcaccaa    5760
acttgactgc gctctatcga ggtcgttaaa ttcttcggaa atgcctcaca tatagtttgg    5820
cagctaggta tctgatttca tatgcctgtt tgctcgtttt gcaagacaac atctgcctat    5880
cgtcatactg tttctgtgat ctgagaatga atgggctctc ctggcacatt agaggaatag    5940
cacggaggtc actatagctg gagcagagtg agggagggga gcacagttgg agaggaaggg    6000
atggggaacc cgatggtaca gggccttgta ggccgttgta gggagattgg cttttacgca    6060
gaaggcaacg gggatccatg gtagggttct cagtagagga ggaatgtgat cggaattacg    6120
tcttacactg atcgttctag cagtggtggg gagaccagac catagtgggc aagggtaaaa    6180
gaagggtggc gtggtaagag gtaattgcag taatccagct cagagacagt gctttgagca    6240
ttttattatt ggaaatttca aaaatgtacg aaagtagaaa aatgagtata gtaaatcttt    6300
ttggtttgtt tgtttttgag agatgggagtc tcgctctgtc gcccaggctg gagtgcagtg    6360
gcatgatctc agctcactct aacctcctcc tcctgggttc aagcgattct cctgcctcag    6420
cttcccaggt agctgggact gcaggcgtgc gccactacgc ccagctaatt tttgtatttt    6480
tagtagagac ggggtttcac tatatgttgg ccagtctggt cttgaactcc tgacctcagg    6540
tgatctgcct gcctcagact cccaaagtgc tgggattaca ggtgtgagcc actgcgctcg    6600
gccagtatag taaatcttac attcacagct accaacttca acaattgaag gtatcaactt    6660
ctgactaatt tgtttatat ccctcgcaat cctctcccat tattatttta tttctttttc      6720
tttctttctt tcttttttt ttttttttga cagaatct cgctctgtca ccaggctgga       6780
gtgcagtggt gtgatctcca cccactgcaa cttccgcctc ctggattcaa gcgattcttc    6840
tgcctcagcc gctgggacta cagttgtgca ccaccacgcc cagctaattt ttgtattttt    6900
agtagagatg ggtttcatc atgttggcca ggatggtctt gatctcttga ccttgtcatc      6960
cgcccgcctc ggcctcccaa agtgctggga ttacaggcat gagccaccgc gcccggcctc    7020
tttttttgag acccagtctc actctgtcgc ccaggatgga gtgcagtggc acgatcttgg    7080
ctcaccgcaa cctccatctc ccaggtttga gcgattctcc tgcctcagct cccaaatag     7140
ctgggattac aggcatgcac catcactccc agctattttt tttttttgt attttggta      7200
aatacagggt tttgtcatgt tggccaggct ggtcttgaat tctgacctc aagtgatcca     7260
cttgccatga cctcccaaag tgctgggatt acaggtgtga accaccatgc ctggccacca    7320
ctattatttt caataacagc ttgagatatc attagcatgt cacacagttc atccatttaa    7380
agtgtacaat tcaatggttt gttgtatgta tattcacagg acattttcgt caccccctcaa   7440
```

```
agaaacccca tacccttag ctcagcttat cttcccctca gccctaagtg gcactcccca    7500
gcaatcttta atccactta tgtctctgtg gatttgcctg ttgtagacat cttatataaa    7560
tagactcata caatgtttaa tcttttgtga cttgtttatt tctcagcata ttttcaagat   7620
ttgttcatgt tatagcatgt ggatgtacta gattttgttt attcatagtt gatggacatt   7680
tgggttttcc actctctggc tgctatgagt aatgctgcta caagcattca tgtgacaca    7740
tgtgttttca tttctctccg gtatatacct aggagttttc ccattatttg gaggtgaatt   7800
cagacatcat ctttaaacat ttaagtgtgc ctctctctaa gacaggactc tgaaaaacaa   7860
ccacaatatc attatgacac ctaaaatagt taatgttaat tgctcagtgt gatcagatcg   7920
gttgggggat acattttaac aggatttctt gatggattag atgtgctctt gtgtgtgtgt   7980
gtgtgtgtgt gtatgtgtgt gtgtgtgtgt gagagagaga gagaatcgaa aaagaccttt   8040
tgcagctgaa ggatggattc gccatcagct gataccaaga agcccttggg tagatctggg   8100
tttgggact gtcggaggtc ttagaaaggt tcgttttgag aaggctacta gataaccaag    8160
tagaaatgtc gagtttgata atgaatgtg gagtttagaa aagaggtcta attaagcatc    8220
aagattggag ttcaaggcat gagactggca gaattcctgt gggagtgaat gaagttacag   8280
agaagaagat gtcctaggac agagccctgg gcagcccaac atgaaggatg ggaacccagt   8340
gagagtgcct gggcaggagt agccagcaag ataggagga aaccaggaga aggggctgtt    8400
ctgaaagcca agggtggagt gcagtggcac aatctcagct cactgcaacg tccgcctcct   8460
gggttcaagc gattctcttg cttcggcctc ccgagtagct gggactacag gcgcgtgtca   8520
ccacactctg ctaattttt gtatttttt tttttgagat ggagtctcgc tctgttgccc     8580
aggctggagt gcagtggcgc gatcccgggt tcacgccatt ctcctgcctc ccgggttcac   8640
gccattctcc tgcctcagcc tcctgggtag ctggggctac aggcgcccgc taccatgcct   8700
ggctaatttt ttgtattttt agtagagaca gggtttcact gtgttagcca ggatggtctc   8760
aatctcctga cctcatgatc cacccgtgtc ggcctcccaa agtgctggga ttacaggcgt   8820
gagccaccgt gaccggcaat ttttttttt ttttttttag tagaggcagg gtttcaccgt    8880
gttagccagg ctggtctcga tctcctgacc tcatgattgg cccgcctcgg cctcccaaag   8940
tgctgggatt acaggtgtga gccactgcgc ccggccagac attttaatct cacagttctg   9000
gagactagaa gtccaaaacc aaagggttag caagcacaca ccctcaaagg ctctaagagg   9060
gcaatcctcc cttgcctctc ccaagcttct gccccattta ttcctgggct tgtggctgcc   9120
tcactccagt ctccgaggca gtcccgacat ggcctcctcc ccttgcgtct ccctctggct   9180
tctctcttct gtctctcata aagacacgtt gttggattta gggcccaccc acgtcaccca   9240
gaatgatctc atcttgagat cctacatctg caaagaccct tttcccgaat cacatatgtt   9300
tcagggggtta gaacatgggc atatcttttc gggggctac cattcagccc actacactgg    9360
atgaggggcc ggtaccctcc acttctcctg cttggaggtg tgtaggggat caggattccc   9420
agcatactga catctccctc cacaaacagt cttgtcccga ctctcccatc tctggtgaaa   9480
ttcttctatt tccagcctgg agctaggcct tttcaagtcc cacatgggtg gtccagcacc   9540
tcccttttgga atgggagtat ctgctacccc ttagactgaa aacccacttt agcatcctga   9600
tacactaggt gaattatcag cattctgttt aaaatgtagc cccagaactc ataggctttt   9660
tctgctgggt aaggatgtgg gtctcctgtg actcccctgc tgcctttctc tttcagccct   9720
tgccctgttg gatgaatagg cacctctgga agagccaact gtgtgagatg gtgcagccca   9780
```

```
gtggtggccc ggcagcagat caggacgtac tgggcgaaga gtctcctctg gggaagccag   9840
ccatgctgca cctgccttca gaacagggcg ctcctgagac cctccagcgc tgcctggagg   9900
agaatcaaga gctccgaggt gaggaaagag tcagggatc  cagccctgct gaggggaagg   9960
cgtcttctcc ccacctgcac ctctgcgttt cctgggcctg gggtggggat gtgctgccct  10020
ccctcttggt ttcaggaagt agactctgag atgcagatta gcggggagga agtttagcat  10080
gctctcagga ccagtactgg gaagggaaag gagggacagg ggaagaagcc agggagggca  10140
gagggagaag cacgctgccg ggtaggctcc aggacagcct tgctggatct tacagggagc  10200
tctggagctg gaatgaacct tccaggttgg accaacatgt ccaggcctct gtgtccctgc  10260
actgagcact catgaagtgc tgtccatcct gggacagggc agagtcggcg ctcccgaaga  10320
ggcgtggtct gcccagagag ggggtggggc ctgtcctgga aatgggcggg gcatgccctg  10380
gtagagcggc gtggtctgtc ttgggaagga aggtgcgtgg cccccacagg caacattcct  10440
ctggggcaat cccggcgcac acctcagcgg aggtgaaggc tgacttccca cacccagtgg  10500
ctgggactgg ggagttcttt cctagactgc catccgggcg cccctcaccc tcttgctgct  10560
cagctccagg tcgcatgggt tcagggctca gctgcacgct cctgcccgcg ccctgggcgt  10620
gatggcaccc ccagcccctg ccattcttcc ccctcacccc ctctccctgc cactgctctg  10680
ccttgccctg ggttagcctg gcggggccag gtggcacccg ccatatactc ttgccttct  10740 gctgcggggg ccttctaagc ctcgggtccc agagctgcag ggaggggcgg catagactcc  10800
ccacatggct cactgggtgt ggtgggcct  gtagcccttt ttgtttcatc ctttggttcc  10860
tgctggggac tcaggcctaa gtgtccaccc catcgtggag acaacaccc  cttccttgca  10920 ggagtcatcc ctgagctggc agcttcaatt ggctctccgt gtcctggctg gctggcagct  10980
cctgggcgag gtggcatgtg ccgtgactac tagagatcgc tgtcatgggc ccactccccc  11040
gccttctttg ctggactgtg gtccgagatg ttatgtgggg ctctgtgctg acaagtcaca  11100
tagtctgtag gcttcagaga gtggctctgg ctgacacccc gtgggcagag acaagaccca  11160
tgcctgcgat gtgtctcctc ttactgtcaa ggcaaatcac cttttccttcc atggaggaag  11220 gggtcagtgc agtcagcttg ctgtcagggg gctgcttggt ctcctcgacg gtgaggctga  11280
attggagagg ccctgctgga gcatggagac ccaacatgac ctgcctgttc caggacaggg  11340 tccccacct  cagtgccatc ggcacctggg gctggagaat tctcttgtac gttgtagggt  11400
gtggagcaga gtccctggcc tgtacctgct agatgccagt agcacctgtc ctgttgtgac  11460
aactaccaat atccccaga  tatttattgc caaatgaccc ctgggggata cagttgtccc  11520
tggtgagacc cacttgtatt gggatcttca gagcacttgg tgcacagaga ggtgacagtt  11580
agactggggg cttctgctca tccccaggag agtgctctat tgaggggac  ttgagggtga  11640 gtgttgcagg ccagctgtgc agggaccctg gcacagcgta tggcgccctt gcttcccttc  11700
caggctgtgt gttcagtgca gcagcttccc tcgggctcca gggacacaag gaggcctcaa  11760
ggctgtattg actccccctg ctccgcctga cctgagcttt gtgggtggca ggtgaaactt  11820
ggtagctcca tgtgtcaggc cctgggccaa gcccctaagg gcccagaaga tgtctgtccc  11880
ccaagatgta catgcttatg tccatggagg aggctgtact tagaatgttg agggagagat  11940
tcacgaagaa gttgcatgtc tctagtgtgt gactccacta gtgtgagaca tgtccagaag  12000
tggccaatct gcagaggcag atgcagatga ggagggtgct gggggagcga ctgcttatgg  12060
ggtcccggaa ctgttctgga attagatagt gcggatggtt gcacaacctg atggatacac  12120
cgaaaactgc tgaattagtt aaaatagtga atttgatgtc atgtgaattt tacctcagtt  12180
```

```
cagaacattt tttaaaagac aagttgccag ccaggtgcag tggctcatgc ctgtaatcca    12240
agcactttgg gaggcccagg cgggggatc  acctgaggtc aggagtttga ccagcttg      12300 gccaacatgg tgaaacccca tctctactac aaaaattagc tacagacgtg gtggcgggca    12360
cctataatcc cagctacttg ggaggctgag gcagggagaa ttgcttgaac ccaggaggtg    12420
gaggttgcag tgagctgaga tcgcgccact gcactccagc ctgggcgaca gagcgagagt    12480
ctgtctcaaa aaaaagaca  agttgcagat gagctgagct ttgggcagag caagcgggat    12540
tctgatgggg ggtggatgtt gcgctcgtca gcaggcaata gttagttggt tgagggtttt    12600
gatcacgggg tagctactgc ctgccccatt ttatccagct ctgtagttgc tatagagttg    12660
ctagaacctt ggcacatcac ttatcagttt tgtcacctca gatggcttct tcactacttg    12720
gggtgtctcc tgggtgtggg gctctccttc ctgtggcctc tgctgactgc ctggcactgg    12780
cacacatgct ctggtgaggg gaggaccagc ggttttccc  gtttgttttc tgcttcctcg    12840
tttaaccctc ctcgtcttgt aagatgaatg ttcttgtctc tgttcactat gcagatgagg    12900
actttgaggc tcagagacgc cactaacttg cctggtccaa gccttttggg cctctcaggc    12960
tgcagccagc aatgctgcag tgaagtttgc ctgggaggct gaccctagga gtctgcaggc    13020
gtgttaggac ccccgatcta gaagacagca gagatgtagg ccagggagga ccaataccga    13080
gcatctgagg gcaggcacac ctcagactga ccagaataca aatgaattcg agtcacttac    13140
aaacaaagtg gcataaggcc aggcacagtg gcaacacatg cctataatcc cagcactttg    13200
ggaggccgag gtgggaggat tgcttgaggc caacgatgtg agaccagcct gggcaacata    13260
gcaagacctt gtctctacaa aaataaaaat tcaaaaaagt ggcatttaac acatactttt    13320 tttcttttt  ttgagacaga gttttgctct gtcccccagg ctggagtgca atggtgtgat    13380
ctcggctcac tgcaacctcc acctcccagg ttcaagtgct tctcctgcct tagcctccca    13440
agtagctggg attacaggcg tgtgccacca caccgggcta atttttgtat ttttattaga    13500
gacggggttt caccatgttg gccaagctgg tctggagctc ctgacctcag gtgatccacc    13560 cacccttggcc tcccaaagtg ctgggattac aggcatgagc cacagtgcct ggccaacacg    13620
tacttttaag tgaagctgat gtgtttggtg ttattttctt gcagaaagtg agggcatta     13680 gtgtaaagga ttttggaagt gtttaaagaa acaaaaggga gtgttgagac gccatccacc    13740
cctgagagaa gctgcgtggt attatggcgg gtgggggcac caggatgggt ggccccactt    13800
ctggcctctg acttcctgag cctcaggccc atgtgggccc aggcagggcc cggcaggccg    13860
ggctgcccag ctcccctcca ctgtcccctc tgccaccaga tgccatccgg cagagcaacc    13920
agattctgcg ggagcgctgc gaggagcttc tgcatttcca agccagccag agggaggaga    13980
aggagttcct catgtgcaag ttccaggagg ccaggaaact ggtggagaga ctcggcctgg    14040
agaagctcga tctgaagagg cagaaggagc aggctctgcg ggaggtggag cacctgaaga    14100
gatgccagca ggtagtcggg gcagggccag gttctgaaaa cccgcggtga cgccagtgtt    14160
ccacaaggga acccgtggtc gggtccccc  aaagcaccct gggctcagt  gctgtgccgg    14220 gagggctcgg aactcagaaa agccgtcaca ctcccagttc cggtttatta caaggaaagg    14280
acacaggtta cggtgagcga aggctcaggg cgcacagggc gggctccagg agagaccagg    14340
cgtgagcttc agcggctcct cgcccagggg agttgtgcag acggcacctg tttctttcgg    14400
caacagtgtg ggacagcgag cacggagtca caacccggga gctcacccca gccgtggcgg    14460
ccgggttttt cacgggggt  gggccgcgtg ggcaccgagc gcctgcgtgg ccaaccctgg    14520
```

```
tcactcggct gtagccacca gaggtccagc tgtgtggccc aaggctcccc ccataaatcg    14580
tgtcattagc acagaccgcc tggtttcagg gtctttgtgt gtgggcttgg ctgatcgcag    14640
gatcctggcg atggtagtca ggaaggggcc gtgctcccct tgagggggcaa ggtggagaga   14700 agtgctggag aggagacttg ctggcgggta cctggcactt gccacagcca ggctccactc    14760
ccctggggaa aggcgtggat ggtgggctgt gcacgccgct ccactcaggg cttagagcgc    14820
ctggcttaag gcgttgattt cctgtgtggg aagtggatga gttttctaca gctgccgtga    14880
ccaagcacca cagactgcgg ggccgaagcc acagaaacgc gtggcctcct gcttctggag    14940
gcctggaggc tgagctagcg gtggtgtcgg cagggtgggc tccccgccag ggccgcgagg    15000
gagctgcctt ccaggcctct ccacggcgcc gggggccgcc ggctgcacct ctccagcctc    15060
catctccgtc atcctgtggc cttgtcccg cgggcctctg tgcctgtcct cctcttttga     15120
caagaacacc ggagatacac aaaggtacac aaaagcgggc ctttgttcaa gctggcaaaa    15180
gagatcttct tcagaaaccc ctgcttgcgg gggagagagc tgagctccgt tcccgcccca    15240
gcagaggcgg cctggccttg cgaagggaga aggagggagt cgggaggggg cgagtgcagg    15300
ctcaggtgaa agatgacggg gcagccgcg tccttgccgc gaggccagcc gtgtgtggga    15360
gctgccggtg cttaccaagg ttgggatgct tccgtcccgt ggagactggg agactgggcc    15420
ccgcgcctcc tgaggtttcc gtttccaagg agtggctgcg gggccctcgg gaaagccct    15480 gggttgtggg tgctacacag atgtctcaaa gggacagggt aagccctttg tagtaaatgc    15540
tgtcagaaag ggaggtcagg tgttggccgg aacagacagt acatgctctg ggcagccctg    15600
agcgtttcca gacgggaact cactcaaaag ggggctgggg cgtcccaggg gcgcggcctt    15660
aggctcccag aggccccgcg agtggtggc cgggtgtctt cgggcagggg tttgagtgca    15720
gtgtgcctgc cgagaggttc tgcagttccc agtgtttaac aaaattcagt gtccactctt    15780
gatctgcaca aactctccca tcctggcggc cccgggtgtg gactgggcc tgtgtttact    15840 ttgccctatt cgtgtctggc ctccttttgt cccaagtctc agagagacgg agagagatcc    15900
cctgctgggg ctgtagctgc aaggccaccg ggttcagccc tcgaggcctg cttgccgggg    15960
cagtgactaa gccgttgaca acctcaaggc agctttgtgc tccttcgtct ctttggggat    16020
ctctttttgc cccatctgtg tgtcaccctg tggcagaggg ttaaggtggg cagctgggga    16080
gggttgggtg gcccttgggc tcatgaggcc ctagggcacc caggtttggg ggtgccgagg    16140
gcaggaaaaa aggcctcatg gcgcgcaggc ctcagccgct tgcgggttgc cccgggcttg    16200
cggatggcag gagtgggccg ctggggagaa agcagtgctg acaggaagtg gcttttatc    16260 ctgcagcaga tggctgagga caaggcctct gtgaaagccc aggtgacgtc cttgctcggg    16320
gagctgcagg agagccagag tcgcttggag gctgccacta aggaatgcca ggctctggag    16380
ggtcggtgag tcggggagc cggctccgga gaccccttcc agggtttcca aaagcaatga    16440
ggtgggttta gggcctcca gggtgctcct tgatgaggat agaccggggc aggctgcgta    16500
aacacgtcgg ggcagacgtc gggagaggtc tgggccaggc atccgggacc tgggtcccag    16560
ccggctctcc gcactctgtg accctttgat ggagtttgga ttatttcctt aggaggcatt    16620
ctgggggccc cgagcccaca cccacagtgt ctagttctct ggaaggactt ctgggaccgg    16680
cgcacagtcg ccctcgtggc tgaggttgat gacaggggaaa aaggcacagg gcaggagccg   16740
ccagggcagg agccgtgggg ggagttggag aagccctgtc ccagcctccc gctgccctgc    16800
gagcggcaca gtgagaagcg cctcccacac gggccatgtt cctgcccagg gatgcccgct    16860
agagactcag cgccctgggt gtttactggg ggcaggtcct gtcagcgccc tctgccaggc    16920
```

```
aggtacctaa atccccgact cccagcagca gagcgggtgc tcacgtcaac cacgttcttc   16980
ctacaaatgg cctaggtgca gggaccgacc ttgaccacta gagaaagtgt cactgtggca   17040
agggaacttc accagccaag ggccaacctt gccagccggt ggcctcaggc ctgctggtta   17100
ctctcttttg caaagggtc ttggttcttg tgagtgggac cattgggtca aagggcaggg   17160
aggtttctgt ggttctcatt cggtcctgct tctgccctcc agacagatgg atcagctgcc   17220
agggggccc cagccatccc agcacagtag gcggtcaagg tgcacttggg gcagccagca   17280
gggcagaggg gagggagct tgacccaggc tctgatgggc agaggaacc cgtgcagggt   17340
gtgggggcag tatgcaggca ggcgcggagg ggagagccaa gcagccaggc ctgccaggca   17400
gagttggggt gactgagaa gggccgtgtc tgcctgtggc cagaggccac ccaggacctg   17460
gacagatgca cccaccattg tccctgcagt gaggctgtgg aagggcttgg tgtggtggga   17520
tgaggccaga ccctggaaac tggaggttaa gggagctgta gggggcaggt gtgggaact   17580
gagcatccga gcaggtcgtc tgggactcca gcagagctct gggcagcagc agggatgggg   17640
ccgaggcccg gtctgcattg agctcagtgc ttgcacgccc aggtgggcag cctctcattt   17700
ttggaacagc agtctctcct gaccccctcc actgagactg cttttgctgg ggccccagc   17760
agtcccccag tggaactcca cgggcagtta cgagggctcc tctcacctgg ccccagcact   17820
gcgggatgca ggcgacccca tccttttctt ggaccacccc cttccctgg cttccaggtc   17880
tccttgccat ctgtacttgg tcacctgctg gcccctgca ttgaagcaaa cacgtcttaa   17940
gcaaagctcc tcacctgctg ctcccacctg gcccctgca gttgtcctcg tgtctgttga   18000
cggtgcctcc accctgccgc ctggcatcag ctcgcagtca caggtgttc agagccgacc   18060
cccacccccc gcccacgccc tgcgcatagc ccctcccgtc ccccgttcg tcctccctga   18120
gtctgctctt tccccgtgcc agggcccggg cggccagcga gcaggcgcgg cagctggaga   18180
gtgagcgcga ggcgctgcag cagcagcaca gcgtgcaggt ggaccagctg cgcatgcagg   18240
gccagagcgt ggaggccgcg ctccgcatgg agcgccaggc cgcctcggag gagaagtgag   18300
tcagcggggg cggggccgca ccgcagggtc tgtggttcta cacttgatct tagccgaaag   18360
gctgagaagt gtcgggtcca tggttctttc tgccttctga ggactccttc agattctgcc   18420
tgtggctgtg ggcccattct gtcccttagc cttgctaacg gtagaggcga ccatgatgac   18480
acccggtttg tctttgatac agtcatgcca tctgctctcc agaccacgtt tcactgcgtg   18540
tccacacgtg gcctttttg tagttttttt tcctagcca ctaggtcatc aggggacttg   18600
tcctttaaaa cccttctag gccaggtgct gtggctcacg cctgtaatcc caacactttg   18660
ggaggccaaa gtgggtagat ggcttaagcc cgggagttcc aagaccagcc tgggcaacag   18720
aaagacaaca aaaatacccc caaacccccc cgtctaccag catccaatct gggacctcag   18780
gttcctgtcc ttggcgtgcc ttttcagtct cctttaatct agaacagttc ccctgccttt   18840
ctgagctgtt tgtgaagttc acagttttga agagtgcagg gtagttccat tgtattatta   18900
ctattatttt caagacaggg tcttgctcta ccgtccaggc tggagtgcag tggcataatc   18960
tcggcttact gtaccttccg cctcttggtc tcaagcgatc ctcccaggta gctgggacta   19020
taggcgcagg ccagcacacc tggctaattt ttgcattttt ggtagaggtg gcgttttcct   19080
atgttgcccg ggctggtctt gaactcctga gctcaagcga tcctcctgcc ttggcttctc   19140
aaagtgttgg gattatgggc gtgagccacc gcgtctggcc gcgattttat tataaacatt   19200
aaaaatacta gcttttagga aaacgatatt aactgcctgg tgaccagccc accaaagcct   19260
```

```
gctttagagt tgacggcctc aggagtcctc acacagcctt ggaagacccc attccaggcc    19320
tgtgatgcga gggagggaag aagggggta gagttggaag caggcagcac cgtggctgga    19380
ctggcatgag gtggtttctc cagcaaaagc tccctttcct caggaggaag ctggcccagt    19440
tgcaggtggc ctatcaccag ctcttccaag aatacgacaa ccacatcaag agcagcgtgg    19500
tgggcagtga gcggaagcga gtgagtgcga ccactggggc tcttagggct ggccttgcct    19560
cttcctctcc ccgtggccct gaaccttgag aatgggtcct gccttagact tgccttagac    19620
ctgtgtcagg ctgcagctgc gacagctcag ggaagctgtg gggagatggc aaccccagga    19680
tgttgctctc aggagtgtca gcaggccatc ttaatggggg gctgggccag agccttgggg    19740
tgctccctct gtggggctgg ggacgtcttg tctccatgga cattccctct gccagccat    19800 cgccatctgg cacctggctc agcttccccc aagccaaggt aagcccgaca gcatttccac    19860
cccagtgttg gctgggagcc ttttcctagt ttgtcctcat cagacctaag ctggggtgca    19920
gtttgctagt gatcacattt tagcaggaca ccgtcaatcg taagtgtacc cagaggagat    19980
ttataaggac aaagcctgaa gccaggtcac atggggaaga gttagctaca aaactggcca    20040
cttaatctct ggaggggggc gttggtgggg tgtgtctgtg tgtgtctcag ggggctggag    20100
atgcctgcgt gggaggagtg cacctctgac caggtggcag agtggaagga ctgagggctc    20160
tcagctgagc tgtgcacatg gcgggcacag gaccggctgg ctgtgagtgg gtgtggcctg    20220
tggcctgtga agggtgggag gagggctgtg gagctgggga ttctgggaag ggaatgtcgg    20280
cccagctggg aggttgtacc agatgacctc agcggcctct tcagtcctga aaaaacctc    20340 agcatctcct ctgtcgtttt gggccgtgac aggacgcagc catctccctg tgcacgctga    20400
gatcctgcaa tgggccctca aatcaggggc tggcatcacc cagcctggtc agccagggcc    20460
actctttcat ccttctcagt tcttctcagc cagcctcgcc ctgggctgac gaggctccgt    20520
cagctcccct tgcccgtcct tagggaatgc agctggaaga tctcaaacag cagctccagc    20580
aggccgagga ggccctggtg gccaaacagg aggtgatcga taagctgaag gaggaggccg    20640
agcagcacaa gattgtgatg gagaccgttc cggtgctgaa ggcccaggtg agggccctcc    20700
tctctgaccc accctggcac tgggacctgg agagtctctt tggcgtcttt ttttttttt    20760 tttgcttttg cttttttgaga ttgagttttg ctcttgttgc ccaggctgga gtgccactag    20820
tggcacgatc ttggctcact gcaacctctg ccttccgggt tcaaacaatt ctctttgcct    20880
cagcctcctg agtagctggg attacaggcg cctgccgcca tgcccgtcta attttttgtat    20940 ttttagtaga cagggtttt caccatgttg gcccagctgg tctcgaactt ctggcctcag    21000
gtgatctgcc caccgcagtc tctcaaagtt ctgggattac aggcgtgagc caccgcaccc    21060
ggcctctttg gcatcatttt gtagtggcct ttcgtaagct tctgagccac ttgtgctgct    21120
ccttagacct ctcggtgagc ttggcattac tcgccgacgt atctgtttcc tctgcaccgc    21180 tggggggctct gggaggacag cagtgggttc tgctttgttc ctgtggtgcc tggcgcagtg    21240
cctggtgggt ggctggcttg tggcgggcac atccctttct gttggatttg ccaggcggat    21300
atctacaagg cggacttcca ggctgagagg caggcccggg agaagctggc cgagaagaag    21360
gagctcctgc aggagcagct ggagcagctg cagagggagt acagcaaact gaaggccagc    21420
tgtcaggagt cggccaggtg ggcctctgag agcgtgcccg tgtgagcagt gggtgcgaca    21480 ctgggggggtc gccagtggtg acccgcagt gggtgcgaca ctgggggggtt gccagtggtg    21540 accacaggag acgatggct cctggtgttc tgggttaggg ctcactgtgg tccctctcct    21600
ctcacctgag cttccaagag ctgctttgac actagtccag ccaaggagct ttacagaaat    21660
```

-continued

```
gcgtggcttg actggacggt ttctgttttc aaaggatcga ggacatgagg aagcggcatg    21720
tcgaggtctc ccaggccccc ttgccccccg ccctggtga gtgagcgaga actgggcctg    21780
cgggaggagg tgggtgggga gggcaggtgc tgcgccgcgg gaggtcacag ttcgaccttc    21840
ctgttgctct ctggagactt gacggcggga gctcgtgtag gccacccat cggtagccca    21900 cccccttccc cgaggctaag ggaggcatgc cgtggtagcg gcggctcctg gtcttacatg    21960
agtggcctgt gagaccaggc ctgccattga cagtcctgcc aagtctccgt ccccctccat    22020 cctcccttc cctctgactc ttctcttttc ccagcctacc tctcctctcc cctgccctg    22080 cccagccaga ggaggagccc cccgaggag ccacctgact tctgctgtcc caagtgccag    22140
tatcaggccc ctgatatgga caccctgcag atacatgtca tggagtgcat tgagtagggc    22200
cggccagtgc aaggccactg cctgccgagg acgtgcccgg gaccgtgcag tctgcgcttt    22260
cctctcccgc ctgcctagcc caggatgaag ggctgggtgg ccacaactgg gatgccacct    22320
ggagccccac ccaggagctg gccgcggcac cttacgcttc agctgttgat ccgctggtcc    22380
cctcttttgg ggtagatgcg gccccgatca ggcctgactc gctgctcttt ttgttcccttt   22440 ctgtctgctc gaaccacttg cctcgggcta atccctccct cttcctccac ccggcactgg    22500
ggaagtcaag aatggggcct ggggctctca gggagaactg cttcccctgg cagagctggg    22560
tggcagctct tcctcccacc ggacaccgac ccgcccgctg ctgtgccctg ggagtgctgc    22620
cctcttacca tgcacacggg tgctctcctt ttgggctgca tgctattcca ttttgcagcc    22680
agaccgatgt gtatttaacc agtcactatt gatggacatt tgggttgttt cccatctttt    22740
tgttaccata aataatggca tagtaaaat ccttgtgcat tagtcgtgcg tatctttggc    22800
atagattctg agaagtgaca ccactgagca tgggcgatgg cgtagatggt acctgagccc    22860
ccttcctcct tggagcttgg tttcccatct ctccccaccc cctatttccc tagccttgcc    22920
aaggaggagg tgggaaagcc cgtttgggtt tttgtcattc gctaggccat gcagttctct    22980
gttaagagtg agcttaaaca tctttcctga ggctttaagg acctttttta gttctgcttc    23040
tgaatgggct gctcatatca tatatatata tgtatatgta tagttgtgta tatgtatgtg    23100
tgtgtg                                                                23106
```

SEQ ID NO 2
<211> LENGTH: 419
<212> TYPE: PRT
<213> ORGANISM: human

<400> SEQUENCE: 2

```
Met Asn Arg His Leu Trp Lys Ser Gln Leu Cys Glu Met Val Gln Pro
1               5                   10                  15

Ser Gly Gly Pro Ala Ala Asp Gln Asp Val Leu Gly Glu Glu Ser Pro
            20                  25                  30

Leu Gly Lys Pro Ala Met Leu His Leu Pro Ser Glu Gln Gly Ala Pro
        35                  40                  45

Glu Thr Leu Gln Arg Cys Leu Glu Glu Asn Gln Glu Leu Arg Asp Ala
    50                  55                  60

Ile Arg Gln Ser Asn Gln Ile Leu Arg Glu Arg Cys Glu Glu Leu Leu
65                  70                  75                  80

His Phe Gln Ala Ser Gln Arg Glu Glu Lys Glu Phe Leu Met Cys Lys
                85                  90                  95

Phe Gln Glu Ala Arg Lys Leu Val Glu Arg Leu Gly Leu Glu Lys Leu
            100                 105                 110
```

-continued

```
Asp Leu Lys Arg Gln Lys Glu Gln Ala Leu Arg Glu Val Glu His Leu
            115                 120                 125
Lys Arg Cys Gln Gln Gln Met Ala Glu Asp Lys Ala Ser Val Lys Ala
        130                 135                 140
Gln Val Thr Ser Leu Leu Gly Glu Leu Gln Glu Ser Gln Ser Arg Leu
145                 150                 155                 160
Glu Ala Ala Thr Lys Glu Cys Gln Ala Leu Glu Gly Arg Ala Arg Ala
                165                 170                 175
Ala Ser Glu Gln Ala Arg Gln Leu Glu Ser Glu Arg Glu Ala Leu Gln
            180                 185                 190
Gln Gln His Ser Val Gln Val Asp Gln Leu Arg Met Gln Gly Gln Ser
        195                 200                 205
Val Glu Ala Ala Leu Arg Met Glu Arg Gln Ala Ala Ser Glu Glu Lys
210                 215                 220
Arg Lys Leu Ala Gln Leu Gln Val Ala Tyr His Gln Leu Phe Gln Glu
225                 230                 235                 240
Tyr Asp Asn His Ile Lys Ser Ser Val Val Gly Ser Glu Arg Lys Arg
                245                 250                 255
Gly Met Gln Leu Glu Asp Leu Lys Gln Gln Leu Gln Gln Ala Glu Glu
            260                 265                 270
Ala Leu Val Ala Lys Gln Glu Val Ile Asp Lys Leu Lys Glu Glu Ala
        275                 280                 285
Glu Gln His Lys Ile Val Met Glu Thr Val Pro Val Leu Lys Ala Gln
290                 295                 300
Ala Asp Ile Tyr Lys Ala Asp Phe Gln Ala Glu Arg Gln Ala Arg Glu
305                 310                 315                 320
Lys Leu Ala Glu Lys Lys Glu Leu Leu Gln Glu Leu Glu Gln Leu
                325                 330                 335
Gln Arg Glu Tyr Ser Lys Leu Lys Ala Ser Cys Gln Gly Ser Ala Arg
            340                 345                 350
Ile Glu Asp Met Arg Lys Arg His Val Glu Val Ser Gln Ala Pro Leu
        355                 360                 365
Pro Pro Ala Pro Ala Tyr Leu Ser Ser Pro Leu Ala Leu Pro Ser Gln
370                 375                 380
Arg Arg Ser Pro Pro Glu Glu Pro Pro Asp Phe Cys Cys Pro Lys Cys
385                 390                 395                 400
Gln Tyr Gln Ala Pro Asp Met Asp Thr Leu Gln Ile His Val Met Glu
                405                 410                 415
Cys Ile Glu

<210> SEQ ID NO 3
<211> LENGTH: 2035
<212> TYPE: DNA
<213> ORGANISM: Human

<400> SEQUENCE: 3
cgagctggac tgtttctact cctccctcct cctccactgc ggggtctgac cctactcctt      60
gtgtgaggac tcctctagtt cagagacata ttctgttcac caaacttgac tgcgctctat     120
cgaggtcgtt aaattcttcg gaatgcctc acatatagtt tggcagctag cccttgccct      180
gttggatgaa taggcaccctc tggaagagcc aactgtgtga tggtgcag cccagtggtg      240 gcccggcagc agatcaggac gtactgggcg aagagtctcc tctggggaag ccagccatgc      300
tgcacctgcc ttcagaacag ggcgctcctg agaccctcca gcgctgcctg aggagaatc      360
```

-continued

```
aagagctccg agatgccatc cggcagagca accagattct gcgggagcgc tgcgaggagc    420
ttctgcattt ccaagccagc cagagggagg agaaggagtt cctcatgtgc aagttccagg    480
aggccaggaa actggtggag agactcggcc tggagaagct cgatctgaag aggcagaagg    540
agcaggctct gcgggaggtg gagcacctga agagatgcca gcagcagatg gctgaggaca    600
aggcctctgt gaaagcccag gtgacgtcct tgctcgggga gctgcaggag agccagagtc    660
gcttggaggc tgccactaag gaatgccagg ctctggaggg tcgggcccgg gcggccagcg    720
agcaggcgcg gcagctggag agtgagcgcg aggcgctgca gcagcagcac agcgtgcagg    780
tggaccagct gcgcatgcag ggccagagcg tggaggccgc gctccgcatg gagcgccagg    840
ccgcctcgga ggagaagagg aagctggccc agttgcaggt ggcctatcac cagctcttcc    900
aagaatacga caaccacatc aagagcagcg tggtgggcag tgagcggaag cgaggaatgc    960
agctggaaga tctcaaacag cagctccagc aggccgagga ggccctggtg ccaaacagg    1020
aggtgatcga taagctgaag gaggaggccg agcagcacaa gattgtgatg gagaccgttc   1080
cggtgctgaa ggcccaggcg gatatctaca aggcggactt ccaggctgag aggcaggccc   1140
gggagaagct ggccgagaag aaggagctcc tgcaggagca gctggagcag ctgcagaggg   1200
agtacagcaa actgaaggcc agctgtcagg agtcggccag gatcgaggac atgaggaagc   1260
ggcatgtcga ggtctcccag gcccccttgc ccccgcccc tgcctacctc tcctctcccc    1320
tggccctgcc cagccagagg aggagccccc ccgaggagcc acctgacttc tgctgtccca   1380
agtgccagta tcaggcccct gatatggaca ccctgcagat acatgtcatg gagtgcattg   1440
agtagggccg gccagtgcaa ggccactgcc tgccgaggac gtgcccggga ccgtgcagtc   1500
tgcgctttcc tctcccgcct gcctagccca ggatgaaggg ctgggtggcc acaactggga   1560
tgccacctgg agccccaccc aggagctggc cgcggcacct tacgcttcag ctgttgatcc   1620
gctggtcccc tctttggggg tagatgcggc cccgatcagg cctgactcgc tgctcttttt   1680
gttcccttct gtctgctcga accacttgcc tcgggctaat ccctccctct cctccaccc    1740
ggcactgggg aagtcaagaa tggggcctgg ggctctcagg gagaactgct cccctggca    1800
gagctgggtg gcagctcttc ctcccaccgg acaccgaccc gcccgctgct gtgccctggg   1860
agtgctgccc tcttaccatg cacacgggtg ctctcctttt gggctgcatg ctattccatt   1920
ttgcagccag accgatgtgt atttaaccag tcactattga tggacatttg ggttgtttcc   1980
catctttttg ttaccataaa taatggcata gtaaaaatcc ttgtgcatta aaaaa         2035
```

<210> SEQ ID NO 4
<211> LENGTH: 20
<212> TYPE: DNA
<213> ORGANISM: Human

<400> SEQUENCE: 4
gtcccatcag gtggggaaag                                               20

<210> SEQ ID NO 5
<211> LENGTH: 20
<212> TYPE: DNA
<213> ORGANISM: Human

<400> SEQUENCE: 5
gaagggcgac cgcgaaactg                                               20

<210> SEQ ID NO 6

```
<211> LENGTH: 20
<212> TYPE: DNA
<213> ORGANISM: Human

<400> SEQUENCE: 6
ctgctgacag gtgtggtcct                                              20

<210> SEQ ID NO 7
<211> LENGTH: 20
<212> TYPE: DNA
<213> ORGANISM: Human

<400> SEQUENCE: 7
acttgggcgg cgagctggac                                              20

<210> SEQ ID NO 8
<211> LENGTH: 20
<212> TYPE: DNA
<213> ORGANISM: Human

<400> SEQUENCE: 8
tggcagctag gtatctgatt                                              20

<210> SEQ ID NO 9
<211> LENGTH: 20
<212> TYPE: DNA
<213> ORGANISM: Human

<400> SEQUENCE: 9
tctctttcag cccttgccct                                              20

<210> SEQ ID NO 10
<211> LENGTH: 20
<212> TYPE: DNA
<213> ORGANISM: Human

<400> SEQUENCE: 10
gagctccgag gtgaggaaag                                              20

<210> SEQ ID NO 11
<211> LENGTH: 20
<212> TYPE: DNA
<213> ORGANISM: Human

<400> SEQUENCE: 11
ctgccaccag atgccatccg                                              20

<210> SEQ ID NO 12
<211> LENGTH: 20
<212> TYPE: DNA
<213> ORGANISM: Human

<400> SEQUENCE: 12
atgccagcag gtagtcgggg                                              20

<210> SEQ ID NO 13
<211> LENGTH: 20
<212> TYPE: DNA
<213> ORGANISM: Human

<400> SEQUENCE: 13
tatcctgcag cagatggctg                                              20
```

```
<210> SEQ ID NO 14
<211> LENGTH: 20
<212> TYPE: DNA
<213> ORGANISM: Human

<400> SEQUENCE: 14
tggagggtcg gtgagtcggg                                          20

<210> SEQ ID NO 15
<211> LENGTH: 20
<212> TYPE: DNA
<213> ORGANISM: Human

<400> SEQUENCE: 15
cccgtgccag ggcccgggcg                                          20

<210> SEQ ID NO 16
<211> LENGTH: 20
<212> TYPE: DNA
<213> ORGANISM: Human

<400> SEQUENCE: 16
cggaggagaa gtgagtcagc                                          20

<210> SEQ ID NO 17
<211> LENGTH: 20
<212> TYPE: DNA
<213> ORGANISM: Human

<400> SEQUENCE: 17
ctttcctcag gaggaagctg                                          20

<210> SEQ ID NO 18
<211> LENGTH: 20
<212> TYPE: DNA
<213> ORGANISM: Human

<400> SEQUENCE: 18
gcggaagcga gtgagtgcga                                          20

<210> SEQ ID NO 19
<211> LENGTH: 20
<212> TYPE: DNA
<213> ORGANISM: Human

<400> SEQUENCE: 19
ccgtccttag ggaatgcagc                                          20

<210> SEQ ID NO 20
<211> LENGTH: 20
<212> TYPE: DNA
<213> ORGANISM: Human

<400> SEQUENCE: 20
gaaggcccag gtgagggccc                                          20

<210> SEQ ID NO 21
<211> LENGTH: 20
<212> TYPE: DNA
<213> ORGANISM: Human

<400> SEQUENCE: 21
gatttgccag gcggatatct                                          20
```

<210> SEQ ID NO 22
<211> LENGTH: 20
<212> TYPE: DNA
<213> ORGANISM: Human

<400> SEQUENCE: 22
agtcggccag gtgggcctct                                           20

<210> SEQ ID NO 23
<211> LENGTH: 20
<212> TYPE: DNA
<213> ORGANISM: Human

<400> SEQUENCE: 23
gttttcaaag gatcgaggac                                           20

<210> SEQ ID NO 24
<211> LENGTH: 20
<212> TYPE: DNA
<213> ORGANISM: Human

<400> SEQUENCE: 24
cccgcccctg gtgagtgagc                                           20

<210> SEQ ID NO 25
<211> LENGTH: 20
<212> TYPE: DNA
<213> ORGANISM: Human

<400> SEQUENCE: 25
cttttcccag cctacctctc                                           20

<210> SEQ ID NO 26
<211> LENGTH: 20
<212> TYPE: DNA
<213> ORGANISM: Human

<400> SEQUENCE: 26
ggaagtcagc ccagaaatgt                                           20

<210> SEQ ID NO 27
<211> LENGTH: 20
<212> TYPE: DNA
<213> ORGANISM: Human

<400> SEQUENCE: 27
gtacttactg ccccttcca                                            20

<210> SEQ ID NO 28
<211> LENGTH: 20
<212> TYPE: DNA
<213> ORGANISM: Human

<400> SEQUENCE: 28
gggcggggct tgtgttttta                                           20

<210> SEQ ID NO 29
<211> LENGTH: 20
<212> TYPE: DNA
<213> ORGANISM: Human

<400> SEQUENCE: 29
agaagcgcgg agcaggaacg                                           20

```
<210> SEQ ID NO 30
<211> LENGTH: 20
<212> TYPE: DNA
<213> ORGANISM: Human

<400> SEQUENCE: 30
ttcctgctcc gcgcttctgg                                              20

<210> SEQ ID NO 31
<211> LENGTH: 20
<212> TYPE: DNA
<213> ORGANISM: Human

<400> SEQUENCE: 31
ccaggagagc ccattcattc                                              20

<210> SEQ ID NO 32
<211> LENGTH: 20
<212> TYPE: DNA
<213> ORGANISM: Human

<400> SEQUENCE: 32
tctgctgggt aaggatgtgg                                              20

<210> SEQ ID NO 33
<211> LENGTH: 20
<212> TYPE: DNA
<213> ORGANISM: Human

<400> SEQUENCE: 33
tctgcaggtg gggagaagac                                              20

<210> SEQ ID NO 34
<211> LENGTH: 20
<212> TYPE: DNA
<213> ORGANISM: Human

<400> SEQUENCE: 34
cccagctccc ctccactgtc                                              20

<210> SEQ ID NO 35
<211> LENGTH: 22
<212> TYPE: DNA
<213> ORGANISM: Human

<400> SEQUENCE: 35
cacctggcgt cactcggcgg gt                                           22

<210> SEQ ID NO 36
<211> LENGTH: 20
<212> TYPE: DNA
<213> ORGANISM: Human

<400> SEQUENCE: 36
cagtgctgac aggaagtggc                                              20

<210> SEQ ID NO 37
<211> LENGTH: 23
<212> TYPE: DNA
<213> ORGANISM: Human

<400> SEQUENCE: 37
```
aaccctggaa ggggtctccg gag                    23

<210> SEQ ID NO 38
<211> LENGTH: 20
<212> TYPE: DNA
<213> ORGANISM: Human

<400> SEQUENCE: 38
catcagctcg cagtcacagg                        20

<210> SEQ ID NO 39
<211> LENGTH: 20
<212> TYPE: DNA
<213> ORGANISM: Human

<400> SEQUENCE: 39
ccgacacttc tcagcctttc                        20

<210> SEQ ID NO 40
<211> LENGTH: 20
<212> TYPE: DNA
<213> ORGANISM: Human

<400> SEQUENCE: 40 aaggggtag agttggaagc                         20

<210> SEQ ID NO 41
<211> LENGTH: 20
<212> TYPE: DNA
<213> ORGANISM: Human

<400> SEQUENCE: 41
aggcaagtct aaggcaggtc                        20

<210> SEQ ID NO 42
<211> LENGTH: 20
<212> TYPE: DNA
<213> ORGANISM: Human

<400> SEQUENCE: 42
gccactcttt catccttctc                        20

<210> SEQ ID NO 43
<211> LENGTH: 19
<212> TYPE: DNA
<213> ORGANISM: Human

<400> SEQUENCE: 43
tgggcaacaa gagcaaaac                         19

<210> SEQ ID NO 44
<211> LENGTH: 21
<212> TYPE: DNA
<213> ORGANISM: Human

<400> SEQUENCE: 44
tgcctggtgg gtggctggct t                      21

<210> SEQ ID NO 45
<211> LENGTH: 21
<212> TYPE: DNA
<213> ORGANISM: Human

<400> SEQUENCE: 45

-continued cagtgtcgca cccactgctc a                     21

<210> SEQ ID NO 46
<211> LENGTH: 20
<212> TYPE: DNA
<213> ORGANISM: Human

<400> SEQUENCE: 46
gctgctttga cactagtcca                       20

<210> SEQ ID NO 47
<211> LENGTH: 20
<212> TYPE: DNA
<213> ORGANISM: Human

<400> SEQUENCE: 47
cagagagcaa caggaaggtc                       20

<210> SEQ ID NO 48
<211> LENGTH: 20
<212> TYPE: DNA
<213> ORGANISM: Human

<400> SEQUENCE: 48
cggcggctcc tggtcttaca                       20

<210> SEQ ID NO 49
<211> LENGTH: 20
<212> TYPE: DNA
<213> ORGANISM: Human

<400> SEQUENCE: 49
gccacccagc ccttcatcct                       20

<210> SEQ ID NO 50
<211> LENGTH: 21
<212> TYPE: DNA
<213> ORGANISM: Human

<400> SEQUENCE: 50
cccttgccct gttggatgaa t                     21

<210> SEQ ID NO 51
<211> LENGTH: 21
<212> TYPE: DNA
<213> ORGANISM: Human

<400> SEQUENCE: 51
cgtcctcggc aggcagtggc c                     21

<210> SEQ ID NO 52
<211> LENGTH: 21
<212> TYPE: DNA
<213> ORGANISM: Human

<400> SEQUENCE: 52
ggccactgcc tgccgaggac g                     21

<210> SEQ ID NO 53
<211> LENGTH: 21
<212> TYPE: DNA
<213> ORGANISM: Human

```
<400> SEQUENCE: 53
accctccaga gcctggcatt g                                        21

<210> SEQ ID NO 54
<211> LENGTH: 21
<212> TYPE: DNA
<213> ORGANISM: Human

<400> SEQUENCE: 54
cattcctcgc ttccgctcac t                                        21

<210> SEQ ID NO 55
<211> LENGTH: 21
<212> TYPE: DNA
<213> ORGANISM: Human

<400> SEQUENCE: 55
cttcagatcg agcttctcga g                                        21

<210> SEQ ID NO 56
<211> LENGTH: 21
<212> TYPE: DNA
<213> ORGANISM: Human

<400> SEQUENCE: 56
gcggacttcc aggctgagag g                                        21

<210> SEQ ID NO 57
<211> LENGTH: 43
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(43)
<223> OTHER INFORMATION: Primer

<400> SEQUENCE: 57
ctaatacgac tcactatagg gctcgagcag cctccgaggg cag                43

<210> SEQ ID NO 58
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(16)
<223> OTHER INFORMATION: Primer

<400> SEQUENCE: 58
aattctgccc tcggag                                              16

<210> SEQ ID NO 59
<211> LENGTH: 27
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(27)
<223> OTHER INFORMATION: Primer

<400> SEQUENCE: 59
```

```
ccatcctaat acgactcact atagggc                                              27

<210> SEQ ID NO 60
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(21)
<223> OTHER INFORMATION: Primer

<400> SEQUENCE: 60
tcactatagg gctcgagcag c                                                    21

<210> SEQ ID NO 61
<211> LENGTH: 22
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(22)
<223> OTHER INFORMATION:

<400> SEQUENCE: 61
cggcagagca accagattct gc                                                   22

<210> SEQ ID NO 62
<211> LENGTH: 15
<212> TYPE: DNA
<213> ORGANISM: Human

<400> SEQUENCE: 62
ctgccttcag aacag                                                           15

<210> SEQ ID NO 63
<211> LENGTH: 25
<212> TYPE: DNA
<213> ORGANISM: Human

<400> SEQUENCE: 63
ctgccttcac ctgccttcag aacag                                                25

<210> SEQ ID NO 64
<211> LENGTH: 22
<212> TYPE: PRT
<213> ORGANISM: Human

<400> SEQUENCE: 64

Ser Pro Leu Gly Lys Pro Ala Met Leu His Leu Pro Ser Glu Gln Gly
1               5                   10                  15

Ala Pro Glu Thr Leu Gln
            20

<210> SEQ ID NO 65
<211> LENGTH: 22
<212> TYPE: PRT
<213> ORGANISM: Human
<220> FEATURE:
<221> NAME/KEY: MISC_FEATURE
<222> LOCATION: (22)..(22)
<223> OTHER INFORMATION: Xaa equals unknown
```

<400> SEQUENCE: 65

Ser Pro Leu Gly Lys Pro Ala Met Leu His Leu Pro Ser Pro Ala Phe
1               5                   10                  15

Arg Thr Gly Arg Ser Xaa
            20

<210> SEQ ID NO 66
<211> LENGTH: 24
<212> TYPE: DNA
<213> ORGANISM: Human

<400> SEQUENCE: 66
aggccccctt gcccccgcc cctg                                         24

<210> SEQ ID NO 67
<211> LENGTH: 25
<212> TYPE: DNA
<213> ORGANISM: Human

<400> SEQUENCE: 67 aggcccctt gccccccgc ccctg                                         25

<210> SEQ ID NO 68
<211> LENGTH: 33
<212> TYPE: PRT
<213> ORGANISM: human

<400> SEQUENCE: 68

Val Glu Val Ser Gln Ala Pro Leu Pro Pro Ala Pro Ala Tyr Leu Ser
1               5                   10                  15

Ser Pro Leu Ala Leu Pro Ser Gln Arg Arg Ser Pro Pro Glu Glu Pro
            20                  25                  30

Pro

<210> SEQ ID NO 69
<211> LENGTH: 34
<212> TYPE: PRT
<213> ORGANISM: human
<220> FEATURE:
<221> NAME/KEY: MISC_FEATURE
<222> LOCATION: (34)..(34)
<223> OTHER INFORMATION: Xaa equals unknown

<400> SEQUENCE: 69

Val Glu Val Ser Gln Ala Pro Leu Pro Pro Arg Pro Cys Leu Pro Leu
1               5                   10                  15

Leu Ser Pro Gly Pro Ala Gln Pro Glu Glu Pro Pro Arg Gly Ala
            20                  25                  30

Thr Xaa

<210> SEQ ID NO 70
<211> LENGTH: 25
<212> TYPE: DNA
<213> ORGANISM: Human

<400> SEQUENCE: 70
tcaggcccct gatatggaca ccctg                                       25

<210> SEQ ID NO 71
<211> LENGTH: 25
<212> TYPE: DNA
<213> ORGANISM: Human

<400> SEQUENCE: 71
tcaggcccct gatgtggaca ccctg    25

<210> SEQ ID NO 72
<211> LENGTH: 19
<212> TYPE: PRT
<213> ORGANISM: Human

<400> SEQUENCE: 72

Gln Tyr Gln Ala Pro Asp Met Asp Thr Leu Gln Ile His Val Met Glu
1               5                   10                  15

Cys Ile Glu

<210> SEQ ID NO 73
<211> LENGTH: 19
<212> TYPE: PRT
<213> ORGANISM: Human

<400> SEQUENCE: 73

Gln Tyr Gln Ala Pro Asp Val Asp Thr Leu Gln Ile His Val Met Glu
1               5                   10                  15

Cys Ile Glu

<210> SEQ ID NO 74
<211> LENGTH: 21
<212> TYPE: DNA
<213> ORGANISM: Human

<400> SEQUENCE: 74
caagagctcc gaggtgagga a    21

<210> SEQ ID NO 75
<211> LENGTH: 21
<212> TYPE: DNA
<213> ORGANISM: Human

<400> SEQUENCE: 75
caagagctct gaggtgagga a    21

<210> SEQ ID NO 76
<211> LENGTH: 20
<212> TYPE: PRT
<213> ORGANISM: Human

<400> SEQUENCE: 76

Leu Gln Arg Cys Leu Glu Glu Asn Gln Glu Leu Pro Asp Ala Ile Arg
1               5                   10                  15

Gln Ser Asn Gln
            20

<210> SEQ ID NO 77
<211> LENGTH: 11
<212> TYPE: PRT
<213> ORGANISM: Human

<400> SEQUENCE: 77

Leu Gln Arg Cys Leu Glu Glu Asn Gln Glu Leu
1               5                   10

<210> SEQ ID NO 78
<211> LENGTH: 35

```
<212> TYPE: DNA
<213> ORGANISM: Human
<220> FEATURE:
<221> NAME/KEY: misc_feature
<222> LOCATION: (1)..(35)
<223> OTHER INFORMATION: N equals any unknown nucleotide sequences

<400> SEQUENCE: 78
tgcanctaca gctgccnagt tcccagtgnc tgcag                                35

<210> SEQ ID NO 79
<211> LENGTH: 35
<212> TYPE: DNA
<213> ORGANISM: Human
<220> FEATURE:
<221> NAME/KEY: misc_feature
<222> LOCATION: (1)..(35)
<223> OTHER INFORMATION: N equals any unknown nucleotide sequences

<400> SEQUENCE: 79
gggcnctggg gctgccnagt tccgagcana agctt                                35
```